(12) United States Patent
Marugan et al.

(10) Patent No.: US 9,550,742 B2
(45) Date of Patent: Jan. 24, 2017

(54) 11-OXO-10,11-DIHYDRODIBENZO[B,F][1,4]THIAZEPINE S-OXIDE DERIVATIVES AND THEIR USE AS DOPAMINE D2 RECEPTOR ANTAGONISTS

(71) Applicant: The United States of America, as Represented by the Secretary, Department of Health and Human, Washington, DC (US)

(72) Inventors: Juan Jose Marugan, Gaithersburg, MD (US); Jingbo Xiao, Rockville, MD (US); Marc Ferrer, Potomac, MD (US); Noel Terrence Southall, Potomac, MD (US); R. Benjamin Free, Germantown, MD (US); David Robert Sibley, Gaithersburg, MD (US)

(73) Assignee: THE UNITED STATES OF AMERICA, AS REPRESENTED BY THE SECRETARY, DEPARTMENT OF HEALTH AND HUMAN SERVICES, Washington, DC (US)

( * ) Notice: Subject to any disclaimer, the term of this patent is extended or adjusted under 35 U.S.C. 154(b) by 0 days.

(21) Appl. No.: 14/908,271

(22) PCT Filed: Jul. 29, 2014

(86) PCT No.: PCT/US2014/048619
§ 371 (c)(1),
(2) Date: Jan. 28, 2016

(87) PCT Pub. No.: WO2015/017412
PCT Pub. Date: Feb. 5, 2015

(65) Prior Publication Data
US 2016/0176831 A1   Jun. 23, 2016

Related U.S. Application Data

(60) Provisional application No. 61/859,532, filed on Jul. 29, 2013.

(51) Int. Cl.
*C07D 281/16* (2006.01)
*C07D 417/12* (2006.01)

(52) U.S. Cl.
CPC .......... *C07D 281/16* (2013.01); *C07D 417/12* (2013.01)

(58) Field of Classification Search
None
See application file for complete search history.

(56) References Cited

U.S. PATENT DOCUMENTS

2010/0022509 A1   1/2010   Fahey et al.

FOREIGN PATENT DOCUMENTS

| WO | 2007047737 A1 | 4/2007 |
| WO | 2008036139 A2 | 3/2008 |
| WO | 2010062565 A1 | 6/2010 |

OTHER PUBLICATIONS

Database CAPLUS in STN, Acc. No. 2011:803217, Newton et al., Bioorganic & Medicinal Chemistry (2011), 19(13), pp. 3956-3964 (abstract).*
Database CAPLUS in STN, Acc. No. 2009:846103, Goldfarb, US 2009/0163545 A1 (Jun. 25, 2009) (abstract).*
Database CAPLUS in STN, Acc. No. 2008:377985, Fahey et al., WO 2008/036139 A2 (Mar. 27, 2008) (abstract).*
Free et al.; "Discovery, characterization, and optimization of highly selective D2 dopaminergic antagonists"; FASEB J., (Meeting Abstract Supplement) 655.7; 2013; 1 page; retreived on Jan. 28, 2016 from http://www.fasebj.org/cgi/content/meeting_abstract/27/1_MeetingAbstracts/655.7.
Grundt et al.; "Analogues of the dopamine D2 receptor antagonist L741,626: Binding, function, and SAR"; Bioorg. Med. Chem. Lett.; 2007; pp. 745-749.
International Search Report for International Application No. PCT/US2014/048619; International Filing Date Jul. 29, 2014; Date of Mailing Oct. 22, 2014; 5 pages.
Langlois et al.; "Pharmacology of JNJ-37822681, a Specific and Fast-Dissociating D2 Anatgonist for the Treatment of Schizophrenia"; Pharmacol. Exp. Ther., 342(1); 2012; pp. 91-105.
Newton et al.; "Evaluation of NTF1836 as an inhibitor of the mycothiol biosynthetic enzyme MshC in growing and non-replicating *Mycobacterium tuberculosis*"; Bioorganic and Medicinal Chemistry, 19(13); Jul. 1, 2011; pp. 3956-3964.
Vangveravong et al.; Synthesis and characterization of selective dopamine D2 receptor antagonists. 2. Azaindole, benzofuran, and benzothiophene analogs of L-741,626; Bioorg. Med. Chem.; 2010; pp. 5291-5300.

(Continued)

*Primary Examiner* — Brian J Davis
(74) *Attorney, Agent, or Firm* — Cantor Colburn LLP

(57) ABSTRACT

The disclosure includes compounds and pharmaceutically acceptable salts of Formula (I). Certain compounds and salts of Formula (I) are selective inhibitors of the Dopamine $D_2$ receptor. The variables $R_1$-$R_4$, n, and L are defined herein. The disclosure also provides methods of synthesizing compounds of Formula (I) and pharmaceutical compositions containing compounds of Formula (I). Additionally the disclosure provides methods or treating patients suffering from central nervous system disorders, including Tourette's syndrome, bipolar disorder, hyperprolactinemia, tardive dyskinesia, Huntington's chorea, psychosis, depression, or schizophrenia.

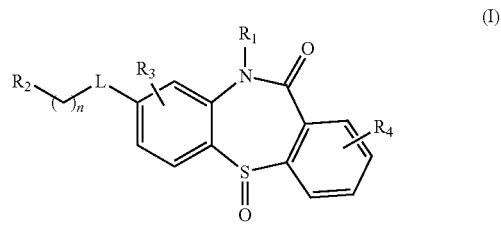

22 Claims, 2 Drawing Sheets

(56) References Cited

OTHER PUBLICATIONS

Vangveravong et al.; "Synthesis of N-substituted 9-azabicyclo[3.3.1]nonan-3α-γl carbamate analogs as σ2 receptor ligands"; Bioorg. Med. Chem.; 2006; pp. 6988-6997.

Written Opinion for International Application No. PCT/US2014/048619; International Filing Date Jul. 29, 2014; Date of Mailing Oct. 22, 2014; 6 pages.

Xiao et al.; "Discovery, optimization, and characterization of a novel series of dopamine D2 versus D3 receptor selective antagonists"; Probe Reports from the NIH Molecular Libraries Program [Internet]; 2013; pp. 1-21; accessed Jan. 28, 2016 from http://www.ncbi.nlm.nih.gov/books/NBK169449/.

Xiao et al.; "Discovery Optimization, and Characterization of Novel D 2 Dopamine Receptor Selective Antagonists"; J. Med. Chem., 57(8); Apr. 24, 2014; pp. 3450-3463.

* cited by examiner

11-OXO-10,11-DIHYDRODIBENZO[B,F][1,4]THIAZEPINE S-OXIDE DERIVATIVES AND THEIR USE AS DOPAMINE D2 RECEPTOR ANTAGONISTS

CROSS-REFERENCE TO RELATED APPLICATIONS

This Application is a U.S. National Stage Application of PCT/US2014/48619 filed Jul. 29, 2014, which claims priority of U.S. Provisional Application 61/859,532, filed 29 Jul. 2013, both of which are incorporated by reference in their entirety.

STATEMENT OF GOVERNMENT SUPPORT

This invention was made in part with government support from the US Department of Health and Human Services, National Institutes of Health. The government has certain rights in this invention.

BACKGROUND

G-protein coupled receptors (GPCRs) are among the most intensely investigated drug targets in the pharmaceutical industry. Over 40% of all FDA approved drugs target these important receptor proteins. Unfortunately, many of the ligands that are used as drugs or pharmacological tools are not selective and exhibit some unintended activity on non-target GPCRs or other proteins. This is because the orthosteric binding site is highly conserved among closely related types of GPCRs.

Dopamine receptors (DARs) belong to a large superfamily of neurotransmitter and hormone receptors. Five functionally active DARs have been identified in the mammalian genome. $D_1$-like DARs ($D_1$ and $D_5$) are $G\alpha s$ coupled, and $D_2$-like DARs ($D_2$, $D_3$ and $D_4$) are $G_{\alpha i/o}$ coupled. There are two isoforms of the $D_2$ DAR, short and long ($D_{2S}$ and $D_{2L}$), respectively, which are derived from alternative RNA splicing and vary in the size of their third intracellular loops. The $D_{2L}$ isoform is more prevalent, although both isoforms appear to be functionally similar. Amongst the DARs, the $D_2$ DAR is arguably one of the most validated drug targets in neurology and psychiatry. For instance, all receptor-based anti-Parkinsonian drugs work via stimulating the $D_2$ DAR (although controversy exists for a minor role of the $D_1$ DAR), whereas all FDA approved antipsychotic agents are antagonists of this receptor. The $D_2$ DAR is also therapeutically targeted in other disorders such as restless legs syndrome, tardive dyskinesia, Tourette's syndrome, psychosis, bipolar disorder, schizophrenia, and hyperprolactinemia. Most drugs targeting the $D_2$ DAR (orthosteric agonists and antagonists) are problematic, either by being less efficacious than desired or possessing limiting side effects, most of which are due to off-target cross-GPCR reactivity. It is thus desirable to develop a class of novel therapeutic agents with high selectivity for the $D_2$ DAR.

It should be noted that though the therapeutic potential for more selective $D_2$ DAR antagonists may be enormous, this approach may also provide a way forward for developing selective pharmacological probes. Amongst the $D_2$-like family of DARs ($D_2$, $D_3$, and $D_4$), only the $D_4$ DAR has ligands (both agonists and antagonists) that are truly specific, approaching 1,000 fold-selectively versus $D_2$ and $D_3$ DARs. This is not surprising given that the $D_4$ DAR is more structurally divergent compared to the $D_2/D_3$ DARs. $D_2$ and $D_3$ receptors share 78% homology in their transmembrane spanning domains, which harbor the ligand binding sites and thus the pharmacologic properties between these two receptor subtypes are quite similar. Therefore, it is very challenging to identify small molecules that can selectively bind to and/or functionally modulate either $D_2$ or $D_3$ DAR receptor subtypes. A high level of probe selectivity will allow for definitive in vivo studies of receptor function. With respect to the $D_3$ DAR, there are several compounds that exhibit good selectivity versus the $D_4$ DAR and moderate (a few hundred fold) selectivity versus the $D_2$ DAR. Some of these $D_3$-selective compounds have been used for in vivo experiments but the results have been controversial in many instances. In contrast, to the best of our knowledge, there are only few series of compounds that exhibit even moderate selectivity for the $D_2$ DAR receptor versus $D_3$ and $D_4$ within the $D_2$-like DAR subfamily. Selective antagonists of the $D_2$ DAR are useful for treatment of disorders currently treated with relatively non-selective $D_2$ antagonists, including Tourette's syndrome, tardive dyskinesia, Huntington's chorea, psychosis, bipolar disorder, depression, and schizophrenia.

Patients suffering from schizophrenia comprise the largest patient population that would benefit from highly selective $D_2$ DAR antagonists. Schizophrenia is characterized by delusions, hallucinations, social withdrawal, attention, and cognitive defects. All current FDA-approved antipsychotic drugs have $D_2$ DAR blocking properties. It is likely that $D_2$ DAR antagonism will remain a mainstay for the treatment of psychosis, especially for the treatment of so-called "positive" symptoms of this illness. Unfortunately, all antipsychotic drugs that antagonize $D_2$ DARs also interact with other GPCRs to varying degrees, including adrenergic, serotonergic, histaminergic, and cholinergic receptors. It is therefore not surprising that such drugs have multiple adverse effects including sedative, extra-pyramidal, endocrine, metabolic, and hypotensive properties. Because of the lack of highly selective ligands, it is not known to what extent other GPCRs contribute to the antipsychotic actions and/or associated side effects of these agents, although the $H_1$ histamine receptor has been implicated in weight gain.

The present disclosure fulfills the need for highly selective $D_2$ DAR compounds and also provides additional advantages.

SUMMARY

The present disclosure provides dihydrobenzo[b,f][1,4]thiazepine-8-carboxamides with selective affinity for the dopamine $D_2$ receptor.

In a first aspect the disclosure provides dihydrobenzo[b,f][1,4]thiazepine-8-carboxamide compounds of Formula I and the pharmaceutically acceptable salts thereof.

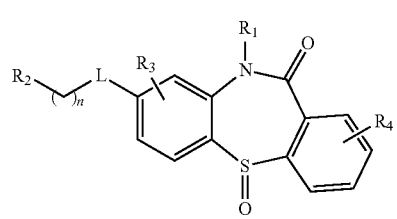

(Formula I)

Within Formula I the following conditions are met:
L is —NHC(O)—, —C(O)NH—, —OC(O)— or —C(O)O—; and n is and integer from 1 to 4 and

is unsubstituted or substituted with one or more substituents independently chosen from halogen, hydroxyl, amino, cyano, $C_1$-$C_4$alkyl, $C_1$-$C_4$alkoxy, $C_1$-$C_2$haloalkyl, and $C_1$-$C_2$haloalkoxy.

$R_1$ is hydrogen, $C_1$-$C_6$alkyl, $C_2$-$C_6$alkenyl, ($C_3$-$C_7$cycloalkyl)$C_0$-$C_2$alkyl, (phenyl)$C_0$-$C_2$alkyl, (mono- or di-$C_1$-$C_4$alkylamino)$C_1$-$C_4$alkyl, or (mono- or di-$C_1$-$C_4$alkylamino)$C_1$-$C_4$alkoxy.

$R_2$ is a mono-, bi-, or tricyclic carbocyclic or heterocyclic group, a (mono- or di-$C_1$-$C_4$alkylamino)$C_2$-$C_4$alkyl group, or $C_4$-$C_8$alkyl, each of which $R_2$ is unsubstituted or substituted with one more substituents independently chosen from halogen, hydroxyl, amino, nitro, cyano, $C_1$-$C_6$alkyl, $C_2$-$C_6$alkenyl, $C_2$-$C_6$alkynyl, —$OR_{11}$, —$(CH_2)_{0-4}C(O)R_{11}$, —$(CH_2)_{0-4}NR_{11}R_{12}$, —$(CH_2)_{0-4}C(O)NR_{11}R_{12}$, —$(CH_2)_{0-4}N(R_{11})C(O)(R_{12})$, —$(CH_2)_{0-4}C(O)OR_{11}$, —$(CH_2)_{0-4}OC(O)R_{11}$, —$(CH_2)_{0-4}C(S)R_{11}$, —$(CH_2)_{0-4}S(O)_aR_{11}$, —$(CH_2)_{0-4}S(O)_bNR_{11}R_{12}$, —$(CH_2)_{0-4}N(R_{11})S(O)_bR_{12}$, where a is 0, 1, or 2, and b is 1 or 2.

$R_{11}$, $R_{12}$, and $R_{13}$ are independently chosen at each occurrence from hydrogen and a $C_1$-$C_6$aliphatic group; each of $R_{11}$, $R_{12}$, and $R_{13}$ is unsubstituted or substituted with one or more substituents independently chosen from halogen, hydroxyl, vinyl, allenyl, oxo, cyano, amino, —COOH, $C_1$-$C_6$alkyl, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy.

$R_3$ and $R_4$ are 0 or 1 or more substituents independently chosen from halogen, hydroxyl, amino, cyano, $C_1$-$C_4$alkyl, $C_1$-$C_4$alkoxy, $C_2$-$C_4$alkanoyl, (mono- and di-$C_1$-$C_4$alkylamino)$C_0$-$C_2$alkyl, $C_1$-$C_2$haloalkyl, and $C_1$-$C_2$haloalkoxy.

Within Formula I, when $R_1$ is ethyl,
The group

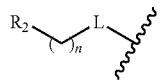

is not 4-methoxybenzyl-NHC(O)—, pyridin-2-ylmethyl-NHC(O)—, 3-(morpholin-1-yl)propyl-NHC(O)—, 3-(azepan-1-yl)propyl-NHC(O)—, 3-(azepan-1-yl)ethyl-NHC(O)—, 3-(pyrrolidin-1-yl)propyl-NHC(O)—, 3-(4-methylpiperazin-1-yl)propyl-NHC(O)—, 3-(piperidin-1-yl)propyl-NHC(O)—, di-isopropylaminopropyl-NHC(O)—, di-propylaminopropyl-NHC(O)—, di-butylaminopropyl-NHC(O)—, or 3-(butyl(ethyl)amino)propyl-NHC(O)—. The disclosure also provides pharmaceutical compositions comprising a compound of Formula I together with a pharmaceutically acceptable carrier.

The disclosure further provides a method of treating a disorder in which selective antagonism of the dopamine $D_2$ receptor provides effective relief comprising administering a therapeutically effective amount of a compound or salt of Formula I. In certain embodiment the disorder is Tourette's syndrome, bipolar disorder, tardive dyskinesia, Huntington's chorea, psychosis, depression, hyperprolactinemia, or schizophrenia.

DETAILED DESCRIPTION

Terminology

Figure 1A:
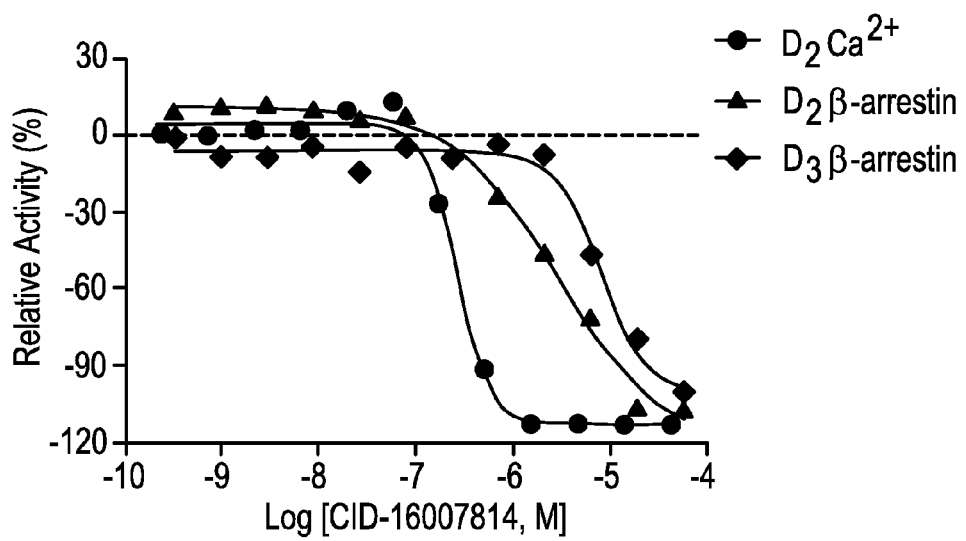
FIG. 1. (A) Graphical representation of the dose response curves of Compound 1 in $D_2$ $Ca^{2+}$ assay (circles, $AC_{50}$=0.281 µM), $D_2$β-arrestin assay (triangles, $AC_{50}$=2.89 µM), and $D_3$β-arrestin assay (diamonds, $AC_{50}$=5.76 µM). (B) Graphical representation of the dose response curves of 1 in binding assays for $D_1$ (squares), $D_2$ (circles, $K_i$=0.08 µM), $D_3$ (solid triangles, $K_i$=0.48 µM), $D_4$ (stars) and $D_5$ (inverted triangles).

Compounds of the present disclosure are generally described using standard nomenclature.

The terms "a" and "an" do not denote a limitation of quantity, but rather denote the presence of at least one of the referenced item. The term "or" means "and/or." The open-ended transitional phrase "comprising" encompasses the intermediate transitional phrase "consisting essentially of" and the close-ended phrase "consisting of." Claims reciting one of these three transitional phrases, or with an alternate transitional phrase such as "containing" or "including" can be written with any other transitional phrase unless clearly precluded by the context or art. Recitation of ranges of values are merely intended to serve as a shorthand method of referring individually to each separate value falling within the range, unless otherwise indicated herein, and each separate value is incorporated into the specification as if it were individually recited herein. The endpoints of all ranges are included within the range and independently combinable. All methods described herein can be performed in a suitable order unless otherwise indicated herein or otherwise clearly contradicted by context. The use of any and all examples, or exemplary language (e.g., "such as"), is intended merely to better illustrate the disclosure and does not pose a limitation on its scope unless otherwise claimed. No language in the specification should be construed as indicating any non-claimed element as essential to the practice of the invention as used herein. Unless defined otherwise, technical and scientific terms used herein have the same meaning as is commonly understood by one of skill in the art to which this disclosure belongs.

"Formula I" includes compounds and salts of certain subformulae, described herein such as compounds of Formula II to IV.

In certain situations, the compounds of Formula I may contain one or more asymmetric elements such as stereogenic centers, stereogenic axes and the like, e.g. asymmetric carbon atoms, so that the compounds can exist in different stereoisomeric forms. Formula I includes all stereoisomeric forms, including racemates, optically enriched, and optically pure forms. In addition, compounds with carbon-carbon double bonds may occur in Z- and E-forms, with all isomeric forms of the compounds being included in the present disclosure. In these situations, the single enantiomers, i.e., optically active forms can be obtained by asymmetric synthesis, synthesis from optically pure precursors, or by resolution of the racemates. Resolution of the racemates can also be accomplished, for example, by conventional methods such as crystallization in the presence of a resolving agent, or chromatography, using, for example a chiral HPLC column.

The disclosure of Formula I include all isotopes of atoms occurring in the present compounds. Isotopes include those atoms having the same atomic number but different mass numbers. By way of general example, and without limitation, isotopes of hydrogen include tritium and deuterium and isotopes of carbon include $^{11}C$, $^{13}C$ and $^{14}C$ and isotopes of fluorine including $^{19}F$.

Certain compounds are described herein using a general formula that includes variables, e.g. $R_1$-$R_4$, n, and L. Unless otherwise specified, each variable within such a formula is defined independently of other variables. Thus, if a group is said to be substituted, e.g. with 0-2 R*, then said group may be substituted with up to two R* groups and R* at each occurrence is selected independently from the definition of R*. When a group is substituted by an "oxo" substituent a carbonyl bond replaces two hydrogen atoms on a carbon. An "oxo" substituent on an aromatic group or heteroaromatic group destroys the aromatic character of that group, e.g. a pyridyl substituted with oxo is a pyridone.

Combinations of substituents and/or variables are permissible only if such combinations result in stable compounds. A stable compound or stable structure is meant to imply a compound that is sufficiently robust to survive isolation from a reaction mixture, and subsequent formulation into an effective therapeutic agent.

The term "substituted" means that any one or more hydrogen atoms bound to the designated atom or group is replaced with a selection from the indicated group, provided that the designated atom's normal valence is not exceeded. Unless otherwise specified substituents are named into the core structure. For example, it is to be understood that when (cycloalkyl)alkyl is listed as a possible substituent the point of attachment of this substituent to the core structure is in the alkyl portion.

Substituents are named into the ring unless otherwise indicated. A dash ("—") or a double bond ("═") that is not between two letters or symbols indicates the point of attachment for a substituent. For example, —$CONH_2$ is attached through the carbon atom.

An "aliphatic group" is a non-aromatic hydrocarbon group having the indicated number of carbon atoms. Aliphatic groups may be saturated, unsaturated, or cyclic.

"Alkyl" includes both branched and straight-chain saturated aliphatic hydrocarbon groups, having the specified number of carbon atoms. Thus, the term $C_1$-$C_6$alkyl includes alkyl groups having from 1 to about 6 carbon atoms. When $C_0$-$C_n$ alkyl is used herein in conjunction with another group, for example, (cycloalkyl)$C_0$-$C_2$ alkyl, the indicated group, in this case cycloalkyl, is either directly bound by a single covalent bond ($C_0$), or attached by an alkyl chain having the specified number of carbon atoms, in this case from 1 to about 2 carbon atoms. Examples of alkyl include, but are not limited to, methyl, ethyl, n-propyl, isopropyl, n-butyl, t-butyl, n-pentyl, and sec-pentyl. $C_1$-$C_6$alkyl includes alkyl groups have 1, 2, 3, 4, 5, or 6 carbon atoms.

"Alkoxy" is an alkyl group as defined above with the indicated number of carbon atoms attached through an oxygen bridge. Examples of alkoxy include, but are not limited to, methoxy, ethoxy, n-propoxy, i-propoxy, n-butoxy, 2-butoxy, t-butoxy, n-pentoxy, 2-pentoxy, 3-pentoxy, iso-pentoxy, neopentoxy, n-hexoxy, 2-hexoxy, 3-hexoxy, and 3-methylpentoxy.

"Alkylthio" indicates an alkyl group as defined above attached through a sulfur linkage, i.e. a group of the formula alkyl-S—. Examples include ethylthio and pentylthio.

"Alkanoyl" is an alkyl group as defined above with the indicated number of carbon atoms covalently bound to the group is substitutes through a carbonyl (C═O) bridge. The carbonyl carbon is included in the number of carbons, that is $C_2$alkanoyl is a $CH_3(C$═$O)$— group.

"Alkylester" is an alkyl group as defined herein covalently bound to the group it substitutes by an ester linkage. The ester linkage may be in either orientation, e.g., a group of the formula —O(C═O)alkyl or a group of the formula —(C═O)Oalkyl.

"Mono- and/or di-alkylamino" indicates secondary or tertiary alkyl amino groups, wherein the alkyl groups are as defined above and have the indicated number of carbon atoms. The point of attachment of the alkylamino group is on the nitrogen. Examples of mono- and di-alkylamino groups include ethylamino, dimethylamino, and methyl-propyl-amino. A "(mono- and/or di-alkylamino)$C_0$-$C_2$alkyl group is a mono and/or dialkylamino group as defined that is directly bound to the group it substitutes ($C_0$alkyl) or attached to the group it substitutes via a 1 to 2 carbon alkyl group linker.

A "carbocyclic group" is a monocyclic or bicyclic saturated, partially unsaturated, or aromatic ring system in which all ring atoms are carbon. Usually each ring of the carbocyclic group contains from 4-6 ring atoms and a bicyclic carbocyclic group contains from 7 to 10 ring atoms but some other number of ring atoms may be specified. Unless otherwise indicated, the carbocyclic group may be attached to the group it substitutes at any carbon atom that results in a stable structure. When indicated the carbocyclic rings described herein may be substituted at any carbon atom if the resulting compound is stable.

"Cycloalkyl" is a saturated hydrocarbon ring groups, having the specified number of carbon atoms, usually from 3 to 7 carbon atoms. Examples of cycloalkyl groups include cyclopropyl, cyclobutyl, cyclopentyl, or cyclohexyl as well as bridged or caged saturated ring groups such as norborane or adamantane. In the term "(cycloalkyl)alkyl," cycloalkyl and alkyl are as defined above, and the point of attachment in on the alkyl group.

"Haloalkyl" indicates both branched and straight-chain saturated aliphatic hydrocarbon groups having the specified number of carbon atoms, substituted with 1 or more halogen atoms, generally up to the maximum allowable number of halogen atoms. Examples of haloalkyl include, but are not limited to, trifluoromethyl, difluoromethyl, 2-fluoroethyl, and penta-fluoroethyl.

"Haloalkoxy" indicates a haloalkyl group as defined above attached through an oxygen bridge.

"Halo" or "halogen" as used herein refers to fluoro, chloro, bromo, or iodo.

"Pharmaceutical compositions" are compositions comprising at least one active agent, such as a compound or salt of Formula I and at least one other excipient. "Carriers" are any inactive materials, including excipients and diluents, which may be added to the pharmaceutical compositions including carriers and diluents. Pharmaceutical compositions meet the U.S. FDA's GMP (good manufacturing practice) standards for human or non-human drugs.

The term "heterocyclic group" indicates a monocyclic saturated, partially unsaturated, or aromatic ring containing from 1 to about 4 heteroatoms chosen from N, O, and S, with remaining ring atoms being carbon, or a bicyclic saturated, partially unsaturated, or aromatic heterocylic ring system containing at least 1 heteroatom in the two ring system chosen from N, O, and S and containing up to about 4 heteroatoms independently chosen from N, O, and S in each ring of the two ring system. Usually each ring of the heterocyclic group contains from 4-6 ring atoms but some other number of ring atoms may be specified. Unless otherwise indicated, the heterocyclic ring may be attached to its pendant group at any heteroatom or carbon atom that results in a stable structure. When indicated the heterocyclic rings described herein may be substituted on carbon or on a nitrogen atom if the resulting compound is stable. It is preferred that the total number of heteroatoms in a heterocyclic groups is not more than 4 and that the total number of S and O atoms in a heterocyclic group is not more than 2, more preferably not more than 1. Examples of heterocyclic groups include, pyridyl, indolyl, pyrimidinyl, pyridizinyl, pyrazinyl, imidazolyl, oxazolyl, furanyl, thiophenyl, thiazolyl, triazolyl, tetrazolyl, isoxazolyl, quinolinyl, pyrrolyl, pyrazolyl, benz[b]thiophenyl, isoquinolinyl, quinazolinyl, quinoxalinyl, thienyl, isoindolyl, dihydroisoindolyl, 5,6,7,8-tetrahydroisoquinoline, pyridinyl, pyrimidinyl, furanyl, thienyl, pyrrolyl, pyrazolyl, pyrrolidinyl, morpholinyl, piperazinyl, piperidinyl, and pyrrolidinyl.

Additional examples heterocyclic groups include, but are not limited to, phthalazinyl, oxazolyl, indolizinyl, indazolyl, benzothiazolyl, benzimidazolyl, benzofuranyl, benzoisoxolyl, dihydro-benzodioxinyl, oxadiazolyl, thiadiazolyl, triazolyl, tetrazolyl, oxazolopyridinyl, imidazopyridinyl, isothiazolyl, naphthyridinyl, cinnolinyl, carbazolyl, beta-carbolinyl, isochromanyl, chromanonyl, chromanyl, tetrahydroisoquinolinyl, isoindolinyl, isobenzotetrahydrofuranyl, isobenzotetrahydrothienyl, isobenzothienyl, benzoxazolyl, pyridopyridinyl, benzotetrahydrofuranyl, benzotetrahydrothienyl, purinyl, benzodioxolyl, triazinyl, phenoxazinyl, phenothiazinyl, 5 pteridinyl, benzothiazolyl, imidazopyridinyl, imidazothiazolyl, dihydrobenzisoxazinyl, benzisoxazinyl, benzoxazinyl, dihydrobenzisothiazinyl, benzopyranyl, benzothiopyranyl, coumarinyl, isocoumarinyl, chromanyl, tetrahydroquinolinyl, dihydroquinolinyl, dihydroquinolinonyl, dihydroisoquinolinonyl, dihydrocoumarinyl, dihydroisocoumarinyl, isoindolinonyl, benzodioxanyl, benzoxazolinonyl, pyrrolyl N-oxide, pyrirnidinyl N-oxide, pyridazinyl N-oxide, pyrazinyl N-oxide, quinolinyl N-oxide, indolyl N-oxide, indolinyl N oxide, isoquinolyl N-oxide, quinazolinyl N-oxide, quinoxalinyl N-oxide, phthalazinyl N-oxide, imidazolyl N-oxide, isoxazolyl N-oxide, oxazolyl N-oxide, thiazolyl N-oxide, indolizinyl N oxide, indazolyl N-oxide, benzothiazolyl N-oxide, benzimidazolyl N-oxide, pyrrolyl N-oxide, oxadiazolyl N-oxide, thiadiazolyl N-oxide, tetrazolyl N-oxide, benzothiopyranyl S-oxide, and benzothiopyranyl S,S-dioxide.

"Heteroaryl" is a stable monocyclic aromatic ring having the indicated number of ring atoms which contains from 1 to 3, or in some embodiments from 1 to 2, heteroatoms chosen from N, O, and S, with remaining ring atoms being carbon, or a stable bicyclic or tricyclic system containing at least one 5- to 7-membered aromatic ring which contains from 1 to 3, or in some embodiments from 1 to 2, heteroatoms chosen from N, O, and S, with remaining ring atoms being carbon. Monocyclic heteroaryl groups typically have from 5 to 7 ring atoms. In some embodiments bicyclic heteroaryl groups are 9- to 10-membered heteroaryl groups, that is, groups containing 9 or 10 ring atoms in which one 5- to 7-member aromatic ring is fused to a second aromatic or non-aromatic ring. When the total number of S and O atoms in the heteroaryl group exceeds 1, these heteroatoms are not adjacent to one another. It is preferred that the total number of S and O atoms in the heteroaryl group is not more than 2. It is particularly preferred that the total number of S and O atoms in the aromatic heterocycle is not more than 1. Examples of heteroaryl groups include, but are not limited to, oxazolyl, pyranyl, pyrazinyl, pyrazolopyrimidinyl, pyrazolyl, pyridizinyl, pyridyl, pyrimidinyl, pyrrolyl, quinolinyl, tetrazolyl, thiazolyl, thienylpyrazolyl, thiophenyl, triazolyl, benzo[d]oxazolyl, benzofuranyl, benzothiazolyl, benzothiophenyl, benzoxadiazolyl, dihydrobenzodioxynyl, furanyl, imidazolyl, indolyl, and isoxazolyl.

"Heterocycloalkyl" is a saturated ring group, having 1, 2, 3, or 4 heteroatoms independently chosen from N, S, and O, with remaining ring atoms being carbon. Monocyclic heterocycloalkyl groups typically have from 3 to about 8 ring atoms or from 4 to 6 ring atoms. Examples of heterocycloalkyl groups include morpholinyl, piperazinyl, piperidinyl, and pyrrolinyl.

"Pharmaceutically acceptable salts" includes derivatives of the disclosed compounds wherein the parent compound is modified by making non-toxic acid or base salts thereof, and further refers to pharmaceutically acceptable hydrates solvates of such compounds and such salts. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts and the quaternary ammonium salts of the parent compound formed, for example, from non-toxic inorganic or organic acids. For example, conventional non-toxic acid salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxylmaleic, phenylacetic, glutamic, benzoic, salicylic, mesylic, esylic, besylic, sulfanilic, 2-acetoxybenzoic, fumaric, toluenesulfonic, methanesulfonic, ethane disulfonic, oxalic, isethionic, HOOC—$(CH_2)_n$—COOH where n is 0-4, and the like. Lists of additional suitable salts may be found, e.g., in *Remington's Pharmaceutical Sciences*, 17th ed., Mack Publishing Company, Easton, Pa., p. 1418 (1985).

The term "carrier" applied to pharmaceutical compositions/combinations of the invention refers to a diluent, excipient, or vehicle with which an active compound is provided.

The term "therapeutically effective amount" of a compound of Formula I, or a related formula, means an amount effective, when administered to a human or non-human patient, to provide a therapeutic benefit such as an amelioration of symptoms, e.g., an amount effective to decrease the symptoms of a central nervous system disorder, and including an amount sufficient to reduce the symptoms of a schizophrenia; Parkinson's disease (PD); dyskinesia; restless legs syndrome; depression; or the cravings associated with substance abuse. Thus a therapeutically effective amount of a compound is also an amount sufficient significantly reduce the indicia of the disease or condition being treated. The invention also includes, in certain embodiments, using compounds of Formula I in prophylactic treatment and therapeutic treatment. In the context of prophylactic or preventative treatment a "therapeutically effective amount" is an amount sufficient to significantly decrease the treated patient's risk of exhibiting symptoms of the condition treated. A significant reduction is any detectable negative change that is statistically significant in a standard parametric test of statistical significance, such as Student's t-test, in which $p<0.05$.

Chemical Description

In addition to compounds and salts of Formula I disclosed in the SUMMARY section, the disclosure includes compounds and salts of Formula I

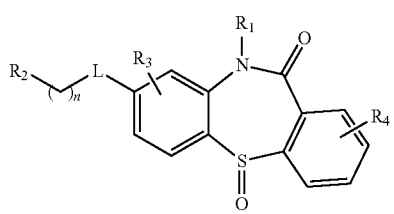

(Formula I)

In which any of the following conditions are met. Any of the following conditions can be combined so long as a stable compound results.

Formula II-IV, subformulae of Formula I, are included.

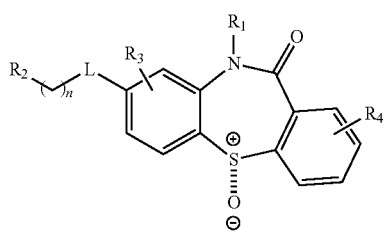

(Formula II)

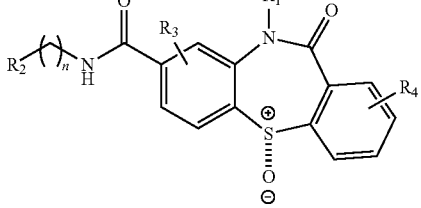

(Formula III)

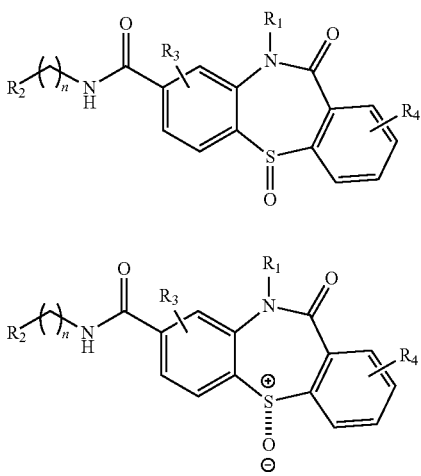

(Formula IV)

The variables, e.g., $R_1$-$R_4$ and n, may carry the values set forth in the Summary section or may carry any of the variables set forth below.

The disclosure includes embodiments in which $R_1$ carries any of the following values.

(i) $R_1$ is $C_1$-$C_6$alkyl, $C_2$-$C_6$alkenyl, or ($C_3$-$C_7$cycloalkyl) $C_0$-$C_2$alkyl.

(ii) $R_1$ is $C_1$-$C_6$alkyl.

(iii) $R_1$ is methyl or ethyl, and $R_3$ and $R_4$ are both 0 substituents.

The disclosure includes embodiments in which $R_3$ and $R_4$ are both 0, 1, or 2 substituents independently chosen from halogen, hydroxyl, amino, cyano, $C_1$-$C_2$alkyl, $C_1$-$C_2$alkoxy, trifluoromethyl, difluoromethoxy, and trifluoromethoxy.

The disclosure includes embodiments in which n is 1, 2, or 3 and

is unsubstituted or substituted with one $C_1$-$C_4$alkyl substituent or 1 trifluoromethyl substituent and in which n is 1 or 2 and

is unsubstituted or substituted with one methyl substituent

The disclosure includes embodiments in which $R_2$ carries any of the following values.

(i) $R_2$ is $C_3$-$C_7$cycloalkyl, 5- or 6-membered heterocycloalkyl containing 1 or 2 heteroatoms selected from N, O, or S, phenyl, naphthyl, phenyl fused to a 5- or 6-membered heterocyclic ring containing 1 or 2 oxygen atoms, pyridyl, pyrimidinyl, pyrazinyl, thienyl, furanyl, pyrrolyl, or imidazolyl, each of which $R_2$ is unsubstituted or substituted with one or more substituents independently chosen from halogen, hydroxyl, amino, cyano, $C_1$-$C_4$alkyl, $C_1$-$C_4$alkoxy, (mono- and di-$C_1$-$C_4$alkylamino)$C_0$-$C_2$alkyl, $C_1$-$C_4$alkylthio, $C_1$-$C_4$alkylsulfonyl, $C_1$-$C_2$haloalkyl, and $C_1$-$C_2$haloalkoxy.

(ii) $R_2$ is phenyl, naphthyl, benzo[d][1,3]dioxolyl, pyridyl, thienyl, furanyl, indolyl, imidazolyl, thiazolyl, pyrrolidinyl, piperidinyl, piperazinyl, pyrrolyl, morpholinyl, each which is substituted with one or more substituents independently chosen from halogen, hydroxyl, amino, cyano, $C_1$-$C_4$alkyl, $C_1$-$C_4$alkoxy, (mono- and di-$C_1$-$C_4$alkylamino)$C_0$-$C_2$alkyl, $C_1$-$C_4$alkylthio, $C_1$-$C_4$alkylsulfonyl, $C_1$-$C_2$haloalkyl, and $C_1$-$C_2$haloalkoxy.

(iii) $R_2$ is phenyl, naphthyl, benzo[d][1,3]dioxolyl, pyridyl, thienyl, pyrrolidinyl, piperidinyl, piperazinyl, each which is substituted with one or more substituents independently chosen from halogen, hydroxyl, cyano, $C_1$-$C_4$alkyl, $C_1$-$C_4$alkoxy, methylthio, methylsulfonyl, trifluoromethyl, and trifluoromethoxy.

The disclosure also includes compounds of Formula III or IV and salts thereof in which $R_1$ is $C_1$-$C_6$alkyl, benzyl, or ($C_3$-$C_7$cycloalkyl)$C_0$-$C_2$alkyl; $R_3$ and $R_4$ and both 0, 1, or 2 substituents independently chosen from halogen, hydroxyl, amino, cyano, $C_1$-$C_2$alkyl, $C_1$-$C_2$alkoxy, trifluoromethyl, difluoromethoxy, and trifluoromethoxy;

n is 1, 2, or 3 and

is unsubstituted or substituted with one $C_1$-$C_4$alkyl substituent or one trifluoromethyl substituent; and $R_2$ is phenyl, naphthyl, benzo[d][1,3]dioxolyl, pyridyl, thienyl, furanyl, indolyl, imidazolyl, thiazolyl, pyrrolidinyl, piperidinyl, piperazinyl, pyrrolyl, morpholinyl, each which is unsubstituted or substituted with one or more substituents independently chosen from halogen, hydroxyl, amino, cyano, $C_1$-$C_4$alkyl, $C_1$-$C_4$alkoxy, (mono- and di-$C_1$-$C_4$alkylamino)$C_0$-$C_2$alkyl, $C_1$-$C_4$alkylthio, $C_1$-$C_4$alkylsulfonyl, $C_1$-$C_2$haloalkyl, and $C_1$-$C_2$haloalkoxy.

The disclosure includes compounds of Formula III or IV and salts thereof, wherein $R_1$ is $C_1$-$C_4$alkyl;

$R_3$ and $R_4$ are both 0 substituents; n is 1, 2, or 3;

is unsubstituted or substituted with one methyl substituent; and

R$_2$ carries any of the definitions for R$_2$ set forth in this disclosure.

The disclosure includes compounds and salts of Formula V:

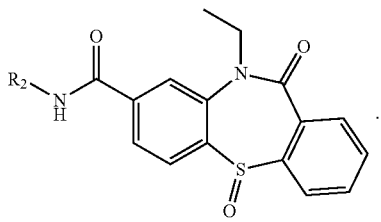

(V)

In Formula V, R$_2$ may carry any of the definitions set forth herein. In certain embodiments R$_2$ is benzyl, 1-phenethyl, phenylethyl, or benzo[d][1,3]dioxol-5-ylmethyl, each of which is unsubstituted or substituted with one or more substituents chosen from thiomethyl, halogen, cyano, C$_1$-C$_4$alkyl, C$_1$-C$_2$methoxy, C$_1$-C$_2$alkylsulfonyl, trifluoromethyl, or trifluoromethoxy.

The disclosure includes compounds and salts of Formula VI:

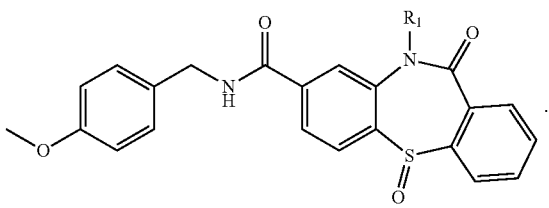

(VI)

In Formula VI, R$_1$ may carry any of the definitions set forth herein. In certain embodiments R$_1$ is methyl, ethyl, n-propyl, or benzyl.

The disclosure includes compounds and salts of Formula VII:

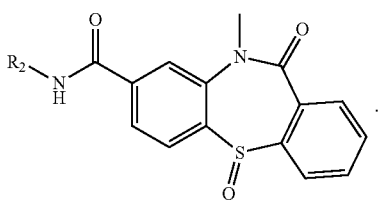

(VII)

In Formula VI, R$_2$ may carry any of the definitions set forth herein. In certain embodiments R$_2$ is phenyl, benzyl, pyridylmethyl, thienylethyl, pyrrolidinylethyl, piperidinylethyl, phenyl substituted with halogen or methoxy, or benzyl substituted with halogen or methoxy.

In certain embodiments directed to compounds of Formula III or Formula IV and the salts thereof, R$_2$ is thienyl, which is unsubstituted or substituted with one or more substituents independently chosen from halogen, C$_1$-C$_2$alkyl, or C$_1$-C$_2$alkoxy, or R$_2$ is phenyl which is unsubstituted or substituted with one or more substituents independently chosen from halogen, hydroxyl, amino, cyano, C$_1$-C$_4$alkyl, C$_1$-C$_4$alkoxy, (mono- and di-C$_1$-C$_4$alkylamino)C$_0$-C$_2$alkyl, C$_1$-C$_4$alkylthio, C$_1$-C$_4$alkylsulfonyl, C$_1$-C$_2$haloalkyl, and C$_1$-C$_2$haloalkoxy.

The disclosure includes compounds of Formula (VIII), (IX), and (X) and the pharmaceutically acceptable salts thereof.

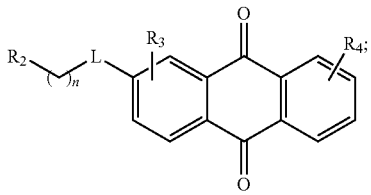

(VIII)

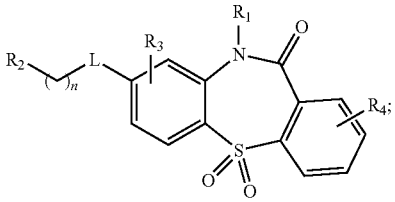

(IX)

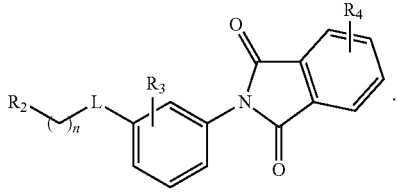

(X)

In Formulas (VIII), (IX), and (X) each of R$_1$, R$_2$, R$_3$, R$_4$, L, and n may carry any of the definitions set forth in this disclosure for these variables.

Pharmaceutical Preparations

Compounds disclosed herein can be administered as the neat chemical, but are preferably administered as a pharmaceutical composition. Accordingly, the disclosure provides pharmaceutical compositions comprising a compound or pharmaceutically acceptable salt of Formula I, together with at least one pharmaceutically acceptable carrier. The pharmaceutical composition/combination may contain a compound or salt of Formula I as the only active agent or may be combined with one or more additional active agents. In certain embodiments the pharmaceutical composition is in a dosage form that contains from about 0.1 mg to about 2000 mg, from about 10 mg to about 1000 mg, from about 100 mg to about 800 mg, or from about 200 mg to about 600 mg of a compound of Formula I.

Compounds disclosed herein may be administered orally, topically, parenterally, by inhalation or spray, sublingually, transdermally, via buccal administration, or by other means routine in the art for administering pharmaceutical compositions. The pharmaceutical composition may be formulated as any pharmaceutically useful form, e.g., as an aerosol, a cream, a gel, a pill, a capsule, a tablet, a syrup, a transdermal patch, or an ophthalmic solution. Some dosage forms, such as tablets and capsules, are subdivided into suitably sized unit doses containing appropriate quantities of the active components, e.g., an effective amount to achieve the desired purpose.

Carriers include excipients and diluents and must be of sufficiently high purity and sufficiently low toxicity to render them suitable for administration to the patient being treated. The carrier can be inert or it can possess pharmaceutical benefits of its own. The amount of carrier employed in conjunction with the compound is sufficient to provide a practical quantity of material for administration per unit dose of the compound.

Classes of carriers include, but are not limited to binders, buffering agents, coloring agents, diluents, disintegrants, emulsifiers, flavorants, glidants, lubricants, preservatives, stabilizers, surfactants, tableting agents, and wetting agents. Some carriers may be listed in more than one class, for example vegetable oil may be used as a lubricant in some formulations and a diluent in others. Exemplary pharmaceutically acceptable carriers include sugars, starches, celluloses, powdered tragacanth, malt, gelatin; talc, and vegetable oils. Optional active agents may be included in a pharmaceutical composition, which do not substantially interfere with the activity of the compound of the present invention.

The pharmaceutical compositions/combinations can be formulated for oral administration. These compositions contain between 0.1 and 99 weight % (wt. %) of a compound of Formula I and usually at least about 5 wt. % of a compound of Formula I. Some embodiments contain from about 25 wt. % to about 50 wt. % or from about 5 wt. % to about 75 wt. % of the compound of Formula I.

Methods of Treatment

The disclosure provides methods of treating central nervous system disorders, including Tourette's syndrome, bipolar disorder, tardive dyskinesia, hyperprolactinemia, Huntington's chorea, psychosis, depression, or schizophrenia comprising administering an effective amount of a compound of Formula I to a patient having one of these disorders.

A compound of Formula I may be the only active agent administered (monotherapy) or may be combined with one or more other active agents (combination, adjunct, or augmentation therapy).

In another embodiment the invention provides a method of treating depression comprising (i) diagnosing a patient as having depression and (ii) providing an effective amount of compound of Formula I to the patient, wherein the compound of Formula I is provided as the only active agent or is provided together with one or more additional active agents.

Psychosocial intervention may play an important role in treatment of any of central nervous system disorder. Psychosocial intervention includes cognitive-behavior therapy, dialectical-behavior therapy, interpersonal therapy, psychodynamic therapy, and group therapy.

In other embodiments, the effective amount of a compound of Formula I is an amount effective to decrease psychiatric symptoms. For example an effective amount of a compound of Formula I is an amount sufficient to decrease Tourette's symptoms or schizophrenia symptoms. Preferably the decrease in Tourette's symptoms or schizophrenia symptoms is a 50% or greater reduction of symptoms identified on symptom rating scale for these disorders. For example an effective amount may be an amount sufficient to decrease the patient's score on a psychiatric symptoms rating scale such as the Brief Psychiatric Rating Scale, the Clinical Global Impression, or the Positive and Negative Syndrome Scale.

EXAMPLES

Abbreviations
   AcOH Acetic acid
   CDI 1,1'-carbonyldiimidazole
   DMF Dimethylformamide
   DIPEA N,N-Diisopropylethylamine
   HATU O-(7-azabenzotriazol-1-yl)-N,N,N',N'-tetramethyluronium hexafluorophosphate
   THF tetrahydrofuran General Methods for Chemistry All solvents were of anhydrous quality purchased from Aldrich Chemical Co., and used as received. Commercially available starting materials and reagents were purchased from Aldrich, TCI and Acros and were used as received.

Analytical thin layer chromatography (TLC) was performed with Sigma Aldrich TLC plates (5×20 cm, 60 Å, 250 μm). Visualization was accomplished by irradiation under a 254 nm UV lamp. Chromatography on silica gel was performed using forced flow (liquid) of the indicated solvent system on Biotage KPSil pre-packed cartridges and using the Biotage SP-1 automated chromatography system. $^1$H NMR spectra were recorded on a Varian Inova 400 MHz spectrometer. Chemical shifts are reported in ppm with the solvent resonance as the internal standard (CDCl$_3$ 7.27 ppm, DMSO-d$_6$ 2.49 ppm, for $^1$H NMR). Data are reported as follows; chemical shift, multiplicity (s=singlet, d=doublet, t=triplet, q=quartet, sep=septet, quin=quintet, br=broad, m=multiplet), coupling constants, and number of protons.

Low resolution mass spectra (electrospray ionization) were acquired on an Agilent Technologies 6130 quadrupole spectrometer coupled to an Agilent Technologies 1200 series HPLC. The HPLC retention time were recorded through standard gradient 4% to 100% acetonitrile (0.05% TFA) over 7 minutes using Luna C$_{18}$ (3 μm, 3 mm×75 mm) column with a flow rate of 0.800 mL/min. High resolution mass spectral data were collected in-house using an Agilent 6210 time-of-flight mass spectrometer coupled to an Agilent Technologies 1200 series HPLC system. If needed, products were purified via a Waters preparative HPLC equipped with a Phenomenex Luna C$_{18}$ reverse phase (5 μm, 30 mm×75 mm) column having a flow rate of 45 mL/min. The mobile phase was a mixture of acetonitrile (0.1% TFA) and H$_2$O (0.1% TFA) for acidic condition and a mixture of acetonitrile and H$_2$O (0.1% NH$_4$OH) for basic condition.

Samples were analyzed for purity on an Agilent 1200 series LCMS equipped with a Luna C$_{18}$ reverse phase (3 μm, 3 mm×75 mm) column having a flow rate of 0.800 mL/min over a 7.0 minutes gradient and a run time of 8.5 minutes. Purity of final compounds was determined to be >95%, using a 3 μL injection with quantitation by AUC at 220 and 254 nm (Agilent diode array detector).

General Protocol A. A mixture of acid (0.095 mmol, 1.0 equiv.) and amine (0.19 mmol, 2 equiv.) in DMF (1.00 mL) was treated at room temperature with EDC (0.19 mmol, 2.0 equiv.) and DMAP (0.19 mmol, 2.0 equiv). The reaction mixture was stirred at room temperature for overnight. The crude material was purified by preparative HPLC to give the final product.

General Protocol B. A solution of acid (0.16 mmol, 1.0 equiv.) in DMF (2.00 mL) was treated at room temperature with HATU (0.32 mmol, 2.0 equiv.) and DIPEA (0.32 mmol, 2.0 equiv). The mixture was stirred at room temperature for 5 min, and then amine (0.32 mmol, 2.0 equiv.) was added. The reaction mixture was stirred at room temperature for overnight. The crude material was purified by preparative HPLC to give the final product.

Example 1

Primary HTS of Sytravon Library and Confirmatory Screen: $D_2$ $Ca^{2+}$ Screen Assay For the primary screen, a calcium accumulation assay was executed using a cell line which stably expressed the $D_2$ DAR under control of Tetracycline-Regulated Expression (HEK293 T-REx™), as well as chimeric G-protein ($G_{qi5}$) to allow coupling of the $D_2$ DAR to calcium release. In this system, $D_2$ DAR gene expression is induced by addition of Tet to the cells prior to the assay and intracellular $Ca^{2+}$ release was detected with a specific $Ca^{2+}$ fluorescent dye.

The resting concentration of calcium ions ($Ca^{2+}$) in the cells' cytoplasm is normally maintained in the range of 10-100 nM. To maintain this low concentration, $Ca^{2+}$ is actively pumped from the cytosol to the extracellular space and into the endoplasmic reticulum (ER), and sometimes into the mitochondria. Signaling occurs when the cell is stimulated to release $Ca^{2+}$ from intracellular stores. The most common signaling pathway that increases cytoplasmic calcium concentration is the phospholipase C (PLC) pathway. In the engineered cell line used for screening, dopamine stimulation of the $D_2$ DAR activates the chimeric $G_{qi5}$ G-protein, which in turn acts on PLC which hydrolyses the membrane phospholipid PIP2 to form inositol trisphosphate (IP3) and diacylglycerol (DAG). $IP_3$ diffuses to the ER, binds to its receptor (IP3 receptor), which is a $Ca^{2+}$ channel and, thus, releases $Ca^{2+}$ from the ER to the cytosol. To measure this cytosolic $Ca^{2+}$ accumulation, we used the Screen Quest™ Fluo-8 Calcium Assay Kit (AAT Bioquest, Sunnyvale, Calif.). Acetoxymethyl (AM) esters bound to Fluo-8™ dye are non-polar molecules that easily cross live cell membranes transporting the dye inside the cell, and are then rapidly hydrolyzed by cellular esterases inside live cells. As Fluo-8™ is freed from AM esters, it binds to $Ca^{2+}$ and emits a fluorescent signal at 514 nm that escalates with increasing cytosolic $Ca^{2±}$. To measure this calcium flux signal, we used the Functional Drug Screening System (FDSS) (Hamamatsu, Japan), a high throughput screening device that allows optical detection of signal transmissions within living cells in a time-resolving fashion.

The cells were plated in DMEM media with High Glucose (Gibco, #10564), 10% FBS, 1×NEAA, and Pen/Strep. 24 hr after thawing, selective antibiotics Hygromycin B (10 µg/mL), Puromycin (2 µg/mL) and Blasticidin (15 µg/mL) were added to the media for growing and passaging the cells. Cells were split and harvested for the experiment at ~90% confluence with TrypLE dissociation reagent and seeded at 2,100 cells, 3 µL/well in complete media without selective antibiotics with added Tet (1 µg/mL) using a MultiDrop Combi dispenser (Thermo Scientific, Logan, Utah) onto 1,536-well tissue culture treated, black-walled, clear bottom plates (Greiner Bio-One North America).

Quest Fluo-8™ calcium reagent was freshly prepared prior to adding to the cells (lyophilized Fluo-8™ dye provided with the kit was re-suspended in 200 µL DMSO as a 500× stock and stored at −20° C.). 2 µL/well of Quest Fluo-8™ calcium dye diluted in HBSS +10 mM HEPES buffer (for every 10 mL buffer, 1 mL of 10× quencher provided in the kit and 20 µL of 500×DMSO stock dye were added) was added to cells with a Multi-Drop Combi (ThermoScientific) and incubated for 45-90 min in the dark at ambient temperature. Then, the plates were introduced into the FDSS where they were pinned with 23 nL of test compound or dopamine controls and were read by FDSS in non-stimulated mode for 180 sec for detection of agonists. At that time point, 1 µL/well dopamine at 1 nM ($EC_{20}$) or 14 nM ($EC_{80}$) final concentration was added by the FDSS pipette head followed by 120 sec kinetic read for detection/recording of potentiators or antagonists stimulation.

Table 1 summarizes the protocol for the $Ca^{2+}$ assay.

TABLE 1

$Ca^{2+}$ Assay Protocol

| Sequence | Parameter | Value | Description |
|---|---|---|---|
| 1 | $D_2$ T-REx HEK293 | 3 µL | 2,100 cells/well in complete media with Tet |
| 2 | Time | 20-24 hr | Incubate at 30° C., 5% $CO_2$ |
| 3 | Reagent | 2 µL | Calcium dye (500×) with quencher (10×) in HBSS + 10 mM HEPES buffer |
| 4 | Time | 45-90 min | Room temp dark |
| 5 | Compound/Controls | 23 nL | Transfer libraries/dopamine controls: 10 mM as $EC_{100}$ & dose response 1:2 using FDSS pintool |
| 6 | Time | 180 kinetic | 37° C., FDSS fluorescent read |
| 7 | Ligand | 1 µL | Dopamine $EC_{20}$ (1 nM) or $EC_{80}$ (14 nM) |
| 8 | Time | 120 sec kinetic | 37° C., FDSS fluorescent read |

The cell line HEK293 $D_2$ T-REx™ used in the primary screen was also used to confirm activity of the active compounds selected from the primary qHTS and synthesized analogs on 1,536-well format following the same protocol as described above for the primary screen.

Example 2

$D_2$ Beta-Arrestin Functional Assay

For a secondary-screen and selectivity assays, DAR PathHunter® β-arrestin GPCR cell lines from DiscoveRx (Fremont, Calif.). In this) were used. In the $D_2$ Receptor PathHunter® β-arrestin GPCR cell line, the $D_2$ GPCR receptor (DAR) is overexpressed and fused with a small 42-amino acid fragment of β-galactosidase called ProLink™ on a CHO cellular background expressing a fusion protein of β-arrestin and a larger N-terminal deletion mutant of β-galactosidase ("enzyme acceptor"). When DAR is activated by dopamine, it stimulates binding of β-arrestin to the ProLink-tagged DAR and the two complementary parts of β-galactosidase form a functional enzyme. When substrate (PathHunter® Detection reagent) is added, β-galactosidase hydrolyzes it and generates a chemiluminescent signal.

D$_2$ Receptor PathHunter® β-arrestin cells were seeded at 2,100 cells/well in 3 μL/well media (DiscoveRx Plating Reagent 2) with MultiDrop Combi dispenser (Thermo Scientific, Logan, Utah) onto white tissue culture treated 1,536-well Aurora plates (Brooks Automation, Chelmsford, Mass.) and allowed to attach overnight at 37° C., 5% CO$_2$. Next, 23 nL/well of compound solutions in DMSO were added with a pintool transfer (Kalypsis, San Diego, Calif.). The cells were stimulated by compounds for 90 min at 37° C., 5% CO$_2$, after which 1.5 μL/well of DiscoveRx detection reagent was added with BioRAPTR FRD dispenser. The detection reagent was prepared by mixing of Galacton Star Substrate, Emerald II solution and PathHunter buffer (supplied by the assay kit) together at a 1:5:19 proportion just prior to dispensing. The plates were incubated at ambient temperature for 1 hr, and the luminescent signal was read on a ViewLux plate reader (PerkinElmer, Waltham, Mass.). Table 2 summarizes the protocol for the β-arrestin assay.

TABLE 2

Protocol for the β-Arrestin Assay

| Sequence | Parameter | Value | Description |
|---|---|---|---|
| 1 | Cells | 3 μL | 2,100 cells/well |
| 2 | Time | 16-20 hr | Incubate at 37° C. and 5% CO$_2$ |
| 3 | Ligand | 1 μL | 1.5 μM dopamine in HBSS + 10 mM HEPES + SMB |
| 4 | Reagent | 23 nL | Compound library, dopamine as control (in DMSO) |
| 5 | Time | 90 min | Incubate at 37° C. and 5% CO$_2$ |
| 6 | Detection Reagent | 1.5 μL | 1:5:19 Galacton Star Substrate:Emerald II solution:PathHunter buffer |
| 7 | Time | 60 min | Room temperature incubation |
| 8 | Detector | 30 sec | Luminescent settings, ViewLux plate reader |

Example 3

D$_2$ Binding Assay

Compounds were tested for differences in affinity between three dopamine receptor subtypes using radio-labeled ligand binding assays. The first assay determined the Ki value of the compounds for the D$_2$ DAR subtype using stable HEK cell lines expressing the D$_{2L}$ human dopamine receptors (Codex Biosciences, Gaithersburg, Md.). Cells were cultured in Dulbecco's modified Eagle's Medium containing 10% FBS, 1,000 units/mL Penicillin, 1,000 mg/mL Streptomycin, 100 mM Sodium Pyruvate, 1 μg/mL Gentamicin, and 250 mg/mL G418. All cells were maintained at 37° C. in 5% CO$_2$ and 90% humidity. For radioligand binding assays, cells were removed mechanically using calcium and magnesium-free Earle's Balanced Salt Solution (EBSS(−)). Intact cells were collected by centrifugation and then lysed with 5 mM Tris-HCl and 5 mM MgCl$_2$ at pH 7.4 in a glass homogenizer. Homogenates were centrifuged at 20,000×g for 30 minutes. The membranes were re-suspended in EBSS (pH 7.4) and protein concentration was determined using a Bradford assay according to the manufacturer's recommendations (Bio-Rad). Membranes were diluted to 24 mg/mL. It was determined in preliminary experiments that this protein concentration gave optimal binding with minimal ligand depletion. Membrane preparations were incubated for 90 min at room temperature with various concentrations of radioligand in a reaction volume of 250 μL EBSS containing 200 mM sodium metabisulfite. Non-specific binding was determined in the presence of 4 μM (+)-butaclamol. Bound ligand was separated from unbound by filtration through GF/C filters using a PerkinElmer cell harvester with ice cold EBSS (4 washes) and quantified on a Top-count (PerkinElmer) after addition of scintillation solution. Saturation experiments generated a $K_d$ value of 0.2 nM and a $B_{max}$ of ~4,200 fmol/mg for [$^3$H]-methylspiperone binding to D$_2$ receptors. In order to determine the affinity of a given compound for a receptor type, competition-binding assays were performed. For these assays the reaction mixture was incubated with a single concentration of radiolabeled ligand (0.2 nM [$^3$H]methylspiperone) and various concentrations of competing compound. Reactions were incubated, terminated, and quantified as indicated above. $K_i$ values of compounds were determined from observed IC$_{50}$ values using the Cheng-Prussoff equation.

The protocol for the D$_2$ Binding Assay is summarized in Table 3.

TABLE 3

D$_2$ Binding Assay Protocol

| Sequence | Parameter | Value | Description |
|---|---|---|---|
| 1 | Cells | 25 mL | 2 × 10$^7$ cells/flask |
| 2 | Time | 24 hr | Incubate at 37° C. and 5% CO$_2$ |
| 3 | Reagent | 10 mL | EBSS (−) |
| 4 | Time | 10 min | Room temperature |
| 5 | Centrifuge | 900 × g | Pellet cells |
| 6 | Lysis | 6 mL | Re-suspend and homogenize in lysis buffer |
| 7 | Centrifuge | 20,000 × g | Pellet homogenate |
| 8 | Buffer | 10 mL | Re-suspend in EBSS to appropriate protein concentration |
| 9 | Reagent | 25 μL | Buffer/Butaclamol/Test compound per assay tube |
| 10 | Reagent | 125 μL | Radioligand per assay tube |
| 11 | Lysate | 100 μL | Membrane preparation per assay tube |
| 12 | Time | 90 min | Incubate at room temperature with shaking |
| 13 | Filter | 4 washes | Filter membranes onto GF/C filter plates |
| 14 | Reagent | 50 μL | Perkin Elmer scintillation cocktail |
| 15 | Detector | Scintillation | Perkin Elmer - Top count |

Example 4

D₃ Beta-Arrestin Functional Assay

A D₃ PathHunter® β-arrestin cell line from DiscoveRx (Fremont, Calif.) was used to determine the functional selectivity of the compounds for $D_2$ versus $D_3$ receptor antagonism. A CHO cell line was engineered to overexpress $D_3$ dopamine receptor (DAR) and fused with a small 42-amino acid fragment of β-gal called ProLink™. In addition, these cells stably express a fusion protein of β-arrestin and a larger N-terminal deletion mutant of β-galactosidase ("enzyme acceptor"). When DAR is activated by dopamine, it stimulates binding of β-arrestin to ProLink-tagged DARs, and the two complementary parts of β-galactosidase form a functional enzyme. When substrate (PathHunter® Detection reagent) is added, βgalactosidase hydrolyzes it and generates a chemiluminescent signal.

For the 1,536-well assay, $D_3$ PathHunter® β-arrestin cells were seeded at 2,100 cells/well in 3 µL/well media (DiscoveRx Plating Reagent 2) with MultiDrop Combi dispenser (Thermo Scientific, Logan, Utah) onto white tissue culture treated 1,536-well Aurora plates (Brooks Automation, Chelmsford, Mass.) and allowed to attach overnight at 37° C., 5% $CO_2$. Next, 23 nL/well of compound solutions in DMSO were added with a pintool transfer (Kalypsis, San Diego, Calif.). The cells were stimulated by compounds for 90 minutes at 37° C., 5% $CO_2$, after which 1.5 µL/well of DiscoveRx detection reagent was added with BioRAPTR FRD dispenser. The detection reagent was prepared by mixing of Galacton Star Substrate, Emerald II solution, and PathHunter buffer (supplied by the assay kit) together at a 1:5:19 proportion just prior to dispensing. The plates were incubated at ambient temperature for 1 h, and the luminescent signal was read on ViewLux plate reader (PerkinElmer, Waltham, Mass.).

The $D_3$ β-arrestin assay protocol is summarized in Table 4.

TABLE 4

| Sequence | Parameter | Value | Description |
| --- | --- | --- | --- |
| 1 | Cells | 3 µL | 2,100 cells/well |
| 2 | Time | 16-20 hr | Incubate at 37° C. and 5% $CO_2$ |
| 3 | Ligand | 1 µL | 12.5 nM dopamine in HBSS + 10 mM HEPES + SMB |
| 4 | Reagent | 23 nL | Compound library, dopamine as control (in DMSO) |
| 5 | Time | 90 min | Incubate at 37° C. and 5% $CO_2$ |
| 6 | Detection Reagent | 1.5 µL | 1:5:19 Galacton Star Substrate:Emerald II solution:PathHunter buffer |
| 7 | Time | 60 min | Room temperature incubation |
| 8 | Detector | 30 sec | Luminescent settings, ViewLux plate reader |

Example 5

D₃ Binding Assay

Compounds were counter screened for affinity for the $D_3$ dopamine receptor. This was accomplished by determining the $K_i$ values for the compounds using stable (HEK293 based) cell lines expressing the $D_3$ human dopamine receptors (Codex Biosciences, Gaithersburg, Md.). Cells were cultured in Dulbecco's modified Eagle's Medium containing 10% FBS, 1,000 units/mL Penicillin, 1,000 mg/mL Streptomycin, 100 mM Sodium Pyruvate, 1 µg/mL Gentamicin, and 250 mg/mL G418. All cells were maintained at 37° C. in 5% $CO_2$ and 90% humidity. For radioligand binding assays, cells were removed mechanically using calcium and magnesium-free Earle's Balanced Salt Solution (EBSS(−)). Intact cells were collected by centrifugation and then lysed with 5 mM Tris-HCl and 5 mM $MgCl_2$ at pH 7.4 in a glass homogenizer. Homogenates were centrifuged at 20,000×g for 30 min. The membranes were re-suspended in EBSS (pH 7.4), and protein concentration was determined using a Bradford assay according to the manufacturer's recommendations (Bio-Rad). Membranes were diluted to 80 mg/mL, the predetermined optimal protein concentration for binding but minimal ligand depletion. Membrane preparations were incubated for 90 min at room temperature with various concentrations of radioligand in a reaction volume of 250 µL EBSS containing 200 mM sodium metabisulfite. Non-specific binding was determined in the presence of 4 µM (+)-Butaclamol. Bound ligand was separated from unbound by filtration through GF/C filters using a PerkinElmer cell harvester with ice cold EBSS (4 washes) and quantified on a Top-count (PerkinElmer) after addition of scintillation solution. Saturation experiments generated a $K_d$ value of 0.125 nM and a Bmax of ~600 fmol/mg for [³H]-methylspiperone binding to $D_3$ receptors. In order to determine the affinity of a given compound for a receptor type, competition-binding assays were performed. For these assays the reaction mixture was incubated with a single concentration of radiolabeled ligand (0.5 nM [³H]methylspiperone) and various concentrations of competing compound. Reactions were incubated, terminated, and quantified as indicated above. $K_i$ values of compounds were determined from observed $IC_{50}$ values using the Cheng-Prussoff equation.

The $D_3$ binding assay protocol is summarized in Table 5.

TABLE 5

| Sequence | Parameter | Value | Description |
| --- | --- | --- | --- |
| 1 | Cells | 25 mL | 2 × 10⁷ cells/flask |
| 2 | Time | 24 hr | Incubate at 37° C. and 5% $CO_2$ |
| 3 | Reagent | 10 mL | EBSS (−) |
| 4 | Time | 10 min | Room temperature |
| 5 | Centrifuge | 900 × g | Pellet cells |
| 6 | Lysis | 6 mL | Re-suspend and homogenize in lysis buffer |
| 7 | Centrifuge | 20,000 × g | Pellet homogenate |
| 8 | Buffer | 10 mL | Re-suspend in EBSS to appropriate protein concentration |
| 9 | Reagent | 25 µL | Buffer/Butaclamol/Test compound per assay tube |
| 10 | Reagent | 125 µL | Radioligand per assay tube |
| 11 | Lysate | 100 µL | Membrane preparation per assay tube |
| 12 | Time | 90 min | Incubate at room temperature with shaking |
| 13 | Filter | 4 washes | Filter membranes onto GF/C filter plates |

TABLE 5-continued

| Sequence | Parameter | Value | Description |
|---|---|---|---|
| 14 | Reagent | 50 µL | Perkin Elmer scintillation cocktail |
| 15 | Detector | Scintillation | Perkin Elmer - Top count |

Example 6

Synthesis of 10-methyl-11-oxo-n-(2-(thiophen-2-yl)ethyl)-10,11-dihydrodibenzo[b,f][1,4]thiazepine-8-carboxamide 5-(S)-oxide Synthetic Scheme

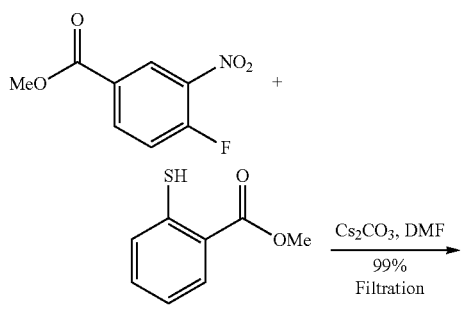

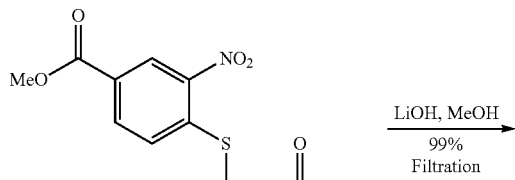

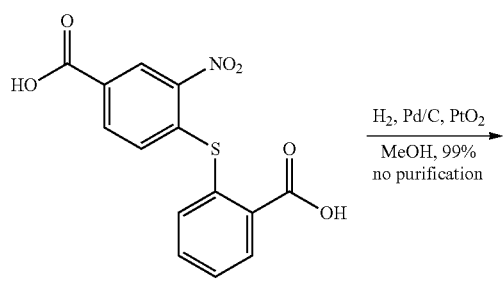

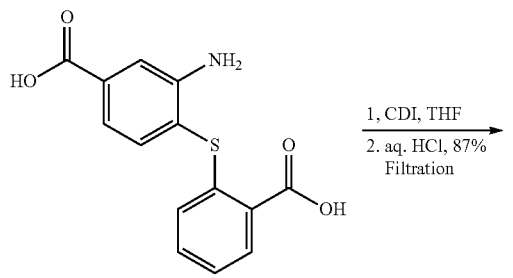

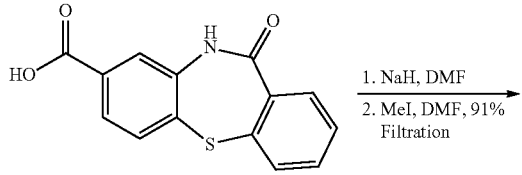

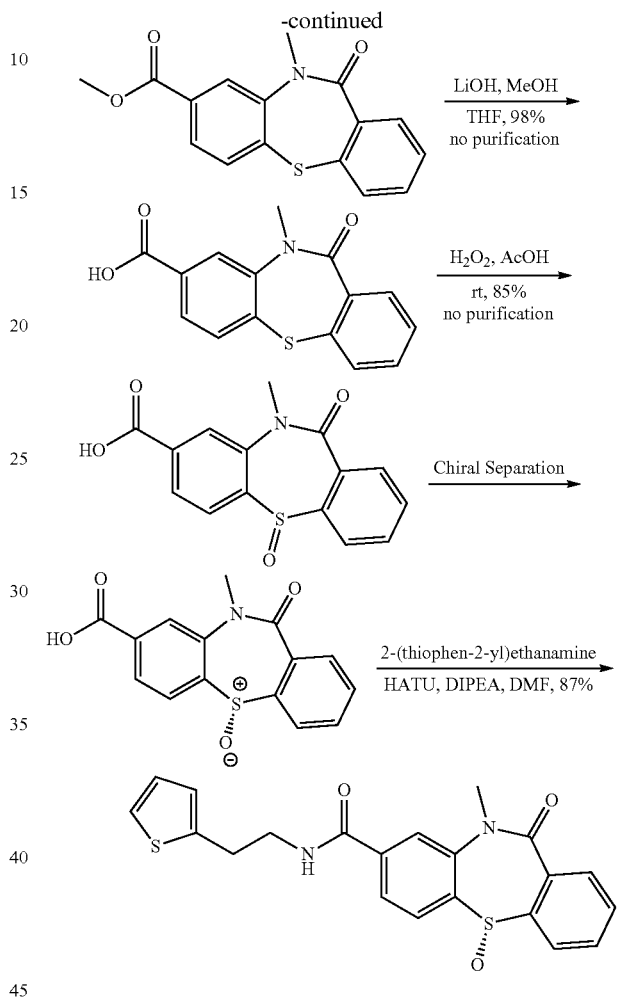

Step 1. Preparation of Methyl 4-(2-(methoxycarbonyl)phenylthio)-3-nitrobenzoate

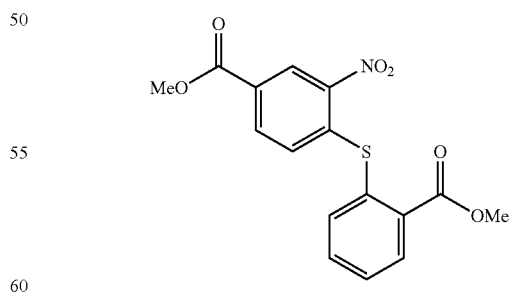

A solution of methyl 4-fluoro-3-nitrobenzoate (12.1 g, 60.9 mmol) and methyl 2-mercaptobenzoate (9.21 mL, 66.9 mmol) in DMF (6.00 mL) was treated with $Cs_2CO_3$ (19.8 g, 60.9 mmol) at room temperature. The reaction mixture was stirred at 40° C. for 4 hr and then cooled to room temperature. Ice water was added to induce the precipitation. The precipitate was filtered, washed with water, and dried to give 21.0 g (99%) of the title compound as a yellow solid which was used directly in the next reaction without further purification. $^1$H NMR (400 MHz, DMSO-$d_6$) δ ppm 8.63 (d, J=2.0 Hz, 1 H), 8.04 (dd, J=8.4, 1.8 Hz, 1 H), 7.87-7.99 (m, 1 H), 7.57-7.77 (m, 3 H), 7.05 (d, J=8.6 Hz, 1 H), 3.88 (s, 3 H), 3.71 (s, 3 H); LCMS RT=6.19 min, m/z 365.0 [M+Na$^+$]; HRMS (ESI) m/z calcd for $C_{16}H_{13}NNaO_6S$ [M+Na$^+$] 371.0387, found 371.0393.

Step 2. Preparation of 4-(2-Carboxyphenylthio)-3-nitrobenzoic acid

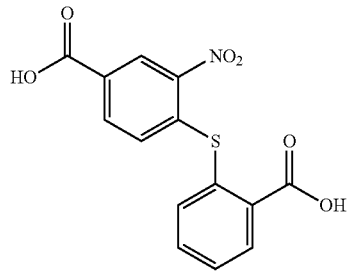 [SMILES: O=C(O)c1ccc(Sc2ccccc2C(=O)O)c([N+](=O)[O-])c1]

A solution of methyl 4-(2-(methoxycarbonyl)phenylthio)-3-nitrobenzoate (21.0 g, 60.5 mmol) in THF (150 mL) and water (150 mL) was treated at room temperature with LiOH (14.5 g, 605 mmol). The reaction mixture was stirred at 60° C. for 2 hr. The organic solvent was removed and the aqueous solution was washed with EtOAc and acidified with 2 N HCl until pH=~2. The yellow precipitate was filtered, washed with water, and dried to give 19.1 g (99%) of the title compound as a yellow solid which was used directly in the next reaction without further purification. $^1$H NMR (400 MHz, DMSO-$d_6$) δ ppm 13.53 (br. s., 1 H), 13.27 (br. s., 1 H), 8.58 (d, J=1.6 Hz, 1 H), 8.01 (dd, J=8.6, 2.0 Hz, 1 H), 7.85-7.95 (m, 1 H), 7.48-7.68 (m, 3 H), 7.07 (d, J=8.6 Hz, 1 H); LCMS RT=4.73 min, m/z 341.9 [M+Na$^+$]; HRMS (ESI) m/z calcd for $C_{14}H_9NNaO_6S$ [M+Na$^+$] 342.0043, found 342.0047.

Step 3. Preparation of 3-Amino-4-(2-carboxyphenylthio) benzoic acid

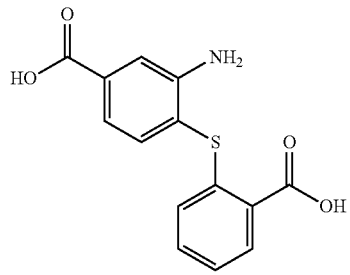 [SMILES: Nc1cc(C(=O)O)ccc1Sc1ccccc1C(=O)O]

A solution of 4-(2-carboxyphenylthio)-3-nitrobenzoic acid (8.70 g, 27.2 mmol) in MeOH (300 mL) was treated at room temperature with platinum (IV) oxide (300 mg, 1.32 mmol) and Pd/C (10%, 600 mg, 5.64 mmol). A balloon containing $H_2$ was connected to the flask and the reaction flask was repeatedly evacuated and refilled with $H_2$. After 16 hr, additional Pd/C (10%, 600 mg, 5.64 mmol) was added and the reaction mixture was stirred under $H_2$ balloon for an additional 32 hr. The reaction mixture was filtered through a pad of celite and concentrated to give 7.80 g (99%) of the title compound as a grey-yellow solid which was used directly in the next reaction without further purification. $^1$H NMR (400 MHz, DMSO-$d_6$) δ ppm 12.99 (br. s., 2 H), 7.92 (dd, J=7.8, 1.6 Hz, 1 H), 7.42 (d, J=1.6 Hz, 1 H), 7.37 (d, J=7.8 Hz, 1 H), 7.31-7.36 (m, 1 H), 7.18 (td, J=7.6, 1.2 Hz, 1 H), 7.13 (dd, J=8.0, 1.8 Hz, 1 H), 6.61 (dd, J=8.2, 0.8 Hz, 1 H), 5.40 (br. s., 2 H); LCMS RT=4.25 min, m/z 290.0 [M+H$^+$]; HRMS (ESI) m/z calcd for $C_{14}H_{12}NO_4S$ [M+H$^+$] 290.0482, found 290.0486.

Step 4. Preparation of 11-Oxo-10,11-dihydrodibenzo[b,f][1,4]thiazepine-8-carboxylic acid

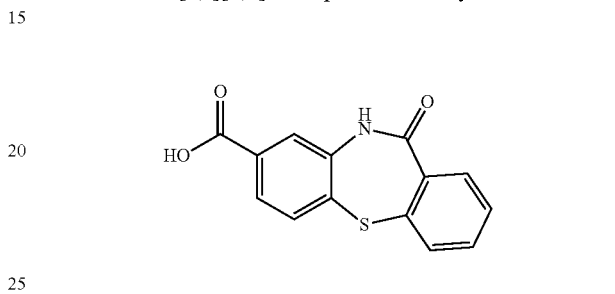

A solution of 3-amino-4-(2-carboxyphenylthio)benzoic acid (4.76 g, 16.5 mmol) in THF (100 mL) was treated at 0° C. with 1,1'-carbonyldiimidazole (CDI) (10.7 g, 65.8 mmol) via several portions. The reaction mixture was warmed to room temperature and stirred at room temperature overnight. The reaction mixture was poured into 140 mL of ice water containing concentrated HCl (20.0 mL) and stirred for 1 hr. The white precipitate was filtered, washed with water, and dried to give 3.89 g (87%) of the title compound as a white solid which was used directly in the next reaction without further purification. $^1$H NMR (400 MHz, DMSO-$d_6$) δ ppm 13.20 (br. s., 1 H), 10.79 (s, 1 H), 7.76 (d, J=1.2 Hz, 1 H), 7.62-7.70 (m, 3 H), 7.41-7.57 (m, 3 H); LCMS RT=4.55 min, m/z 271.9 [M+H$^+$]; HRMS (ESI) m/z calcd for $C_{14}H_{10}NO_3S$ [M+H$^+$] 272.0376, found 272.0376.

Step 5. Methyl 10-methyl-11-oxo-10,11-dihydrodibenzo[b,f][1,4]thiazepine-8-carboxylate

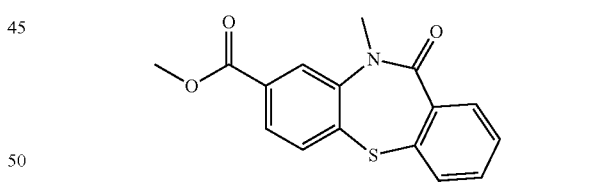

A solution of 11-oxo-10,11-dihydrodibenzo[b,f][1,4]thiazepine-8-carboxylic acid (200 mg, 0.74 mmol) in DMF (5.00 mL) was treated at 0° C. with NaH (295 mg, 7.37 mmol). The reaction mixture was warmed to room temperature and stirred at room temperature for 1 hr. Then, a solution of methyl iodide (0.46 mL, 7.37 mmol) in DMF (2.00 mL) was added dropwise to the mixture. The reaction mixture was stirred at room temperature for 1.5 hr. Water was carefully added and the aqueous layer was washed with EtOAc. The aqueous layer was acidified with HCl to induce the precipitation which was filtered, washed, and dried to give 200 mg (91%) of the title compound as a yellow solid which was used directly in the next reaction without further purification. $^1$H NMR (400 MHz, DMSO-$d_6$) δ ppm 8.00 (d, J=1.2 Hz, 1 H), 7.68-7.79 (m, 2 H), 7.59-7.66 (m, 1 H), 7.47-7.54 (m, 1 H), 7.37-7.45 (m, 2 H), 3.83 (s, 3 H), 3.52 (s, 3 H); LCMS RT=5.59 min, m/z 300.0 [M+H$^+$]; HRMS (ESI) m/z calcd for $C_{16}H_{14}NO_3S$ [M+H$^+$] 300.0689, found 300.0693.

Step 6. Preparation of 10-Methyl-11-oxo-10,11-dihydrodibenzo[b,f][1,4]thiazepine-8-carboxylic acid

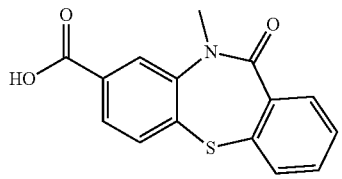 [SMILES: CN1C(=O)c2ccccc2Sc2ccc(C(=O)O)cc21]

A solution of methyl 10-methyl-11-oxo-10,11-dihydrodibenzo[b,f][1,4]thiazepine-8-carboxylate (150 mg, 0.50 mmol) in THF (3.00 mL), MeOH (1.50 mL) and water (0.50 mL) was treated at room temperature with LiOH (120 mg, 5.01 mmol). The reaction mixture was stirred at room temperature for 1 hr, diluted with water, and acidified with HCl. The aqueous mixture was extracted with 20% of MeOH in dichloromethane. The organic layer was separated, dried and concentrated to give 140 mg (98%) of the title compound as a grey solid which was used directly in the next reaction without further purification. $^1$H NMR (400 MHz, DMSO-d$_6$) δ ppm 13.31 (br. s., 1 H), 7.98 (d, J=1.2 Hz, 1 H), 7.67-7.76 (m, 2 H), 7.59-7.66 (m, 1 H), 7.47-7.54 (m, 1 H), 7.35-7.45 (m, 2 H), 3.52 (s, 3 H); LCMS RT=4.76 min, m/z 286.0 [M+H$^+$]; HRMS (ESI) m/z calcd for $C_{15}H_{12}NO_3S$ [M+H$^+$] 286.0532, found 286.0536.

Step 7. Preparation of 10-Methyl-11-oxo-10,11-dihydrodibenzo[b,f][1,4]thiazepine-8-carboxylic acid 5-oxide

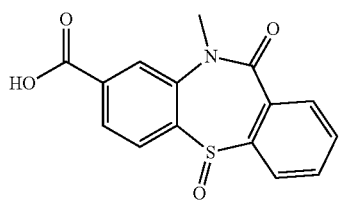 [SMILES: CN1C(=O)c2ccccc2S(=O)c2ccc(C(=O)O)cc21]

A suspension of 10-methyl-11-oxo-10,11-dihydrodibenzo[b,f][1,4]thiazepine-8-carboxylic acid (660 mg, 2.31 mmol) in acetic acid (18.8 mL) was treated at room temperature with H$_2$O$_2$ (5.91 mL, 30%, 57.8 mmol) for 8 hr. Upon completion, the reaction mixture was poured into a cold saturated solution of Na$_2$S$_2$O$_3$ in water and stirred at room temperature for 3 hr. The mixture was then extracted with 20% of MeOH in dichloromethane. The organic layer was separated, dried, and concentrated to give 595 mg (85%) of the title compound as a white solid containing ~5% of dioxide as a by-product. $^1$H NMR (400 MHz, DMSO-d$_6$) δ ppm 8.00 (d, J=1.2 Hz, 1 H), 7.96 (dd, J=8.2, 1.6 Hz, 1 H), 7.62-7.76 (m, 4 H), 7.52-7.59 (m, 1 H), 3.53 (s, 3 H); LCMS RT=4.02 min, m/z 302.0 [M+H$^+$]; HRMS (ESI) m/z calcd for $C_{15}H_{12}NO_4S$ [M+H$^+$] 302.0482, found 302.0486.

Step 8. 10-Methyl-11-oxo-10,11-dihydrodibenzo[b,f][1,4]thiazepine-8-carboxylic acid 5-(S)-oxide

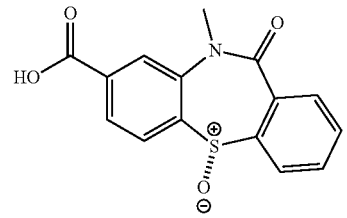 [SMILES: CN1C(=O)c2ccccc2[S@+]([O-])c2ccc(C(=O)O)cc21]

The title enantiomerically pure compound was purified to >98% purity using supercritical fluid chromatography (SFC) preparative systems at Lotus Separations, LLC (Princeton, N.J., USA). For preparative separation, an IC (2×15 cm) column was used with an eluent of 40% methanol (0.1% DEA)/CO$_2$, 100 bar. Flow rate was 60 mL/min and detection wavelength was 220 nm. For analytical separation, an IC (15×0.46 cm) column was used with an eluent of 40% methanol/CO$_2$, 100 bar. Flow rate was 3 mL/min and detection wavelengths were 220 and 280 nm. Retention time was 3.42 min. Retention time for R-configuration enantiomer was 2.40 min. The material was used directly in the next coupling reaction.

Step 9. Preparation of 10-Methyl-11-oxo-N-(2-(thiophen-2-yl)ethyl)-10,11-dihydrodibenzo[b,f][1,4]thiazepine-8-carboxamide 5-(S)-oxide (Compound 55)

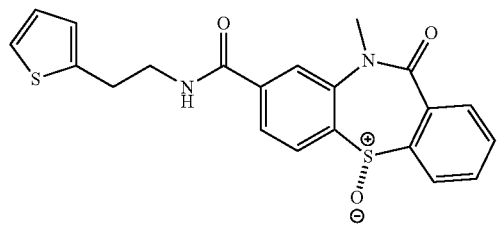 [SMILES: CN1C(=O)c2ccccc2[S@+]([O-])c2ccc(C(=O)NCCc3cccs3)cc21]

A solution of 10-methyl-11-oxo-10,11-dihydrodibenzo[b,f][1,4]thiazepine-8-carboxylic acid 5-(S)-oxide (100 mg, 0.332 mmol) in DMF (5.00 mL) was treated at room temperature with HATU (139 mg, 0.365 mmol) and diisopropylethylamine (0.174 mL, 0.996 mmol) followed by 2-(thiophen-2-yl)ethanamine (84.0 mg, 0.664 mmol). The reaction mixture was stirred at room temperature for 3 h and poured into ice water. The white precipitate was filtered and dried to give a white solid, which was purified via silica gel chromatography using a gradient of 10-100% of EtOAc in hexanes to give 118 mg (87%) of the title compound as a white solid.

LC-MS Retention Time: t$_1$ (Method 1)=5.348 min; t$_2$ (Method 2)=3.188 min; $^1$H NMR (400 MHz, DMSO-d$_6$) δ ppm 8.76 (t, J=5.7 Hz, 1 H), 7.94 (d, J=2.0 Hz, 1 H), 7.86 (dd, J=8.2, 2.0 Hz, 1 H), 7.69-7.77 (m, 2 H), 7.67 (d, J=8.2 Hz, 2 H), 7.51-7.60 (m, 1 H), 7.31 (dd, J=5.1, 1.2 Hz, 1 H), 6.92 (dd, J=5.1, 3.1 Hz, 1 H), 6.83-6.90 (m, 1 H), 3.55 (s, 3 H), 3.43-3.52 (m, 2 H), 3.02 (t, J=7.0 Hz, 2 H); $^{13}$C NMR (400 MHz, DMSO-d$_6$) δ ppm 13C NMR (101 MHz, DMSO-d$_6$) δ ppm 165.16, 165.10, 147.66, 145.98, 141.75, 137.87, 137.02, 132.92, 131.69, 131.23, 128.20, 127.39, 126.51, 125.70, 124.57, 124.43, 121.05, 119.40, 41.55, 38.03, 29.49; HRMS (ESI) m/z (M+H)$^+$ calcd. for $C_{21}H_{19}N_2O_3S_2$ [M+H$^+$] 411.0832, found 411.0831.

Example 7

10-Ethyl-N-(4-methoxybenzyl)-11-oxo-10,11-dihydrodibenzo[b,f][1,4]thiazepine-8-carboxamide 5-oxide (Compound 1)

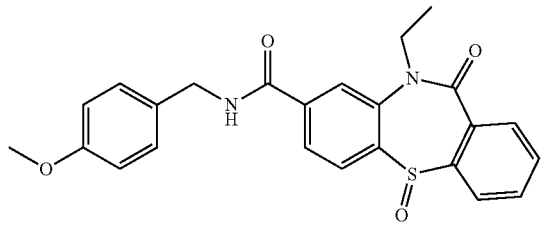 [SMILES: CCN1C(=O)c2ccccc2S(=O)c2ccc(C(=O)NCc3ccc(OC)cc3)cc21]

The title compound was prepared according to the general protocol A. $^1$H NMR (400 MHz, DMSO-$d_6$) δ ppm 9.08 (t, J=6.0 Hz, 1 H), 8.00 (d, J=1.4 Hz, 1 H), 7.92 (dd, J=8.1, 1.7 Hz, 1 H), 7.60-7.78 (m, 4 H), 7.55 (ddd, J=7.9, 7.0, 1.4 Hz, 1 H), 7.16-7.25 (m, 2 H), 6.81-6.88 (m, 2 H), 4.56 (dq, J=14.0, 7.1 Hz, 1 H), 4.26-4.45 (m, 2 H), 3.70-3.80 (m, 1 H), 3.69 (s, 3 H), 1.18 (t, J=7.1 Hz, 3 H); LCMS RT=5.22 min, m/z 435.1 [M+H$^+$]; HRMS (ESI) m/z calcd for $C_{24}H_{23}N_2O_4S$ [M+H$^+$] 435.1373, found 435.1371.

Example 8

10-Ethyl-N-(3-methoxybenzyl)-11-oxo-10,11-dihydrodibenzo[b,f][1,4]thiazepine-8-carboxamide 5-oxide (Compound 2)

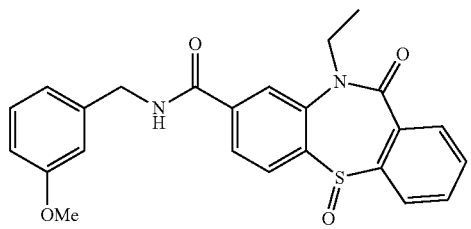 [SMILES: CCN1C(=O)c2ccccc2S(=O)c2ccc(C(=O)NCc3cccc(OC)c3)cc21]

The title compound was prepared according to the general protocol B. $^1$H NMR (400 MHz, DMSO-$d_6$) δ ppm 9.13 (t, J=5.8 Hz, 1 H), 8.01 (d, J=1.4 Hz, 1 H), 7.93 (dd, J=8.2, 1.6 Hz, 1 H), 7.66-7.74 (m, 3 H), 7.60-7.65 (m, 1 H), 7.55 (ddd, J=7.9, 7.0, 1.4 Hz, 1 H), 7.20 (t, J=8.0 Hz, 1 H), 6.81-6.89 (m, 2 H), 6.78 (ddd, J=8.3, 2.4, 0.9 Hz, 1 H), 4.49-4.62 (m, J=13.9, 7.1, 7.1, 7.0 Hz, 1 H), 4.32-4.48 (m, 2 H), 3.71-3.80 (m, 1 H), 3.69 (s, 3 H), 1.18 (t, J=7.0 Hz, 3 H); LCMS RT=5.26 min, m/z 435.1 [M+H$^+$]; HRMS (ESI) m/z calcd for $C_{24}H_{23}N_2O_4S$ [M+H$^+$] 435.1373, found 435.1379.

Example 9

10-Ethyl-N-(2-methoxybenzyl)-11-oxo-10,11-dihydrodibenzo[b,f][1,4]thiazepine-8-carboxamide 5-oxide (Compound 3)

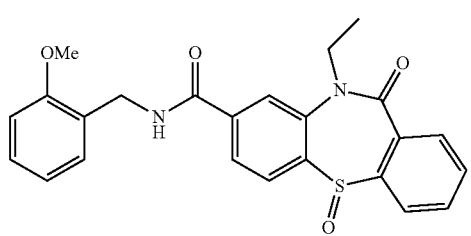 [SMILES: CCN1C(=O)c2ccccc2S(=O)c2ccc(C(=O)NCc3ccccc3OC)cc21]

The title compound was prepared according to the general protocol A. $^1$H NMR (400 MHz, DMSO-$d_6$) δ ppm 8.97 (t, J=5.8 Hz, 1 H), 8.03 (d, J=1.6 Hz, 1 H), 7.94 (dd, J=8.2, 1.6 Hz, 1 H), 7.66-7.74 (m, 3 H), 7.60-7.66 (m, 1 H), 7.55 (ddd, J=7.9, 7.0, 1.4 Hz, 1 H), 7.18-7.25 (m, 1 H), 7.15 (dd, J=7.5, 1.7 Hz, 1 H), 6.93-6.99 (m, 1 H), 6.85 (td, J=7.4, 1.0 Hz, 1 H), 4.56 (dq, J=13.9, 7.1 Hz, 1 H), 4.31-4.48 (m, 2 H), 3.79 (s, 3 H), 3.71-3.78 (m, 1 H), 1.18 (t, J=7.0 Hz, 3 H); LCMS RT=5.35 min, m/z 435.1 [M+H$^+$]; HRMS (ESI) m/z calcd for $C_{24}H_{23}N_2O_4S$ [M+H$^+$] 435.1373, found 435.1373.

Example 10

N-Benzyl-10-ethyl-11-oxo-10,11-dihydrodibenzo[b,f][1,4]thiazepine-8-carboxamide 5-oxide (Compound 4)

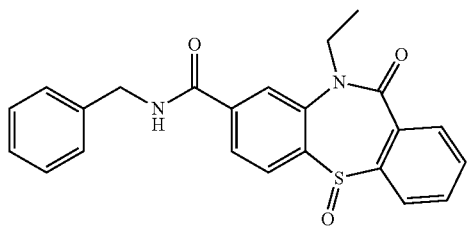 [SMILES: CCN1C(=O)c2ccccc2S(=O)c2ccc(C(=O)NCc3ccccc3)cc21]

The title compound was prepared according to the general protocol B. LCMS RT=5.24 min, m/z 405.1 [M+H$^+$]; HRMS (ESI) m/z calcd for $C_{23}H_{21}N_2O_3S$ [M+H$^+$] 405.1267, found 405.1268.

Example 11

N-Benzyl-10-ethyl-11-oxo-10,11-dihydrodibenzo[b,f][1,4]thiazepine-8-carboxamide 5-oxide (Compound 4)

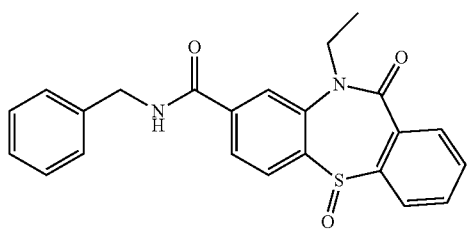 [SMILES: CCN1C(=O)c2ccccc2S(=O)c2ccc(C(=O)NCc3ccccc3)cc21]

Alternate procedure. The title compound was prepared according to the general protocol A. $^1$H NMR (400 MHz, DMSO-$d_6$) δ ppm 9.15 (t, J=5.9 Hz, 1 H), 8.02 (d, J=1.4 Hz, 1 H), 7.93 (dd, J=8.2, 1.6 Hz, 1 H), 7.65-7.73 (m, 3 H), 7.59-7.65 (m, 1 H), 7.55 (ddd, J=7.9, 6.9, 1.5 Hz, 1 H), 7.25-7.34 (m, 4 H), 7.16-7.25 (m, 1 H), 4.56 (sxt, J=6.9 Hz, 1 H), 4.34-4.51 (m, 2 H), 3.75 (sxt, J=7.0 Hz, 1 H), 1.18 (t, J=7.1 Hz, 3 H); LCMS RT=5.23 min, m/z 405.1 [M+H$^+$]; HRMS (ESI) m/z calcd for $C_{23}H_{21}N_2O_3S$ [M+H$^+$] 405.1267, found 405.1270.

Example 12

10-Ethyl-11-oxo-N-(1-phenylethyl)-10,11-dihydrodibenzo[b,f][1,4]thiazepine-8-carboxamide 5-oxide (Compound 5)

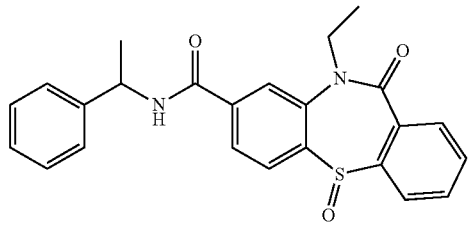 [SMILES: CCN1C(=O)c2ccccc2S(=O)c2ccc(C(=O)NC(C)c3ccccc3)cc21]

The title compound was prepared according to the general protocol A. $^1$H NMR (400 MHz, DMSO-d$_6$) δ ppm 8.91 (d, J=8.0 Hz, 0.5 H), 8.90 (d, J=8.0 Hz, 0.5 H), 8.00 (dd, J=7.2, 1.4 Hz, 1 H), 7.86-7.97 (m, 1 H), 7.60-7.77 (m, 4 H), 7.50-7.59 (m, 1 H), 7.24-7.39 (m, 4 H), 7.13-7.23 (m, 1 H), 5.10 (quin, J=7.5 Hz, 1 H), 4.44-4.72 (m, 1 H), 3.65-3.88 (m, 1 H), 1.44 (d, J=7.0 Hz, 1.5 H), 1.43 (d, J=7.0 Hz, 1.5 H), 1.18 (d, J=7.1 Hz, 1.5 H), 1.18 (d, J=7.1 Hz, 1.5 H); LCMS RT=5.44 min, m/z 419.1 [M+H$^+$]; HRMS (ESI) m/z calcd for C$_{24}$H$_{23}$N$_2$O$_3$S [M+H$^+$] 419.1424, found 419.1428.

Example 13

10-Ethyl-N-(4-(methylthio)benzyl)-11-oxo-10,11-dihydrodibenzo[b,f][1,4]thiazepine-8-carboxamide 5-oxide (Compound 6)

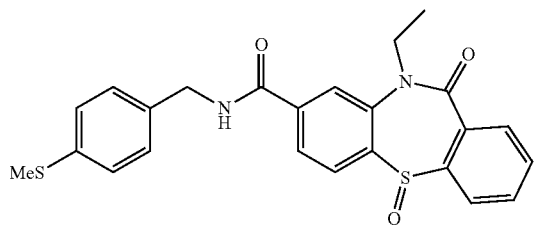 [SMILES: CCN1C(=O)c2ccccc2S(=O)c2ccc(C(=O)NCc3ccc(SC)cc3)cc21]

The title compound was prepared according to the general protocol A. $^1$H NMR (400 MHz, DMSO-d$_6$) δ ppm 9.12 (t, J=6.0 Hz, 1 H), 7.99 (d, J=1.4 Hz, 1 H), 7.91 (dd, J=8.2, 1.4 Hz, 1 H), 7.65-7.72 (m, 3 H), 7.59-7.65 (m, 1 H), 7.54 (td, J=7.3, 1.2 Hz, 1 H), 7.12-7.26 (m, 4 H), 4.55 (dq, J=14.1, 7.1 Hz, 1 H), 4.29-4.46 (m, 2 H), 3.73 (dq, J=13.9, 7.0 Hz, 1 H), 2.41 (s, 3 H), 1.17 (t, J=7.1 Hz, 3 H); LCMS RT=5.58 min, m/z 451.1 [M+H$^+$]; HRMS (ESI) m/z calcd for C$_{24}$H$_{23}$N$_2$O$_3$S$_2$ [M+H$^+$] 451.1145, found 451.1138.

Example 14

N-(4-tert-Butylbenzyl)-10-ethyl-11-oxo-10,11-dihydrodibenzo[b,f][1,4]thiazepine-8-carboxamide 5-oxide (Compound 7)

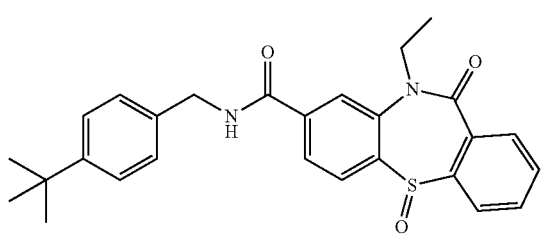 [SMILES: CCN1C(=O)c2ccccc2S(=O)c2ccc(C(=O)NCc3ccc(C(C)(C)C)cc3)cc21]

The title compound was prepared according to the general protocol B. $^1$H NMR (400 MHz, DMSO-d$_6$) δ ppm 9.09 (t, J=5.9 Hz, 1 H), 8.00 (d, J=1.4 Hz, 1 H), 7.91 (dd, J=8.1, 1.1 Hz, 1 H), 7.64-7.73 (m, 3 H), 7.60-7.64 (m, 1 H), 7.54 (td, J=7.4, 1.3 Hz, 1 H), 7.25-7.33 (m, 2 H), 7.19 (d, J=8.2 Hz, 2 H), 4.48-4.62 (m, 1 H), 4.31-4.46 (m, 2 H), 3.73 (dq, J=13.9, 6.9 Hz, 1 H), 1.22 (s, 9 H), 1.17 (t, J=7.1 Hz, 3 H); LCMS RT=6.25 min, m/z 461.2 [M+H$^+$]; HRMS (ESI) m/z calcd for C$_{27}$H$_{29}$N$_2$O$_3$S [M+H$^+$] 461.1893, found 461.1889.

Example 15

10-Ethyl-N-(4-methylbenzyl)-11-oxo-10,11-dihydrodibenzo[b,f][1,4]thiazepine-8-carboxamide 5-oxide (Compound 8)

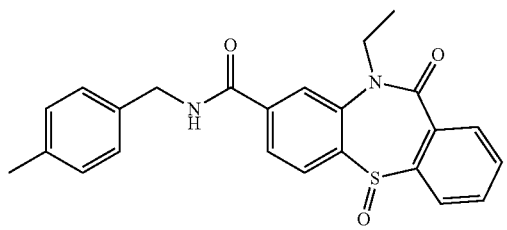 [SMILES: CCN1C(=O)c2ccccc2S(=O)c2ccc(C(=O)NCc3ccc(C)cc3)cc21]

The title compound was prepared according to the general protocol B. LCMS RT=5.53 min, m/z 419.1 [M+H$^+$]; HRMS (ESI) m/z calcd for C$_{24}$H$_{23}$N$_2$O$_3$S [M+H$^+$] 419.1424, found 419.1423.

Example 16

10-Ethyl-11-oxo-N-(4-(trifluoromethyl)benzyl)-10,11-dihydrodibenzo[b,f][1,4]thiazepine-8-carboxamide 5-oxide (Compound 9)

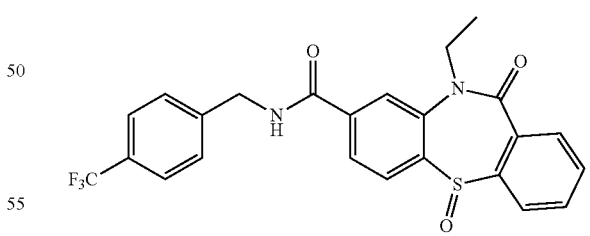

The title compound was prepared according to the general protocol A. $^1$H NMR (400 MHz, DMSO-d$_6$) δ ppm 9.25 (t, J=6.1 Hz, 1 H), 8.03 (d, J=1.6 Hz, 1 H), 7.94 (dd, J=8.2, 1.6 Hz, 1 H), 7.67-7.73 (m, 3 H), 7.61-7.67 (m, 3 H), 7.55 (ddd, J=7.9, 7.0, 1.5 Hz, 1 H), 7.50 (d, J=7.8 Hz, 2 H), 4.37-4.68 (m, 3 H), 3.63-3.86 (m, 1 H), 1.18 (t, J=7.1 Hz, 3 H); $^{19}$F NMR (376 MHz, DMSO-d$_6$) δ ppm −60.84 (s, 3 F); LCMS RT=5.81 min, m/z 473.1 [M+H$^+$]; HRMS (ESI) m/z calcd for C$_{24}$H$_{20}$F$_3$N$_2$O$_3$S [M+H$^+$] 473.1141, found 473.1146.

Example 17

10-Ethyl-N-(4-fluorobenzyl)-11-oxo-10,11-dihydrodibenzo[b,f][1,4]thiazepine-8-carboxamide 5-oxide (Compound 10)

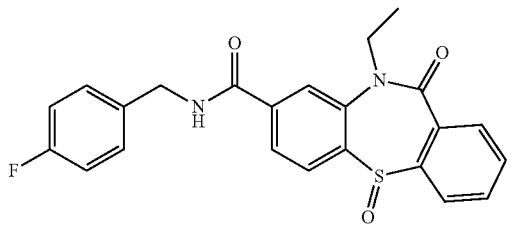 [SMILES: CCN1C(=O)c2ccccc2S(=O)c2ccc(C(=O)NCc3ccc(F)cc3)cc21]

The title compound was prepared according to the general protocol A. $^1$H NMR (400 MHz, DMSO-d$_6$) δ ppm 9.15 (t, J=5.5 Hz, 1 H), 8.00 (d, J=1.4 Hz, 1 H), 7.91 (dd, J=8.1, 1.1 Hz, 1 H), 7.65-7.74 (m, 3 H), 7.59-7.65 (m, 1 H), 7.50-7.57 (m, 1 H), 7.25-7.35 (m, 2 H), 7.04-7.15 (m, 2 H), 4.55 (dq, J=14.0, 7.1 Hz, 1 H), 4.33-4.49 (m, 2 H), 3.73 (dq, J=13.8, 6.9 Hz, 1 H), 1.17 (t, J=7.0 Hz, 3 H); $^{19}$F NMR (376 MHz, DMSO-d$_6$) δ ppm −116.20−−116.06 (m, 1 F); LCMS RT=5.34 min, m/z 423.1 [M+H$^+$]; HRMS (ESI) m/z calcd for C$_{23}$H$_{20}$FN$_2$O$_3$S [M+H$^+$] 423.1173, found 423.1176.

Example 18

N-(4-Cyanobenzyl)-10-ethyl-11-oxo-10,11-dihydrodibenzo[b,f][1,4]thiazepine-8-carboxamide 5-oxide (Compound 12)

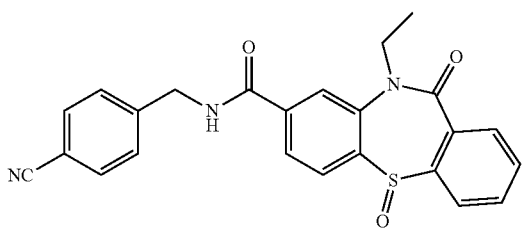 [SMILES: CCN1C(=O)c2ccccc2S(=O)c2ccc(C(=O)NCc3ccc(C#N)cc3)cc21]

The title compound was prepared according to the general protocol A. $^1$H NMR (400 MHz, DMSO-d$_6$) δ ppm 9.15 (t, J=5.9 Hz, 1 H), 8.02 (d, J=1.4 Hz, 1 H), 7.93 (dd, J=8.2, 1.6 Hz, 1 H), 7.66-7.73 (m, 3 H), 7.61-7.65 (m, 1 H), 7.55 (ddd, J=7.9, 6.9, 1.5 Hz, 1 H), 7.25-7.32 (m, 3 H), 7.17-7.25 (m, 1 H), 4.51-4.61 (m, 1 H), 4.35-4.51 (m, 2 H), 3.75 (td, J=14.0, 7.3 Hz, 1 H), 1.18 (t, J=7.1 Hz, 3 H); LCMS RT=5.05 min, m/z 452.1 [M+Na$^+$]; HRMS (ESI) m/z calcd for C$_{24}$H$_{20}$N$_3$O$_3$S [M+H$^+$] 430.1220, found 430.1224.

Example 19

10-Ethyl-N-(4-(methylsulfonyl)benzyl)-11-oxo-10,11-dihydrodibenzo[b,f][1,4]thiazepine-8-carboxamide 5-oxide (Compound 13)

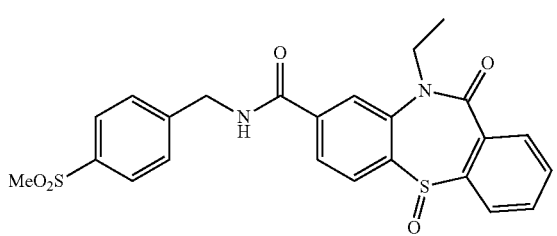 [SMILES: CCN1C(=O)c2ccccc2S(=O)c2ccc(C(=O)NCc3ccc(S(C)(=O)=O)cc3)cc21]

The title compound was prepared according to the general protocol B. $^1$H NMR (400 MHz, DMSO-d$_6$) δ ppm 9.27 (t, J=5.9 Hz, 1 H), 8.02 (d, J=1.2 Hz, 1 H), 7.93 (dd, J=8.3, 1.3 Hz, 1 H), 7.83 (d, J=8.0 Hz, 2 H), 7.66-7.74 (m, 3 H), 7.59-7.65 (m, 1 H), 7.49-7.58 (m, 3 H), 4.43-4.66 (m, 3 H), 3.74 (td, J=13.9, 6.8 Hz, 1 H), 3.14 (s, 3 H), 1.18 (t, J=7.0 Hz, 3 H); LCMS RT=4.66 min, m/z 483.1 [M+H$^+$]; HRMS (ESI) m/z calcd for C$_{24}$H$_{23}$N$_2$O$_5$S$_2$ [M+H$^+$] 483.1043, found 483.1048.

Example 20

10-Ethyl-11-oxo-N-(3,4,5-trimethoxybenzyl)-10,11-dihydrodibenzo[b,f][1,4]thiazepine-8-carboxamide 5-oxide (Compound 14)

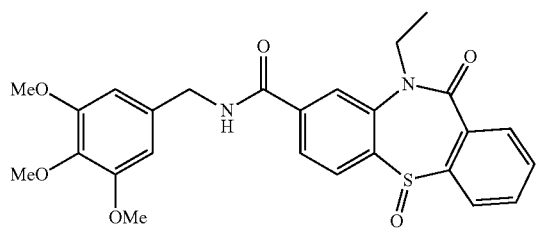 [SMILES: CCN1C(=O)c2ccccc2S(=O)c2ccc(C(=O)NCc3cc(OC)c(OC)c(OC)c3)cc21]

The title compound was prepared according to the general protocol A. $^1$H NMR (400 MHz, DMSO-d$_6$) δ ppm 9.06 (t, J=6.0 Hz, 1 H), 8.00 (d, J=1.6 Hz, 1 H), 7.92 (dd, J=8.2, 1.6 Hz, 1 H), 7.66-7.74 (m, 3 H), 7.61-7.65 (m, 1 H), 7.55 (ddd, J=7.9, 7.0, 1.4 Hz, 1 H), 6.61 (s, 2 H), 4.54 (dq, J=13.9, 7.2 Hz, 1 H), 4.30-4.45 (m, 2 H), 3.72-3.82 (m, 1 H), 3.71 (s, 6 H), 3.59 (s, 3 H), 1.18 (t, J=7.1 Hz, 3 H); LCMS RT=5.01 min, m/z 495.1 [M+H$^+$]; HRMS (ESI) m/z calcd for C$_{26}$H$_{27}$N$_2$O$_6$S [M+H$^+$] 495.1584, found 495.1589.

Example 21

N-(benzo[d][1,3]dioxol-5-ylmethyl)-10-ethyl-11-oxo-10,11dihydrodibenzo[b,f][1,4]thiazepine-8-carboxamide 5-oxide (Compound 15)

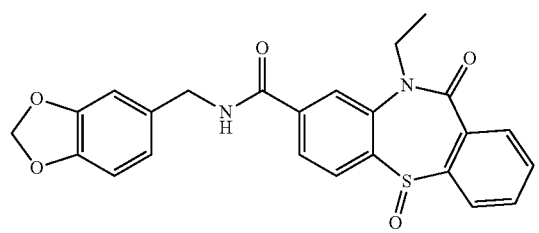 [SMILES: CCN1C(=O)c2ccccc2S(=O)c2ccc(C(=O)NCc3ccc4c(c3)OCO4)cc21]

The title compound was prepared according to the general protocol B. LCMS RT=5.20 min, m/z 449.1 [M+H$^+$]; HRMS (ESI) m/z calcd for C$_{24}$H$_{21}$N$_2$O$_5$S [M+H$^+$] 449.1166, found 449.1160.

Example 22

10-Ethyl-11-oxo-N-phenyl-10,11-dihydrodibenzo[b,f][1,4]thiazepine-8-carboxamide 5-oxide (Compound 16)

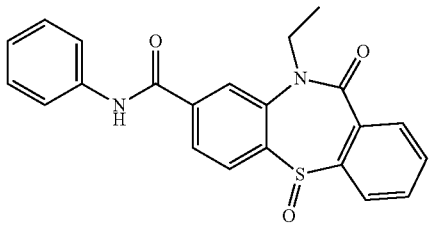 [SMILES: CCN1C(=O)c2ccccc2S(=O)c2ccc(C(=O)Nc3ccccc3)cc21]

The title compound was prepared according to the general protocol A. $^1$H NMR (400 MHz, DMSO-d$_6$) δ ppm 10.31 (s, 1 H), 8.08 (d, J=1.6 Hz, 1 H), 7.96 (dd, J=8.0, 1.4 Hz, 1 H), 7.62-7.76 (m, 6 H), 7.56 (td, J=7.3, 1.4 Hz, 1 H), 7.33 (t, J=7.9 Hz, 2 H), 7.09 (t, J=7.4 Hz, 1 H), 4.59 (dq, J=13.9, 7.0 Hz, 1 H), 3.79 (td, J=13.9, 6.9 Hz, 1 H), 1.19 (t, J=7.0 Hz, 3 H); LCMS RT=5.35 min, m/z 391.1 [M+H$^+$]; HRMS (ESI) m/z calcd for C$_{22}$H$_{19}$N$_2$O$_3$S [M+H$^+$] 391.1111, found 391.1124.

Example 23

10-Ethyl-N-(4-methoxyphenyl)-11-oxo-10,11-dihydrodibenzo[b,f][1,4]thiazepine-8-carboxamide 5-oxide (Compound 17)

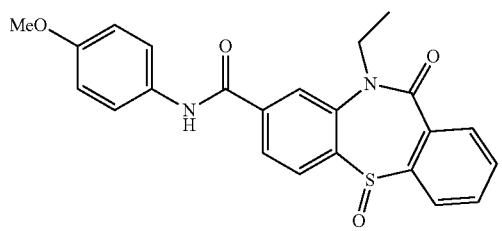 [SMILES: CCN1C(=O)c2ccccc2S(=O)c2ccc(C(=O)Nc3ccc(OC)cc3)cc21]

The title compound was prepared according to the general protocol A. $^1$H NMR (400 MHz, DMSO-d$_6$) δ ppm 10.20 (s, 1 H), 8.07 (d, J=1.4 Hz, 1 H), 7.96 (dd, J=8.2, 1.6 Hz, 1 H), 7.68-7.76 (m, 3 H), 7.62-7.67 (m, 1 H), 7.48-7.61 (m, 3 H), 6.85-6.95 (m, 2 H), 4.50-4.69 (m, 1 H), 3.74-3.85 (m, 1 H), 3.72 (s, 3 H), 1.20 (t, J=7.0 Hz, 3 H); LCMS RT=5.27 min, m/z 421.0 [M+H$^+$]; HRMS (ESI) m/z calcd for C$_{23}$H$_{21}$N$_2$O$_4$S [M+H$^+$] 421.1217, found 421.1215.

Example 24

10-Ethyl-N-(4-methoxyphenethyl)-11-oxo-10,11-dihydrodibenzo[b,f][1,4]thiazepine-8-carboxamide 5-oxide (Compound 18)

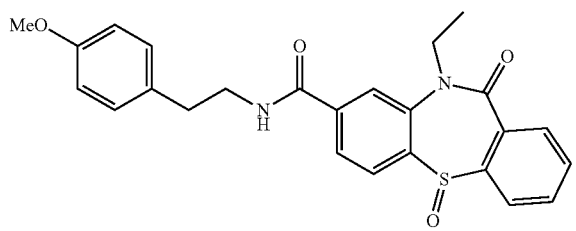 [SMILES: CCN1C(=O)c2ccccc2S(=O)c2ccc(C(=O)NCCc3ccc(OC)cc3)cc21]

The title compound was prepared according to the general protocol A. $^1$H NMR (400 MHz, DMSO-d$_6$) δ ppm 8.65 (t, J=5.9 Hz, 1 H), 7.90 (d, J=1.4 Hz, 1 H), 7.84 (dd, J=8.2, 1.2 Hz, 1 H), 7.59-7.75 (m, 4 H), 7.54 (td, J=7.4, 1.3 Hz, 1 H), 7.07-7.14 (m, 2 H), 6.78-6.84 (m, 2 H), 4.54 (dq, J=14.1, 7.1 Hz, 1 H), 3.68-3.80 (m, 1 H), 3.68 (s, 3 H), 3.33-3.46 (m, 2 H), 2.71 (t, J=7.3 Hz, 2 H), 1.18 (t, J=7.1 Hz, 3 H); LCMS RT=5.33 min, m/z 449.1 [M+H$^+$]; HRMS (ESI) m/z calcd for C$_{25}$H$_{25}$N$_2$O$_4$S [M+H$^+$] 449.1530, found 449.1535.

Example 25

N-(4-Methoxybenzyl)-11-oxo-10,11-dihydrodibenzo[b,f][1,4]thiazepine-8-carboxamide 5-oxide (Compound 19)

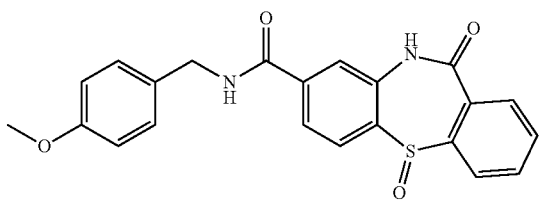 [SMILES: COc1ccc(CNC(=O)c2ccc3c(c2)NC(=O)c2ccccc2S3=O)cc1]

The title compound was prepared according to the general protocol A. LCMS RT=4.68 min, m/z 813.2 [2M+H$^+$]; HRMS (ESI) m/z calcd for C$_{22}$H$_{19}$N$_2$O$_4$S [M+H$^+$] 407.1060, found 407.1056.

Example 26

N-(4-Methoxybenzyl)-10-methyl-11-oxo-10,11-dihydrodibenzo[b,f][1,4]thiazepine-8-carboxamide 5-oxide (Compound 20)

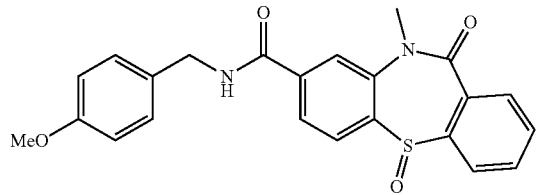 [SMILES: COc1ccc(CNC(=O)c2ccc3c(c2)N(C)C(=O)c2ccccc2S3=O)cc1]

The title compound was prepared according to the general protocol A. LCMS RT=4.97 min, m/z 421.1 [M+H$^+$]; HRMS (ESI) m/z calcd for C$_{23}$H$_{21}$N$_2$O$_4$S [M+H$^+$] 421.1217, found 421.1217.

Example 27

N-(4-Methoxybenzyl)-11-oxo-10-propyl-10,11-dihydrodibenzo[b,f][1,4]thiazepine-8-carboxamide 5-oxide (Compound 21)

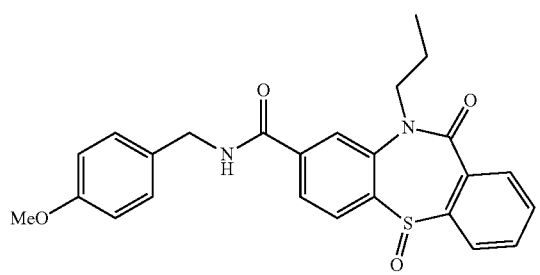 [SMILES: CCCN1C(=O)c2ccccc2S(=O)c2ccc(C(=O)NCc3ccc(OC)cc3)cc21]

The title compound was prepared according to the general protocol A. LCMS RT=5.50 min, m/z 449.1 [M+H⁺]; HRMS (ESI) m/z calcd for $C_{25}H_{25}N_2O_4S$ [M+H⁺] 449.1530, found 449.1527.

Example 28

10-Benzyl-N-(4-methoxybenzyl)-11-oxo-10,11-dihydrodibenzo[b,f][1,4]thiazepine-8-carboxamide 5-oxide (Compound 22)

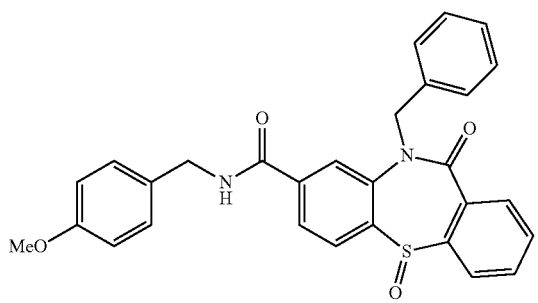 [SMILES: COc1ccc(CNC(=O)c2ccc3c(c2)N(Cc2ccccc2)C(=O)c2ccccc2S3=O)cc1]

The title compound was prepared according to the general protocol A. $^1$H NMR (400 MHz, DMSO-d$_6$) δ ppm 9.05 (t, J=5.9 Hz, 1 H), 8.10 (d, J=1.4 Hz, 1 H), 7.84 (dd, J=8.2, 1.6 Hz, 1 H), 7.77 (dd, J=7.6, 1.0 Hz, 1 H), 7.67-7.74 (m, 1 H), 7.60-7.65 (m, 1 H), 7.54-7.60 (m, 2 H), 7.26-7.34 (m, 5 H), 7.15-7.23 (m, 2 H), 6.81-6.89 (m, 2 H), 5.77 (d, J=15.1 Hz, 1 H), 4.94 (d, J=15.1 Hz, 1 H), 4.27-4.48 (m, 2 H), 3.70 (s, 3 H); LCMS RT=5.75 min, m/z 497.1 [M+H⁺]; HRMS (ESI) m/z calcd for $C_{29}H_{25}N_2O_4S$ [M+H⁺] 497.153, found 497.1526.

Example 29

10-Methyl-11-oxo-N-phenyl-10,11-dihydrodibenzo[b,f][1,4]thiazepine-8-carboxamide 5-oxide (Compound 23)

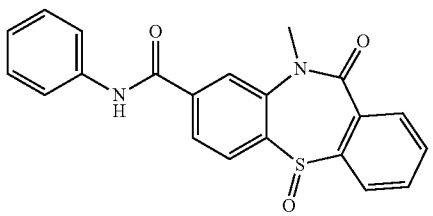 [SMILES: CN1C(=O)c2ccccc2S(=O)c2ccc(C(=O)Nc3ccccc3)cc21]

The title compound was prepared according to the general protocol A. $^1$H NMR (400 MHz, DMSO-d$_6$) δ ppm 10.31 (s, 1 H), 8.07 (d, J=1.4 Hz, 1 H), 7.96 (dd, J=8.1, 1.7 Hz, 1 H), 7.64-7.80 (m, 6 H), 7.58 (td, J=7.4, 1.4 Hz, 1 H), 7.20-7.42 (m, 2 H), 7.02-7.16 (m, 1 H), 3.59 (s, 3 H); LCMS RT=5.18 min, m/z 377.0 [M+H⁺]; HRMS (ESI) m/z calcd for $C_{21}H_{17}N_2O_3S$ [M+H⁺] 377.0954, found 377.0953.

Example 30

N-(4-Methoxyphenyl)-10-methyl-11-oxo-10,11-dihydrodibenzo[b,f][1,4]thiazepine-8-carboxamide 5-oxide (Compound 24)

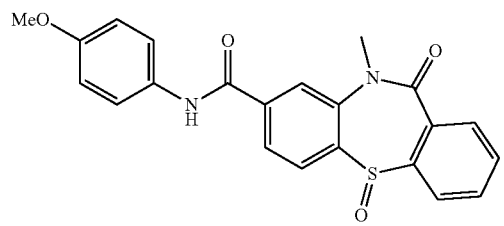 [SMILES: COc1ccc(NC(=O)c2ccc3c(c2)N(C)C(=O)c2ccccc2S3=O)cc1]

The title compound was prepared according to the general protocol A. LCMS RT=5.09 min, m/z 407.0 [M+H⁺]; HRMS (ESI) m/z calcd for $C_{22}H_{19}N_2O_4S$ [M+H⁺] 407.1060, found 407.1061.

Example 31

N-Benzyl-10-methyl-11-oxo-10,11-dihydrodibenzo[b,f][1,4]thiazepine-8-carboxamide 5-oxide (Compound 25)

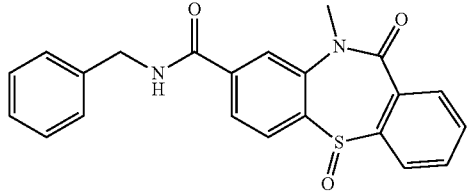 [SMILES: CN1C(=O)c2ccccc2S(=O)c2ccc(C(=O)NCc3ccccc3)cc21]

The title compound was prepared according to the general protocol B. $^1$H NMR (400 MHz, DMSO-d$_6$) δ ppm 9.15 (t, J=6.0 Hz, 1 H), 8.02 (s, 1 H), 7.93 (dt, J=8.2, 1.1 Hz, 1 H), 7.70-7.76 (m, 2 H), 7.64-7.69 (m, 2 H), 7.52-7.60 (m, 1 H), 7.25-7.33 (m, 4H), 7.17-7.25 (m, 1 H), 4.35-4.53 (m, 2 H), 3.55 (d, J=1.0 Hz, 3 H); LCMS RT=5.06 min, m/z 391.0 [M+H⁺]; HRMS (ESI) m/z calcd for $C_{22}H_{19}N_2O_3S$ [M+H⁺] 391.1111, found 391.1114.

Example 32

N-(4-Fluorobenzyl)-10-methyl-11-oxo-10,11-dihydrodibenzo[b,f][1,4]thiazepine-8-carboxamide 5-oxide (Compound 26)

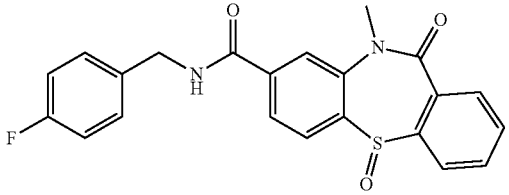

The title compound was prepared according to the general protocol A. LCMS RT=5.17 min, m/z 409.0 [M+H$^+$]; HRMS (ESI) m/z calcd for C$_{22}$H$_{18}$FN$_2$O$_3$S [M+H$^+$] 409.1017, found 409.1019.

Example 33

N-(4-Chlorobenzyl)-10-methyl-11-oxo-10,11-dihydrodibenzo[b,f][1,4]thiazepine-8-carboxamide 5-oxide (Compound 27)

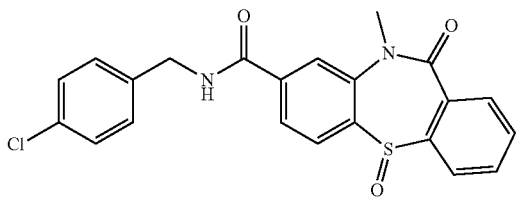 [SMILES: CN1C(=O)c2ccccc2S(=O)c2ccc(C(=O)NCc3ccc(Cl)cc3)cc21]

The title compound was prepared according to the general protocol B. $^1$H NMR (400 MHz, DMSO-d$_6$) δ ppm 9.18 (t, J=5.9 Hz, 1 H), 8.01 (d, J=1.4 Hz, 1 H), 7.92 (dd, J=8.2, 1.6 Hz, 1 H), 7.69-7.77 (m, 2 H), 7.62-7.69 (m, 2 H), 7.56 (ddd, J=8.0, 7.0, 1.5 Hz, 1 H), 7.26-7.40 (m, 4 H), 4.30-4.54 (m, 2 H), 3.54 (s, 3 H); LCMS RT=5.48 min, m/z 425.0 [M+H$^+$]; HRMS (ESI) m/z calcd for C$_{22}$H$_{18}$ClN$_2$O$_3$S [M+H$^+$] 425.0721, found 425.0724.

Example 34

N-(3-Chlorobenzyl)-10-methyl-11-oxo-10,11-dihydrodibenzo[b,f][1,4]thiazepine-8-carboxamide 5-oxide (Compound 28)

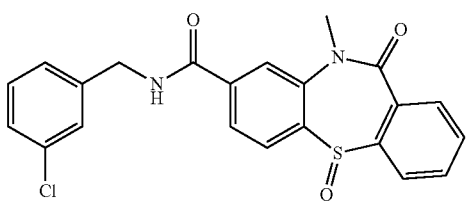 [SMILES: CN1C(=O)c2ccccc2S(=O)c2ccc(C(=O)NCc3cccc(Cl)c3)cc21]

The title compound was prepared according to the general protocol A. LCMS RT=5.47 min, m/z 425.0 [M+H$^+$]; HRMS (ESI) m/z calcd for C$_{22}$H$_{18}$ClN$_2$O$_3$S [M+H$^+$] 425.0721, found 425.0725.

Example 35

N-(4-Bromobenzyl)-10-methyl-11-oxo-10,11-dihydrodibenzo[b,f][1,4]thiazepine-8-carboxamide 5-oxide (Compound 29)

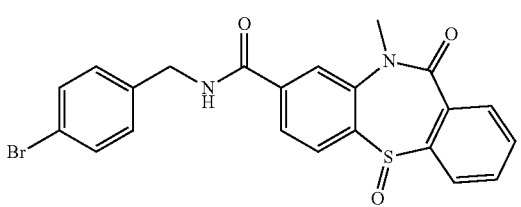

The title compound was prepared according to the general protocol A. $^1$H NMR (400 MHz, DMSO-d$_6$) δ ppm 9.18 (t, J=5.8 Hz, 1 H), 8.01 (d, J=1.4 Hz, 1 H), 7.92 (dd, J=8.2, 1.6 Hz, 1 H), 7.70-7.79 (m, 2 H), 7.62-7.70 (m, 2 H), 7.53-7.61 (m, 1 H), 7.41-7.52 (m, 2 H), 7.17-7.31 (m, 2 H), 4.30-4.49 (m, 2 H), 3.47-3.60 (m, 3 H); LCMS RT=5.57 min, m/z 469.0 [M+H$^+$]; HRMS (ESI) m/z calcd for C$_{22}$H$_{18}$BrN$_2$O$_3$S [M+H$^+$] 469.0216, found 469.0215.

Example 36

10-Methyl-11-oxo-N-(pyridin-2-ylmethyl)-10,11-dihydrodibenzo[b,f][1,4]thiazepine-8-carboxamide 5-oxide (Compound 30)

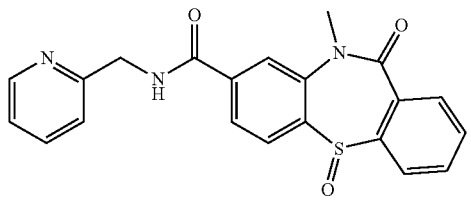 [SMILES: CN1C(=O)c2ccccc2S(=O)c2ccc(C(=O)NCc3ccccn3)cc21]

The title compound was prepared according to the general protocol B. $^1$H NMR (400 MHz, DMSO-d$_6$) δ ppm 9.17-9.39 (m, 1 H), 8.42-8.62 (m, 1 H), 8.05 (d, J=1.6 Hz, 1 H), 7.95 (dd, J=8.2, 1.6 Hz, 1 H), 7.77-7.90 (m, 1 H), 7.64-7.77 (m, 4 H), 7.57 (ddd, J=7.9, 7.0, 1.4 Hz, 1 H), 7.28-7.47 (m, 2 H), 4.52-4.65 (m, 2 H), 3.56 (s, 3 H); LCMS RT=3.20 min, m/z 392.0 [M+H$^+$]; HRMS (ESI) m/z calcd for C$_{21}$H$_{18}$N$_3$O$_3$S [M+H$^+$] 392.1063, found 392.1062.

Example 37

10-Methyl-11-oxo-N-(pyridin-3-ylmethyl)-10,11-dihydrodibenzo[b,f][1,4]thiazepine-8-carboxamide 5-oxide (Compound 31)

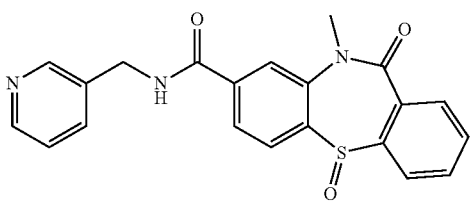 [SMILES: CN1C(=O)c2ccccc2S(=O)c2ccc(C(=O)NCc3cccnc3)cc21]

The title compound was prepared according to the general protocol B. $^1$H NMR (400 MHz, DMSO-d$_6$) δ ppm 9.34 (t, J=6.1 Hz, 1 H), 8.55-8.69 (m, 2 H), 8.05 (d, J=1.6 Hz, 1 H), 7.94 (dd, J=8.2, 1.6 Hz, 1 H), 7.65-7.78 (m, 4 H), 7.53-7.61 (m, 3 H), 4.53-4.63 (m, 2 H), 3.57 (s, 3 H); LCMS RT=3.25 min, m/z 392.0 [M+H$^+$]; HRMS (ESI) m/z calcd for C$_{21}$H$_{18}$N$_3$O$_3$S [M+H$^+$] 392.1063, found 392.1060.

Example 38

10-Methyl-11-oxo-N-(2-(thiophen-2-yl)ethyl)-10,11-dihydrodibenzo[b,f][1,4]thiazepine-8-carboxamide 5-oxide (Compound 32, (Rac-55)

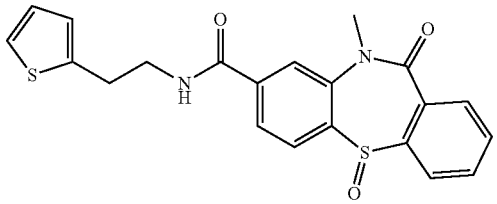 [SMILES: CN1C(=O)c2ccccc2S(=O)c2ccc(C(=O)NCCc3cccs3)cc21]

The title compound was prepared according to the general protocol A. $^1$H NMR (400 MHz, DMSO-d$_6$) δ ppm 8.76 (t, J=5.8 Hz, 1 H), 7.94 (d, J=1.6 Hz, 1 H), 7.86 (dd, J=8.2, 1.4 Hz, 1 H), 7.69-7.77 (m, 2 H), 7.67 (d, J=8.0 Hz, 2 H), 7.57 (td, J=7.4, 1.1 Hz, 1H), 7.27-7.35 (m, 1 H), 6.83-6.98 (m, 2 H), 3.55 (s, 3 H), 3.40-3.51 (m, 2 H), 2.96-3.08 (m, 2 H); LCMS RT=5.10 min, m/z 411.0 [M+H$^+$]; HRMS (ESI) m/z calcd for C$_{21}$H$_{19}$N$_2$O$_3$S$_2$ [M+H$^+$] 411.0832, found 411.0828.

Example 39

10-Methyl-11-oxo-N-(2-(pyrrolidin-1-yl)ethyl)-10,11-dihydrodibenzo[b,f][1,4]thiazepine-8-carboxamide 5-oxide (Compound 33)

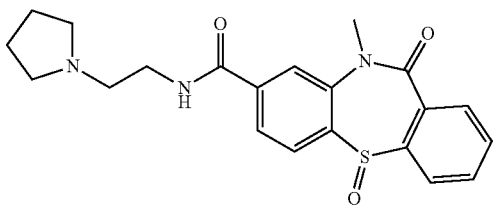 [SMILES: CN1C(=O)c2ccccc2S(=O)c2ccc(C(=O)NCCN3CCCC3)cc21]

The title compound was prepared according to the general protocol B. $^1$H NMR (400 MHz, DMSO-d$_6$) δ ppm 8.68-8.93 (m, 1 H), 7.94-8.02 (m, 1 H), 7.84-7.94 (m, 1 H), 7.63-7.79 (m, 3 H), 7.51-7.63 (m, 1 H), 7.28-7.44 (m, 1 H), 3.56 (s, 3 H), 3.44-3.69 (m, 6 H), 3.03 (br. s., 2 H), 1.98 (br. s., 2 H), 1.71-1.89 (m, 2 H); LCMS RT=3.27 min, m/z 398.1 [M+H$^+$]; HRMS (ESI) m/z calcd for C$_{21}$H$_{24}$N$_3$O$_3$S [M+H$^+$] 398.1533, found 398.1538.

Example 40

10-Methyl-11-oxo-N-(2-(piperidin-1-yl)ethyl)-10,11-dihydrodibenzo[b,f][1,4]thiazepine-8-carboxamide 5-oxide (Compound 34)

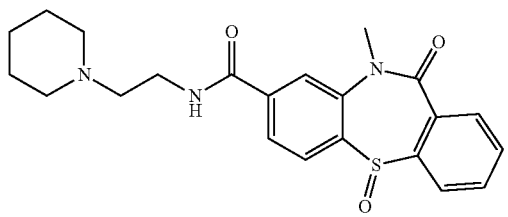 [SMILES: CN1C(=O)c2ccccc2S(=O)c2ccc(C(=O)NCCN3CCCCC3)cc21]

The title compound was prepared according to the general protocol B. $^1$H NMR (400 MHz, DMSO-d$_6$) δ ppm 8.82 (t, J=5.4 Hz, 1 H), 7.96 (d, J=1.6 Hz, 1 H), 7.89 (dd, J=8.2, 1.6 Hz, 1 H), 7.69-7.78 (m, 3 H), 7.64-7.69 (m, 1 H), 7.57 (td, J=7.5, 1.5 Hz, 1 H), 3.56 (s, 3 H), 3.53-3.67 (m, 2 H), 3.49 (d, J=12.7 Hz, 2 H), 3.14-3.23 (m, 2 H), 2.83-2.96 (m, 2 H), 1.80 (d, J=14.9 Hz, 2 H), 1.50-1.73 (m, 3 H), 1.28-1.43 (m, 1 H); LCMS RT=3.39 min, m/z 412.1 [M+H$^+$]; HRMS (ESI) m/z calcd for C$_{22}$H$_{26}$N$_3$O$_3$S [M+H$^+$] 412.1689, found 412.1694.

Example 41

N-(3-(Dimethylamino)propyl)-10-methyl-11-oxo-10,11-dihydrodibenzo[b,f][1,4]thiazepine-8-carboxamide 5-oxide (Compound 35)

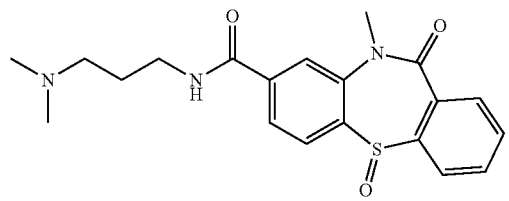 [SMILES: CN(C)CCCNC(=O)c1ccc2c(c1)N(C)C(=O)c1ccccc1S2=O]

The title compound was prepared according to the general protocol B. $^1$H NMR (400 MHz, DMSO-d$_6$) δ ppm 8.72 (t, J=5.8 Hz, 1 H), 7.95 (d, J=1.4 Hz, 1 H), 7.88 (dd, J=8.2, 1.6 Hz, 1 H), 7.63-7.80 (m, 4 H), 7.57 (td, J=7.4, 1.4 Hz, 1 H), 3.56 (s, 3 H), 3.18-3.38 (m, 2 H), 2.97-3.11 (m, 2 H), 2.73 (s, 6 H), 1.71-1.92 (m, 2 H); LCMS RT=3.21 min, m/z 386.1 [M+H$^+$]; HRMS (ESI) m/z calcd for C$_{20}$H$_{24}$N$_3$O$_3$S [M+H$^+$] 386.1533, found 386.1535.

Example 42

10-Ethyl-N-(4-methoxybenzyl)-11-oxo-10,11-dihydrodibenzo[b,f][1,4]thiazepine-8-carboxamide (Compound 36)

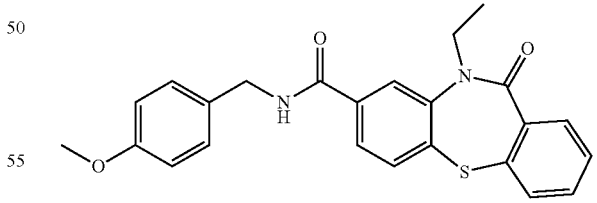

The title compound was prepared according to the general protocol B. $^1$H NMR (400 MHz, DMSO-d$_6$) δ ppm 9.03 (t, J=5.8 Hz, 1 H), 7.97 (d, J=1.6 Hz, 1 H), 7.69-7.78 (m, 1 H), 7.61-7.68 (m, 1 H), 7.54-7.60 (m, 1 H), 7.44-7.51 (m, 1 H), 7.32-7.42 (m, 2 H), 7.20 (d, J=8.2 Hz, 2 H), 6.85 (d, J=8.8 Hz, 2 H), 4.47-4.59 (m, 1 H), 4.25-4.44 (m, 2H), 3.70-3.79 (m, 1 H), 3.69 (s, 3 H), 1.12 (t, J=7.0 Hz, 3 H); LCMS RT=5.79 min, m/z 419.2 [M+H$^+$]; HRMS (ESI) m/z calcd for C$_{24}$H$_{23}$N$_2$O$_3$S [M+H$^+$] 419.1424, found 419.1413.

Example 43

10-Ethyl-N-(4-Methoxybenzyl)-11-oxo-10,11-Dihydrodibenzo[B,F][1,4]Thiazepine-8-Carboxamide 5,5-Dioxide (Compound 37)

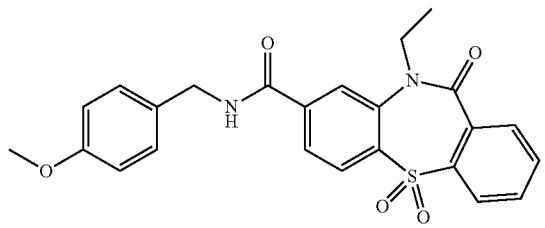 [SMILES: CCN1C(=O)c2ccccc2S(=O)(=O)c2ccc(C(=O)NCc3ccc(OC)cc3)cc21]

A solution of 10-ethyl-N-(4-methoxybenzyl)-11-oxo-10,11-dihydrodibenzo[b,f][1,4]thiazepine-8-carboxamide (10.0 mg, 0.024 mmol) in dichloromethane (3.00 mL) and was treated at room temperature with MCPBA (53.6 mg, 0.24 mmol). The reaction was stirred at room temperature for overnight. The reaction mixture was washed with saturated $Na_2S_2O_3$ solution. The organic layer was separated, dried and concentrated. The crude mixture was purified by preparative HPLC to give 2.0 mg (19%) of the title compound as a white foam. LCMS RT=5.46 min, m/z 451.1 [M+H$^+$]; HRMS (ESI) m/z calcd for $C_{24}H_{23}N_2O_5S$ [M+H$^+$] 451.1322, found 451.1322.

Example 44

10-Ethyl-N-(4-methoxybenzyl)-11-oxo-10,11-dihydrodibenzo[b,f][1,4]thiazepine-8-carboxamide 5-(S)-oxide (Compound 38)

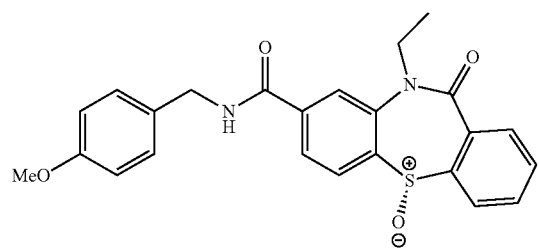 [SMILES: CCN1C(=O)c2ccccc2[S@+]([O-])c2ccc(C(=O)NCc3ccc(OC)cc3)cc21]

LCMS RT=5.22 min, m/z 435.1 [M+H$^+$]; HRMS (ESI) m/z calcd for $C_{24}H_{23}N_2O_4S$ [M+H$^+$] 435.1373, found 435.1353.

Example 45

10-Ethyl-N-(4-methoxybenzyl)-11-oxo-10,11-dihydrodibenzo[b,f][1,4]thiazepine-8-carboxamide 5-(R)-oxide (Compound 39)

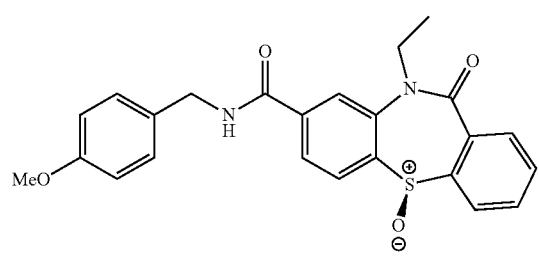 [SMILES: CCN1C(=O)c2ccccc2[S@@+]([O-])c2ccc(C(=O)NCc3ccc(OC)cc3)cc21]

Separation of enantiomers via chiral HPLC: Analytical analysis was performed on a CHIRALPAK° IA® column (4.6×150 mm, 5 micron). The mobile phase was 60% of isopropanol in hexanes at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=5.22 minutes; positive optical rotation. The second eluting peak: RT=5.61 minutes; negative optical rotation. Preparative separation was performed on a CHIRALPAK®IA® column (5×50 cm, 20 micron). The mobile phase was 60% of isopropanol in hexanes at a flow rate of 30 mL/min. Fraction collection was triggered by UV absorbance (254 nm). LCMS RT=5.22 min, m/z 435.1 [M+H$^+$]; HRMS (ESI) m/z calcd for $C_{24}H_{23}N_2O_4S$ [M+H$^+$] 435.1373, found 435.1356.

Example 46

N-(4-Methoxybenzyl)-9,10-dioxo-9,10-dihydroanthracene-2-carboxamide (Compound 40)

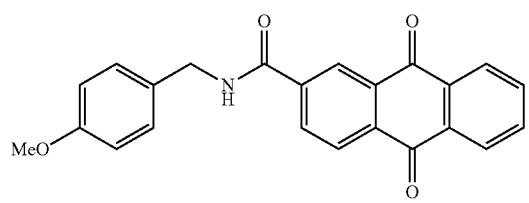 [SMILES: COc1ccc(CNC(=O)c2ccc3c(c2)C(=O)c2ccccc2C3=O)cc1]

A solution of 9,10-dioxo-9,10-dihydroanthracene-2-carboxylic acid (1.00 g, 3.96 mmol) in DMF (15.0 mL) was treated at room temperature with (4-methoxyphenyl)methanamine (1.09 g, 7.93 mmol), HATU (2.26 g, 5.95 mmol) and DIPEA (2.08 mL, 11.9 mmol). The reaction mixture was stirred at room temperature for 2 hours. The mixture was concentrated and purified by Biotage with 0-20% of MeOH in $CH_2Cl_2$ to give 1.30 g (88%) of the title compound as a yellow solid. $^1$H NMR (400 MHz, DMSO-d$_6$) δ ppm 9.45 (t, J=5.3 Hz, 1 H), 8.67 (t, J=1.8 Hz, 1 H), 8.33-8.39 (m, 1 H), 8.18-8.31 (m, 3 H), 7.95 (ddd, J=5.6, 3.4, 2.2 Hz, 2 H), 7.20-7.32 (m, 2 H), 6.80-6.97 (m, 2 H), 4.45 (d, J=5.7 Hz, 2 H), 3.72 (s, 3 H); LCMS RT=5.99 min, m/z 372.0 [M+H$^+$].

Example 47

10-Ethyl-N-(4-methoxybenzyl)-N-methyl-11-oxo-10,11-dihydrodibenzo[b,f][1,4]thiazepine-8-carboxamide 5-oxide (Compound 42)

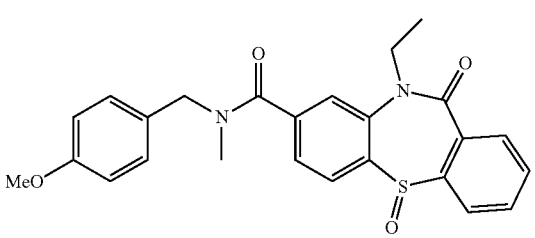

A solution of 10-ethyl-N-(4-methoxybenzyl)-11-oxo-10,11-dihydrodibenzo[b,f][1,4]thiazepine-8-carboxamide in DMF (2.50 mL) was treated at 0° C. with NaH (18.4 mg, 0.46 mmol). The reaction mixture was warmed to room temperature and stirred at room temperature for 1 h. a solution of MeI (0.029 mL, 0.46 mmol) in DMF (1.00 mL) was added to the mixture dropwise. The reaction mixture was stirred at room temperature for 1.5 h. Water was carefully added and the aqueous layer was extracted with 20% MeOH in dichloromethane. The aqueous layer was separated, dried, concentrated and purified by preparative HPLC to give 12.0 mg (58%) of the title compound. LCMS RT=5.26 min, m/z 449.1 [M+H$^+$]; HRMS (ESI) m/z calcd for $C_{21}H_{16}NO_4S$ [M+H$^+$] 449.1530, found 449.1524.

Example 48

N-Benzyl-N,10-diethyl-11-oxo-10,11-dihydrod-ibenzo[b,f][1,4]thiazepine-8-carboxamide 5-oxide (Compound 43)

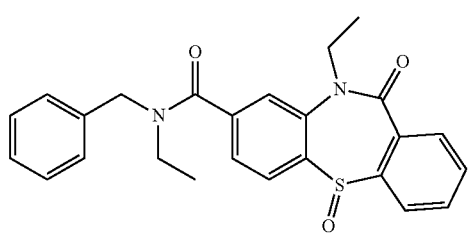 [SMILES: CCN(Cc1ccccc1)C(=O)c1ccc2c(c1)N(CC)C(=O)c1ccccc1S2=O]

The title compound was prepared according to the general protocol A. LCMS RT=5.54 min, m/z 433.1 [M+H$^+$]; HRMS (ESI) m/z calcd for $C_{25}H_{25}N_2O_3S$ [M+H$^+$] 433.1580, found 433.1580.

Example 49

4-Methoxybenzyl 10-ethyl-11-oxo-10,11-dihydrod-ibenzo[b,f][1,4]thiazepine-8-carboxylate 5-oxide (Compound 44)

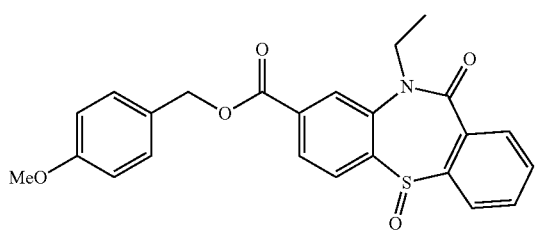

A solution of 10-ethyl-11-oxo-10,11-dihydrodibenzo[b,f][1,4]thiazepine-8-carboxylic acid 5-oxide (180 mg, 0.57 mmol) in DMF (5.00 mL) and was treated at 0° C. with NaH (68.5 mg, 1.71 mmol). The reaction mixture was warmed to room temperature and stirred at room temperature for 1 h. A solution of 1-(bromomethyl)-4-methoxybenzene (344 mg, 1.71 mmol) in DMF (2.00 mL) was added dropwise to the mixture. The reaction mixture was stirred at room temperature for 1.5 h. Water was carefully added and the aqueous layer was extracted with EtOAc. The organic layer was separated, dried, concentrated and purified by preparative HPLC to give 21.6 mg (9%) of the title compound. The title compound also can be prepared using a different protocol: A solution of 10-ethyl-11-oxo-10,11-dihydrodibenzo[b,f][1,4]thiazepine-8-carboxylic acid 5-oxide (50.0 mg, 0.16 mmol) in DMF (2.00 mL) was treated at room temperature with $K_2CO_3$ (110 mg, 0.79 mmol) and 1-(bromomethyl)-4-methoxybenzene (96 mg, 0.48 mmol). The reaction mixture was stirred at room temperature for overnight. The reaction mixture was filtered and purified by preparative HPLC to give 7.2 mg (10%) of the title compound. $^1$H NMR (400 MHz, DMSO-d$_6$) δ ppm 8.07 (d, J=1.4 Hz, 1 H), 8.00 (dd, J=8.1, 1.5 Hz, 1 H), 7.74 (d, J=8.2 Hz, 1 H), 7.66-7.71 (m, 2 H), 7.60-7.65 (m, 1 H), 7.51-7.59 (m, 1 H), 7.31-7.40 (m, 2 H), 6.83-6.96 (m, 2 H), 5.25 (q, J=11.9 Hz, 2 H), 4.55 (dq, J=14.0, 7.1 Hz, 1 H), 3.73 (s, 3 H), 3.62-3.78 (m, 1 H), 1.16 (t, J=7.1 Hz, 3 H); LCMS RT=6.12 min, m/z 458.1 [M+Na$^+$]; HRMS (ESI) m/z calcd for $C_{24}H_2$,NNaO$_5$S [M+Na$^+$] 458.1033, found 458.1029.

Example 50

N-(10-Ethyl-11-oxo-10,11-dihydrodibenzo[b,f][1,4]thiazepin-8-yl)-2-(4-methoxyphenyl)acetamide 5-oxide (Compound 45)

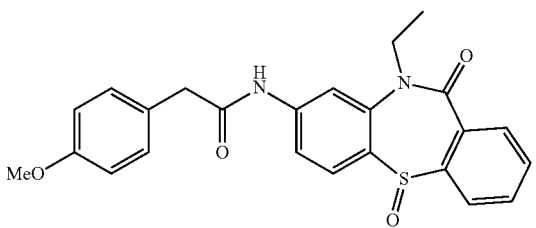

The title compound was prepared according to the general protocol B. $^1$H NMR (400 MHz, DMSO-d$_6$) δ ppm 10.44 (s, 1 H), 7.93 (d, J=1.6 Hz, 1 H), 7.64-7.73 (m, 2H), 7.46-7.63 (m, 4 H), 7.12-7.23 (m, 2 H), 6.76-6.89 (m, 2 H), 4.28-4.53 (m, 1 H), 3.69 (s, 3 H), 3.58-3.73 (m, 1 H), 3.54 (s, 2 H), 1.21 (t, J=7.0 Hz, 3 H); LCMS RT=5.39 min, m/z 435.1 [M+H$^+$]; HRMS (ESI) m/z calcd for $C_{24}H_{23}N_2O_4S$ [M+H$^+$] 435.1373, found 435.1371.

Example 51

N-(10-Ethyl-11-oxo-10,11-dihydrodibenzo[b,f][1,4]thiazepin-8-yl)-2-(4-fluorophenyl)acetamide 5-oxide (Compound 46)

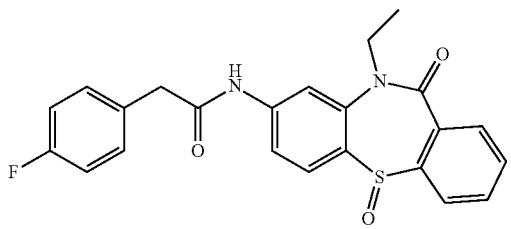 [SMILES: CCN1C(=O)c2ccccc2S(=O)c2ccc(NC(=O)Cc3ccc(F)cc3)cc21]

The title compound was prepared according to the general protocol B. $^1$H NMR (400 MHz, DMSO-d$_6$) δ ppm 10.49 (s, 1 H), 7.93 (d, J=2.0 Hz, 1 H), 7.64-7.73 (m, 2 H), 7.47-7.64 (m, 4 H), 7.24-7.39 (m, 2 H), 7.01-7.19 (m, 2 H), 4.40 (dq, J=13.8, 7.2 Hz, 1 H), 3.62 (s, 2 H), 3.55-3.71 (m, 1 H), 1.21

(t, J=7.0 Hz, 3 H); $^{19}$F NMR (376 MHz, DMSO-d$_6$) δ ppm −116.73- −116.14 (m, 1 F); LCMS RT=5.50 min, m/z 423.1 [M+H$^+$]; HRMS (ESI) m/z calcd for C$_{23}$H$_{20}$FN$_2$O$_3$S [M+H$^+$] 423.1173, found 423.1174.

Example 52

10-Ethyl-N-(4-fluorobenzyl)-11-oxo-10,11-dihydrodibenzo[b,f][1,4]thiazepine-8-carboxamide 5-(S)-oxide (Compound 47)

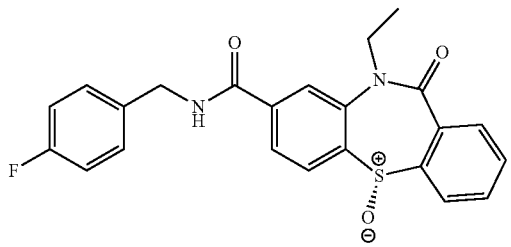 [SMILES: CCN1C(=O)c2ccccc2[S@+]([O-])c2ccc(C(=O)NCc3ccc(F)cc3)cc21]

LCMS RT=5.43 min, m/z 423.1 [M+H$^+$]; HRMS (ESI) m/z calcd for C$_{23}$H$_{20}$FN$_2$O$_3$S [M+H$^+$] 423.1173, found 423.1181.

Example 53

N-(4-Cyanobenzyl)-10-ethyl-11-oxo-10,11-dihydrodibenzo[b,f][1,4]thiazepine-8-carboxamide 5-(S)-oxide (Compound 48)

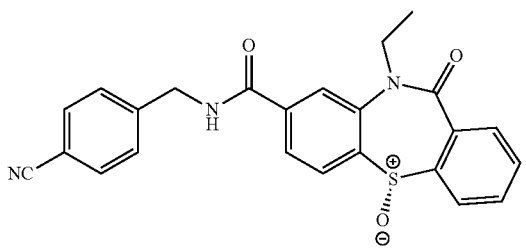 [SMILES: CCN1C(=O)c2ccccc2[S@+]([O-])c2ccc(C(=O)NCc3ccc(C#N)cc3)cc21]

LCMS RT=5.14 min, m/z 430.1 [M+H$^+$]; HRMS (ESI) m/z calcd for C$_{24}$H$_{20}$N$_3$O$_3$S [M+H$^+$] 430.1220, found 430.1223.

Example 54

(R)-N-(1-(4-Bromophenyl)ethyl)-10-ethyl-11-oxo-10,11-dihydrodibenzo[b,f][1,4]thiazepine-8-carboxamide 5-(S)-oxide (Compound 49)

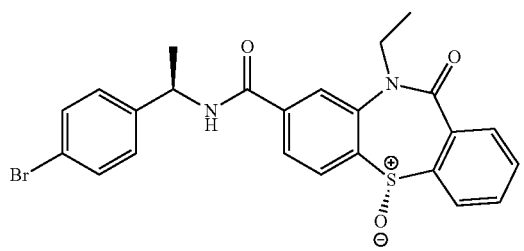 [SMILES: CCN1C(=O)c2ccccc2[S@+]([O-])c2ccc(C(=O)N[C@H](C)c3ccc(Br)cc3)cc21]

LCMS RT=6.02 min, m/z 497.0 [M+H$^+$]; HRMS (ESI) m/z calcd for C$_{24}$H$_{22}$BrN$_2$O$_3$S [M+H$^+$] 497.0529, found 497.0528.

Example 55

(R)-10-Ethyl-N-(1-(naphthalen-2-yl)ethyl)-11-oxo-10,11-dihydrodibenzo[b,f][1,4]thiazepine-8-carboxamide 5-(S)-oxide (Compound 50)

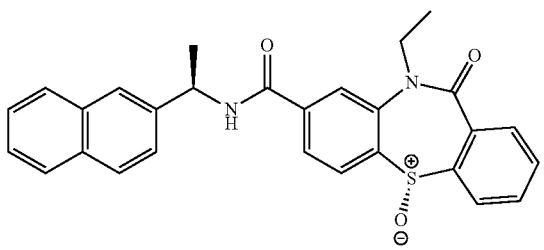 [SMILES: CCN1C(=O)c2ccccc2[S@+]([O-])c2ccc(C(=O)N[C@H](C)c3ccc4ccccc4c3)cc21]

LCMS RT=6.07 min, m/z 469.1 [M+H$^+$]; HRMS (ESI) m/z calcd for C$_{28}$H$_{25}$N$_2$O$_3$S [M+H$^+$] 469.1580, found 469.1586.

Example 56

N-(4-Chlorobenzyl)-10-methyl-11-oxo-10,11-dihydrodibenzo[b,f][1,4]thiazepine-8-carboxamide 5-(S)-oxide (Compound 51)

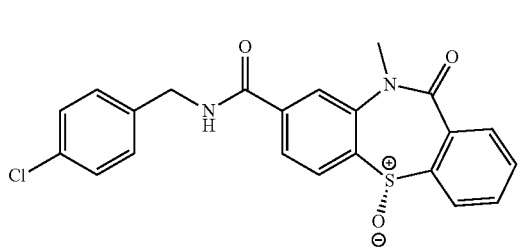

LCMS RT=5.47 min, m/z 425.1 [M+H$^+$]; HRMS (ESI) m/z calcd for C$_{22}$H$_{18}$ClN$_2$O$_3$S [M+H$^+$] 425.0721, found 425.0726.

Example 57

N-(4-bromobenzyl)-10-methyl-11-oxo-10,11-dihydrodibenzo[b,f][1,4]thiazepine-8-carboxamide 5-(S)-oxide (Compound 52)

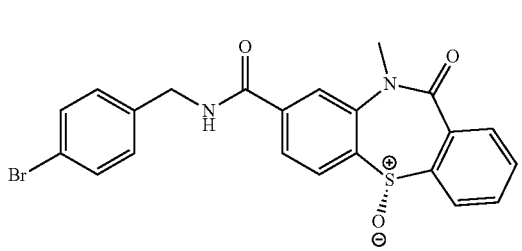 [SMILES: CN1C(=O)c2ccccc2[S@+]([O-])c2ccc(C(=O)NCc3ccc(Cl)cc3)cc21]

LCMS RT=5.57 min, m/z 469.0 [M+H⁺]; HRMS (ESI) m/z calcd for $C_{22}H_{18}BrN_2O_3S$ [M+H⁺] 469.0216, found 469.0215.

Example 58

10-Methyl-11-oxo-N-(pyridin-3-ylmethyl)-10,11-dihydrodibenzo[b,f][1,4]thiazepine-8-carboxamide 5-(S)-oxide (Compound 53)

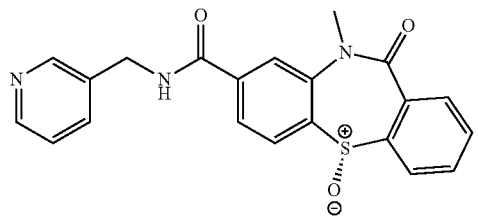 [SMILES: CN1C(=O)c2ccccc2[S@+]([O-])c2ccc(C(=O)NCc3cccnc3)cc21]

LCMS RT=3.35 min, m/z 392.1 [M+H⁺]; HRMS (ESI) m/z calcd for $C_{21}H_{18}N_3O_3S$ [M+H⁺] 392.1063, found 392.1067.

Example 59

10-Methyl-11-oxo-N-(2-(pyrrolidin-1-yl)ethyl)-10,11-dihydrodibenzo[b,f][1,4]thiazepine-8-carboxamide 5-(S)-oxide (Compound 54)

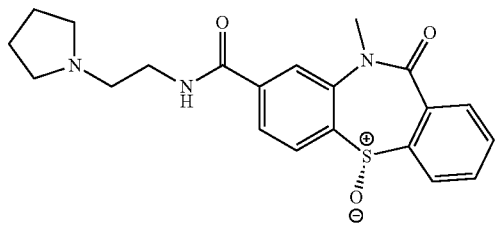 [SMILES: CN1C(=O)c2ccccc2[S@+]([O-])c2ccc(C(=O)NCCN3CCCC3)cc21]

LCMS RT=3.36 min, m/z 398.1 [M+H⁺]; HRMS (ESI) m/z calcd for $C_{21}H_{24}N_3O_3S$ [M+H⁺] 398.1533, found 398.1537.

Example 60

10-Ethyl-11-oxo-N-(2-(thiophen-2-yl)ethyl)-10,11-dihydrodibenzo[b,f][1,4]thiazepine-8-carboxamide 5-oxide

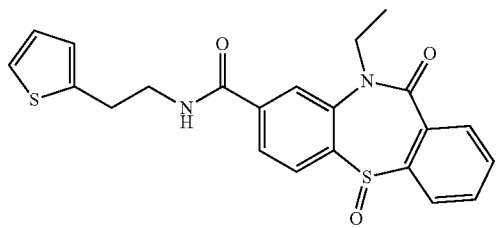 [SMILES: CCN1C(=O)c2ccccc2S(=O)c2ccc(C(=O)NCCc3cccs3)cc21]

The title compound was prepared according to the general protocol A. ¹H NMR (400 MHz, DMSO-d₆) δ ppm 8.76 (t, J=6.1 Hz, 1 H), 7.93 (d, J=1.4 Hz, 1 H), 7.86 (dd, J=8.1, 0.9 Hz, 1 H), 7.60-7.72 (m, 4 H), 7.50-7.57 (m, 1 H), 7.30 (dd, J=5.8, 1.1 Hz, 1 H), 6.91 (dd, J=5.1, 3.3 Hz, 1 H), 6.87 (d, J=3.5 Hz, 1 H), 4.47-4.61 (m, 1 H), 3.73 (td, J=13.8, 6.8 Hz, 1 H), 3.39-3.51 (m, 2 H), 3.01 (t, J=7.1 Hz, 2 H), 1.18 (t, J=7.1 Hz, 3 H); LCMS RT=5.27 min, m/z 425.1 [M+H⁺]; HRMS (ESI) m/z calcd for $C_{22}H_{21}N_2O_3S_2$ [M+H⁺] 425.0988, found 425.0988.

Example 61

10-Methyl-11-oxo-N-(2-(thiophen-2-yl)ethyl)-10,11-dihydrodibenzo[b,f][1,4]thiazepine-8-carboxamide 5-(S)-oxide (Compound 55)

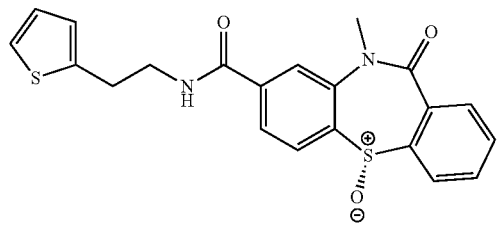 [SMILES: CN1C(=O)c2ccccc2[S@+]([O-])c2ccc(C(=O)NCCc3cccs3)cc21]

LCMS RT=5.08 min, m/z 411.0 [M+H⁺]; HRMS (ESI) m/z calcd for $C_{21}H_{19}N_2O_3S_2$ [M+H⁺] 411.0832, found 411.0831.

Example 62

Benzyl 10-benzyl-11-oxo-10,11-dihydrodibenzo[b,f][1,4]thiazepine-8-carboxylate 5-oxide

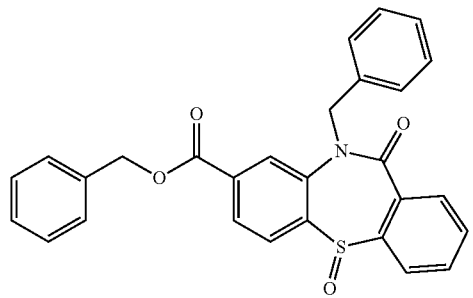 [SMILES: O=C(OCc1ccccc1)c1ccc2c(c1)N(Cc1ccccc1)C(=O)c1ccccc1S2=O]

A suspension of benzyl 10-benzyl-11-oxo-10,11-dihydrodibenzo[b,f][1,4]thiazepine-8-carboxylate (30.0 mg, 0.066 mmol) in acetic acid (3.00 mL) was treated at room temperature with H₂O₂ (0.17 mL, 1.66 mmol). The reaction mixture was stirred at room temperature for overnight. The mixture was poured into ice water and the precipitation was filtered, washed and dried to the title compound 21.0 mg (68%) as a white solid. ¹H NMR (400 MHz, DMSO-d₆) δ ppm 8.13 (d, J=1.6 Hz, 1 H), 7.95 (dd, J=8.2, 1.6 Hz, 1 H), 7.53-7.81 (m, 5 H), 7.24-7.43 (m, 9 H), 7.16-7.24 (m, 1 H), 5.64 (d, J=15.3 Hz, 1H), 5.30 (s, 2 H), 5.03 (d, J=15.3 Hz, 1 H); LCMS RT=6.61 min, m/z 468.1 [M+H⁺]; HRMS (ESI) m/z calcd for $C_{28}H_{22}NO_4S$ [M+H⁺] 468.1264, found 468.1263.

Example 63

N-(4-Methoxybenzyl)-11-oxo-10,11-dihydrodibenzo[b,f][1,4]thiazepine-8-carboxamide

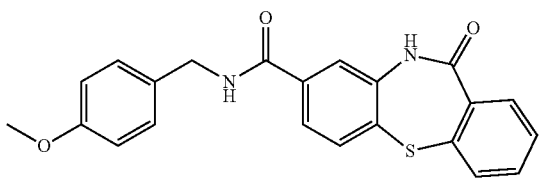 [SMILES: COc1ccc(CNC(=O)c2ccc3c(c2)NC(=O)c2ccccc2S3)cc1]

The title compound was prepared according to the general protocol B. $^1$H NMR (400 MHz, DMSO-d$_6$) δ ppm 10.74 (s, 1 H), 8.98 (t, J=5.7 Hz, 1 H), 7.55-7.72 (m, 4 H), 7.37-7.54 (m, 3 H), 7.13-7.22 (m, 2 H), 6.79-6.87 (m, 2 H), 4.33 (d, J=5.9 Hz, 2 H), 3.68 (s, 3 H); LCMS RT=5.31 min, m/z 391.1 [M+H$^+$]; HRMS (ESI) m/z calcd for C$_{22}$H$_{19}$N$_2$O$_3$S [M+H$^+$] 391.1111, found 391.1098.

Example 64

10-Ethyl-11-oxo-N-(3-(trifluoromethyl)benzyl)-10,11-dihydrodibenzo[b,f][1,4]thiazepine-8-carboxamide 5-oxide

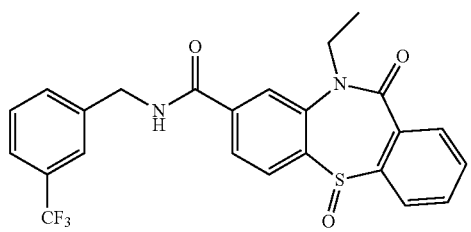 [SMILES: CCN1C(=O)c2ccccc2S(=O)c2ccc(C(=O)NCc3cccc(C(F)(F)F)c3)cc21]

The title compound was prepared according to the general protocol A. $^1$H NMR (400 MHz, DMSO-d$_6$) δ ppm 9.24 (t, J=6.1 Hz, 1 H), 8.02 (d, J=1.4 Hz, 1 H), 7.93 (dd, J=8.0, 1.6 Hz, 1 H), 7.66-7.74 (m, 3 H), 7.49-7.66 (m, 6 H), 4.43-4.65 (m, 3 H), 3.74 (dq, J=13.8, 7.0 Hz, 1 H), 1.18 (t, J=7.1 Hz, 3 H); $^{19}$F NMR (376 MHz, DMSO-d$_6$) δ ppm −61.04 (s, 3 F); LCMS RT=5.78 min, m/z 473.1 [M+H$^+$]; HRMS (ESI) m/z calcd for C$_{24}$H$_{20}$F$_3$N$_2$O$_3$S [M+H$^+$] 473.1141, found 473.1146.

Example 65

10-Ethyl-N-(3-methylbenzyl)-11-oxo-10,11-dihydrodibenzo[b,f][1,4]thiazepine-8-carboxamide 5-oxide

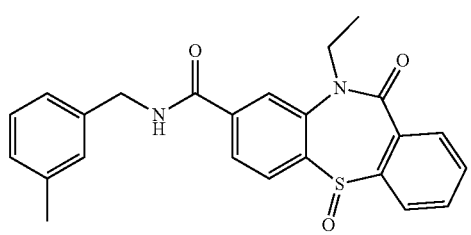 [SMILES: CCN1C(=O)c2ccccc2S(=O)c2ccc(C(=O)NCc3cccc(C)c3)cc21]

The title compound was prepared according to the general protocol A. $^1$H NMR (400 MHz, DMSO-d$_6$) δ ppm 9.12 (t, J=6.0 Hz, 1 H), 8.01 (d, J=1.4 Hz, 1 H), 7.93 (dd, J=8.0, 1.6 Hz, 1 H), 7.66-7.74 (m, 3 H), 7.61-7.65 (m, 1 H), 7.55 (ddd, J=7.9, 7.0, 1.4 Hz, 1 H), 7.17 (t, J=7.5 Hz, 1 H), 6.98-7.12 (m, 3 H), 4.50-4.62 (m, 1 H), 4.32-4.48 (m, 2 H), 3.75 (dq, J=13.9, 7.0 Hz, 1 H), 2.25 (s, 3 H), 1.18 (t, J=7.1 Hz, 3 H); LCMS RT=5.54 min, m/z 419.1 [M+H$^+$]; HRMS (ESI) m/z calcd for C$_{24}$H$_{23}$N$_2$O$_3$S [M+H$^+$] 419.1424, found 419.1427.

Example 66

N-(3-Chlorobenzyl)-10-ethyl-11-oxo-10,11-dihydrodibenzo[b,f][1,4]thiazepine-8-carboxamide 5-oxide

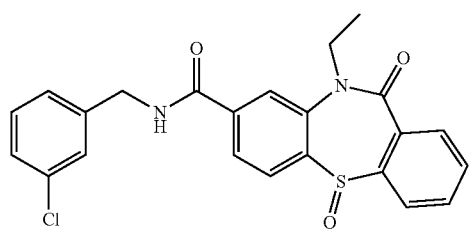

The title compound was prepared according to the general protocol A. $^1$H NMR (400 MHz, DMSO-d$_6$) δ ppm 9.18 (t, J=6.0 Hz, 1 H), 8.02 (d, J=1.4 Hz, 1 H), 7.93 (dd, J=8.2, 1.6 Hz, 1 H), 7.66-7.74 (m, 3 H), 7.61-7.66 (m, 1 H), 7.55 (td, J=7.4, 1.4 Hz, 1 H), 7.22-7.37 (m, 4 H), 4.51-4.62 (m, 1 H), 4.37-4.51 (m, 2 H), 3.75 (dq, J=13.9, 7.0 Hz, 1H), 1.18 (t, J=7.1 Hz, 3 H); LCMS RT=5.64 min, m/z 439.1 [M+H$^+$]; HRMS (ESI) m/z calcd for C$_{23}$H$_{20}$ClN$_2$O$_3$S [M+H$^+$] 439.0878, found 439.0882.

Example 67

N-(Biphenyl-3-ylmethyl)-10-ethyl-11-oxo-10,11-dihydrodibenzo[b,f][1,4]thiazepine-8-carboxamide 5-oxide

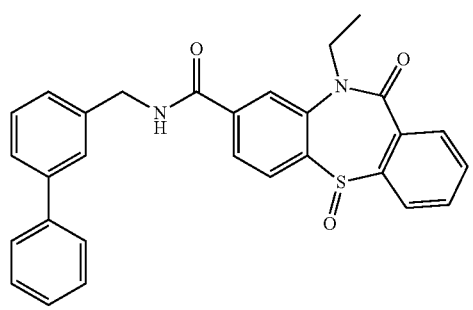 [SMILES: CCN1C(=O)c2ccccc2S(=O)c2ccc(C(=O)NCc3cccc(-c4ccccc4)c3)cc21]

The title compound was prepared according to the general protocol A. $^1$H NMR (400 MHz, DMSO-d$_6$) δ ppm 9.18 (t, J=5.9 Hz, 1 H), 8.03 (d, J=1.4 Hz, 1 H), 7.94 (dd, J=8.2, 1.6 Hz, 1 H), 7.25-7.76 (m, 14 H), 4.37-4.70 (m, 3 H), 3.75 (dd, J=13.8, 6.9 Hz, 1H), 1.18 (t, J=7.0 Hz, 3 H); LCMS RT=6.10 min, m/z 481.1 [M+H$^+$]; HRMS (ESI) m/z calcd for C$_{29}$H$_{25}$N$_2$O$_3$S [M+H$^+$] 481.1580, found 481.1581.

Example 68

10-Ethyl-11-oxo-N-(3-phenylpropyl)-10,11-dihydrodibenzo[b,f][1,4]thiazepine-8-carboxamide 5-oxide

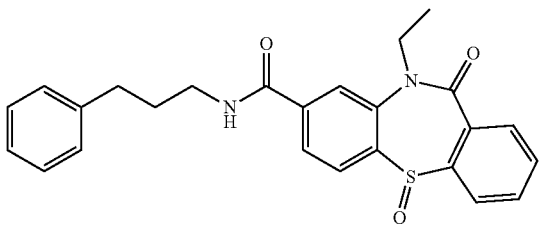 [SMILES: CCN1C(=O)c2ccccc2S(=O)c2ccc(C(=O)NCCCc3ccccc3)cc21]

The title compound was prepared according to the general protocol A. $^1$H NMR (400 MHz, DMSO-$d_6$) δ ppm 8.58 (t, J=5.8 Hz, 1 H), 7.93 (d, J=1.4 Hz, 1 H), 7.87 (dd, J=8.2, 1.6 Hz, 1 H), 7.64-7.73 (m, 3 H), 7.61-7.64 (m, 1 H), 7.55 (ddd, J=7.9, 7.0, 1.4 Hz, 1 H), 7.21-7.28 (m, 2 H), 7.10-7.21 (m, 3 H), 4.48-4.62 (m, 1 H), 3.67-3.82 (m, 1 H), 3.15-3.28 (m, 2 H), 2.55-2.62 (m, 2 H), 1.78 (ddd, J=14.9, 7.4, 7.2 Hz, 2 H), 1.18 (t, J=7.0 Hz, 3 H); LCMS RT=5.65 min, m/z 433.1 [M+H$^+$]; HRMS (ESI) m/z calcd for $C_{25}H_{25}N_2O_3S$ [M+H$^+$] 433.1580, found 433.1586.

Example 69

N-(2,3-Dimethoxybenzyl)-10-ethyl-11-oxo-10,11-dihydrodibenzo[b,f][1,4]thiazepine-8-carboxamide 5-oxide

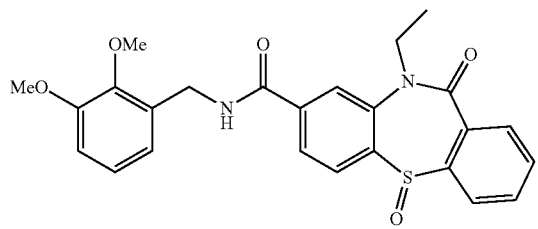 [SMILES: CCN1C(=O)c2ccccc2S(=O)c2ccc(C(=O)NCc3cccc(OC)c3OC)cc21]

The title compound was prepared according to the general protocol A. $^1$H NMR (400 MHz, DMSO-$d_6$) δ ppm 9.01 (t, J=5.9 Hz, 1 H), 8.01 (d, J=1.4 Hz, 1 H), 7.93 (dd, J=8.2, 1.6 Hz, 1 H), 7.66-7.74 (m, 3 H), 7.60-7.65 (m, 1 H), 7.55 (ddd, J=7.9, 7.0, 1.4 Hz, 1 H), 6.86-7.02 (m, 2 H), 6.81 (dd, J=7.6, 1.8 Hz, 1 H), 4.50-4.62 (m, 1 H), 4.37-4.50 (m, 2 H), 3.77 (s, 3 H), 3.72 (s, 3 H), 3.68-3.80 (m, 1 H), 1.18 (t, J=7.1 Hz, 3 H); LCMS RT=5.26 min, m/z 465.1 [M+H$^+$]; HRMS (ESI) m/z calcd for $C_{25}H_{25}N_2O_5S$ [M+H$^+$] 465.1479, found 465.1481.

Example 70

10-Ethyl-11-oxo-N-(thiophen-2-ylmethyl)-10,11-dihydrodibenzo[b,f][1,4]thiazepine-8-carboxamide 5-oxide

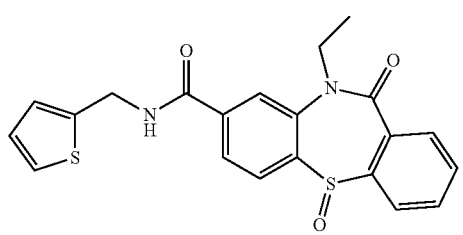 [SMILES: CCN1C(=O)c2ccccc2S(=O)c2ccc(C(=O)NCc3ccco3)cc21]

The title compound was prepared according to the general protocol A. $^1$H NMR (400 MHz, DMSO-$d_6$) δ ppm 9.25 (t, J=6.0 Hz, 1 H), 7.98 (d, J=1.6 Hz, 1 H), 7.90 (dd, J=8.0, 1.4 Hz, 1 H), 7.66-7.73 (m, 3 H), 7.59-7.64 (m, 1 H), 7.54 (td, J=7.3, 1.3 Hz, 1 H), 7.35 (dd, J=4.5, 1.2 Hz, 1 H), 6.99 (d, J=4.1 Hz, 1 H), 6.92 (dd, J=5.1, 3.3 Hz, 1 H), 4.46-4.70 (m, 3 H), 3.65-3.79 (m, 1 H), 1.17 (t, J=7.1 Hz, 3 H); LCMS RT=5.13 min, m/z 411.1 [M+H$^+$]; HRMS (ESI) m/z calcd for $C_{21}H_{19}N_2O_3S_2$ [M+H$^+$] 411.0832, found 411.0828.

Example 71

10-Ethyl-N-(furan-2-ylmethyl)-11-oxo-10,11-dihydrodibenzo[b,f][1,4]thiazepine-8-carboxamide 5-oxide

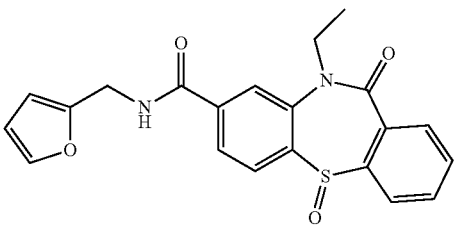

The title compound was prepared according to the general protocol A. $^1$H NMR (400 MHz, DMSO-$d_6$) δ ppm 9.09 (t, J=5.7 Hz, 1 H), 7.99 (d, J=1.6 Hz, 1 H), 7.90 (dd, J=8.2, 1.6 Hz, 1 H), 7.65-7.72 (m, 3 H), 7.61-7.64 (m, 1 H), 7.51-7.57 (m, 2 H), 6.36 (dd, J=3.1, 1.8 Hz, 1 H), 6.27 (dd, J=3.1, 0.8 Hz, 1 H), 4.56 (dq, J=13.9, 7.0 Hz, 1 H), 4.36-4.49 (m, 2 H), 3.74 (dq, J=13.9, 7.0 Hz, 1 H), 1.17 (t, J=7.1 Hz, 3 H); LCMS RT=4.92 min, m/z 395.1 [M+H$^+$]; HRMS (ESI) m/z calcd for $C_{21}H_{19}N_2O_4S$ [M+H$^+$] 395.1060, found 395.1071.

Example 72

10-Ethyl-N-((4-methylthiophen-2-yl)methyl)-11-oxo-10,11-dihydrodibenzo[b,f][1,4]thiazepine-8-carboxamide 5-oxide

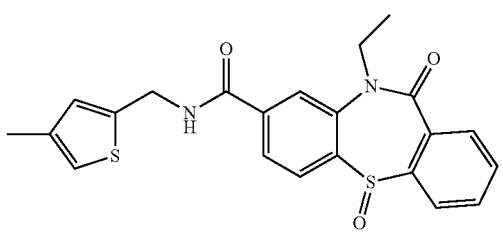 [SMILES: CCN1C(=O)c2ccccc2S(=O)c2ccc(C(=O)NCc3cc(C)cs3)cc21]

The title compound was prepared according to the general protocol A. $^1$H NMR (400 MHz, DMSO-$d_6$) δ ppm 9.21 (t, J=6.0 Hz, 1 H), 7.98 (d, J=1.6 Hz, 1 H), 7.90 (dd, J=8.2, 1.6 Hz, 1 H), 7.66-7.73 (m, 3 H), 7.61-7.65 (m, 1 H), 7.54 (ddd, J=7.9, 7.0, 1.4 Hz, 1 H), 6.88-6.94 (m, 1 H), 6.80 (d, J=1.0 Hz, 1 H), 4.42-4.69 (m, 3 H), 3.65-3.85 (dq, J=13.8, 7.1 Hz, 1 H), 2.12 (d, J=1.0 Hz, 3 H), 1.18 (t, J=7.1 Hz, 3 H); LCMS RT=5.44 min, m/z 425.1 [M+H$^+$]; HRMS (ESI) m/z calcd for $C_{22}H_2N_2O_3S_2$ [M+H$^+$] 425.0988, found 425.0993.

Example 73

10-Ethyl-N-(2-morpholinoethyl)-11-oxo-10,11-dihydrodibenzo[b,f][1,4]thiazepine-8-carboxamide 5-oxide

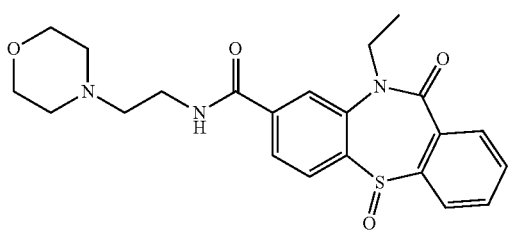 [SMILES: CCN1C(=O)c2ccccc2S(=O)c2ccc(C(=O)NCCN3CCOCC3)cc21]

The title compound was prepared according to the general protocol B. $^1$H NMR (400 MHz, DMSO-$d_6$) δ ppm 9.40 (br. s., 1 H), 8.83 (br. s., 1 H), 7.97 (d, J=1.4 Hz, 1H), 7.90 (dd, J=8.3, 1.1 Hz, 1 H), 7.67-7.76 (m, 2 H), 7.61-7.66 (m, 1 H), 7.55 (ddd, J=7.9, 6.9, 1.4 Hz, 1 H), 4.58 (td, J=14.1, 7.2 Hz, 2 H), 3.97 (d, J=12.3 Hz, 2 H), 3.72 (td, J=13.8, 6.9 Hz, 2 H), 3.59 (t, J=12.1 Hz, 4 H), 3.49 (d, J=11.2 Hz, 2 H), 3.03-3.18 (m, 2 H), 1.19 (t, J=7.1 Hz, 3 H); LCMS RT=3.48 min, m/z 428.1 [M+H$^+$]; HRMS (ESI) m/z calcd for $C_{22}H_{26}N_3O_4S$ [M+H$^+$] 428.1639, found 428.1644.

Example 74

10-Ethyl-N-((1-methylpiperidin-4-yl)methyl)-11-oxo-10,11-dihydrodibenzo[b,f][1,4]thiazepine-8-carboxamide 5-oxide

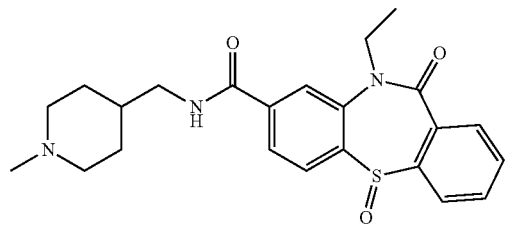 [SMILES: CCN1C(=O)c2ccccc2S(=O)c2ccc(C(=O)NCC3CCN(C)CC3)cc21]

The title compound was prepared according to the general protocol B. $^1$H NMR (400 MHz, DMSO-$d_6$) δ ppm 8.96 (br. s., 1 H), 8.67 (t, J=5.3 Hz, 1 H), 7.95 (d, J=1.6 Hz, 1 H), 7.88 (dd, J=8.2, 1.6 Hz, 1 H), 7.66-7.73 (m, 2 H), 7.60-7.66 (m, 1 H), 7.55 (ddd, J=7.9, 7.0, 1.4 Hz, 1 H), 4.58 (td, J=13.8, 6.7 Hz, 1 H), 3.73 (td, J=13.9, 6.8 Hz, 1 H), 3.34-3.43 (m, 2 H), 3.19 (ddd, J=12.8, 6.7, 6.5 Hz, 1 H), 3.09 (ddd, J=13.1, 6.5, 6.3 Hz, 1 H), 2.78-2.90 (m, 2 H), 2.71 (d, J=4.9 Hz, 3 H), 1.78-1.90 (m, 2 H), 1.70 (br. s., 1 H), 1.23-1.37 (m, 2 H), 1.18 (t, J=7.1 Hz, 3 H); LCMS RT=3.54 min, m/z 426.2 [M+H$^+$]; HRMS (ESI) m/z calcd for $C_{23}H_{28}N_3O_3S$ [M+H$^+$] 426.1846, found 426.1846.

Example 75

N-(2-Chlorobenzyl)-10-ethyl-11-oxo-10,11-dihydrodibenzo[b,f][1,4]thiazepine-8-carboxamide 5-oxide

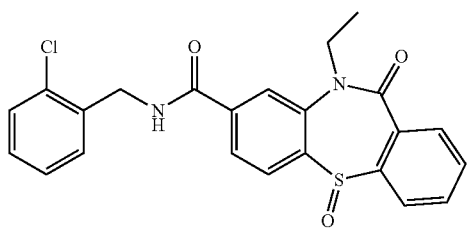

The title compound was prepared according to the general protocol A. $^1$H NMR (400 MHz, DMSO-$d_6$) δ ppm 9.16 (t, J=5.8 Hz, 1 H), 8.04 (d, J=1.6 Hz, 1 H), 7.95 (dd, J=8.2, 1.6 Hz, 1 H), 7.66-7.75 (m, 3 H), 7.61-7.66 (m, 1 H), 7.55 (ddd, J=7.9, 6.9, 1.5 Hz, 1 H), 7.38-7.46 (m, 1 H), 7.31-7.38 (m, 1 H), 7.23-7.31 (m, 2 H), 4.42-4.66 (m, 3 H), 3.76 (dq, J=13.8, 7.0 Hz, 1 H), 1.19 (t, J=7.1 Hz, 3 H); LCMS RT=5.56 min, m/z 439.0 [M+H$^+$]; HRMS (ESI) m/z calcd for $C_{23}H_{20}ClN_2O_3S$ [M+H$^+$] 439.0878, found 439.0884.

Example 76

10-Ethyl-11-oxo-N-(2-(trifluoromethyl)benzyl)-10,11-dihydrodibenzo[b,f][1,4]thiazepine-8-carboxamide 5-oxide

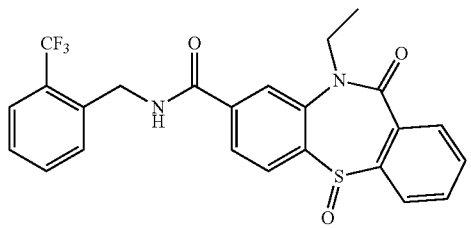 [SMILES: CCN1C(=O)c2ccccc2S(=O)c2ccc(C(=O)NCc3ccccc3C(F)(F)F)cc21]

The title compound was prepared according to the general protocol A. $^1$H NMR (400 MHz, DMSO-$d_6$) δ ppm 9.23 (t, J=5.8 Hz, 1 H), 8.05 (d, J=1.6 Hz, 1 H), 7.96 (dd, J=8.2, 1.6 Hz, 1 H), 7.67-7.74 (m, 3 H), 7.41-7.67 (m, 6 H), 4.50-4.72 (m, 3 H), 3.76 (dq, J=13.8, 7.1 Hz, 1 H), 1.19 (t, J=7.1 Hz, 3 H); $^{19}$F NMR (376 MHz, DMSO-$d_6$) δ ppm −58.98 (s, 3 F); LCMS RT=5.77 min, m/z 473.1 [M+H$^+$]; HRMS (ESI) m/z calcd for $C_{24}H_{20}F_3N_2O_3S$ [M+H$^+$] 473.1141, found 473.1149.

Example 77

N-(2,3-Dihydrobenzo[b][1,4]dioxin-6-yl)-10-ethyl-11-oxo-10,11-dihydrodibenzo[b,f][1,4]thiazepine-8-carboxamide 5-oxide

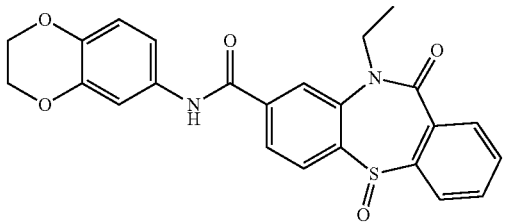 [SMILES: CCN1C(=O)c2ccccc2S(=O)c2ccc(C(=O)Nc3ccc4c(c3)OCCO4)cc21]

The title compound was prepared according to the general protocol A. $^1$H NMR (400 MHz, DMSO-d$_6$) δ ppm 10.15 (s, 1 H), 8.05 (d, J=1.6 Hz, 1 H), 7.94 (dd, J=8.2, 1.6 Hz, 1 H), 7.67-7.75 (m, 3 H), 7.62-7.67 (m, 1 H), 7.56 (td, J=7.4, 1.4 Hz, 1 H), 7.29 (d, J=2.5 Hz, 1 H), 7.10 (dd, J=8.8, 2.3 Hz, 1 H), 6.80 (d, J=8.8 Hz, 1 H), 4.59 (dq, J=14.0, 7.1 Hz, 1 H), 4.14-4.27 (m, 4 H), 3.78 (dq, J=13.8, 7.1 Hz, 1 H), 1.19 (t, J=7.1 Hz, 3 H); LCMS RT=5.25 min, m/z 449.1 [M+H$^+$]; HRMS (ESI) m/z calcd for C$_{24}$H$_{21}$N$_2$O$_5$S [M+H$^+$] 449.1166, found 449.1173.

Example 78

10-Ethyl-N-(2-methylbenzyl)-11-oxo-10,11-dihydrodibenzo[b,f][1,4]thiazepine-8-carboxamide 5-oxide

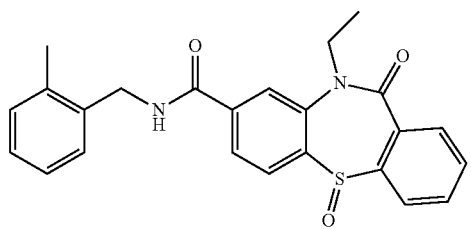

The title compound was prepared according to the general protocol A. $^1$H NMR (400 MHz, DMSO-d$_6$) δ ppm 9.00 (t, J=5.9 Hz, 1 H), 8.01 (d, J=1.2 Hz, 1 H), 7.93 (dd, J=7.8, 1.2 Hz, 1 H), 7.65-7.73 (m, 3 H), 7.60-7.65 (m, 1 H), 7.54 (td, J=7.6, 1.1 Hz, 1 H), 7.16-7.22 (m, 1 H), 7.06-7.16 (m, 3 H), 4.55 (dq, J=14.0, 7.1 Hz, 1 H), 4.33-4.48 (m, 2H), 3.74 (dq, J=14.0, 7.0 Hz, 1 H), 2.27 (s, 3 H), 1.17 (t, J=7.1 Hz, 3 H); LCMS RT=5.49 min, m/z 419.1 [M+H$^+$]; HRMS (ESI) m/z calcd for C$_{24}$H$_{23}$N$_2$O$_3$S [M+H$^+$] 419.1424, found 419.1422.

Example 79

N-(2,5-Dimethoxybenzyl)-10-ethyl-11-oxo-10,11-dihydrodibenzo[b,f][1,4]thiazepine-8-carboxamide 5-oxide

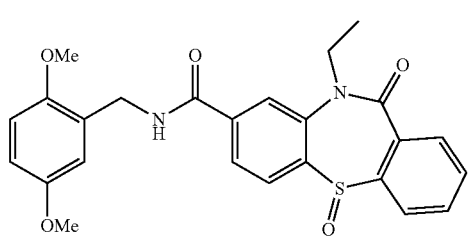 [SMILES: CCN1C(=O)c2ccccc2S(=O)c2ccc(C(=O)NCc3cc(OC)ccc3OC)cc21]

The title compound was prepared according to the general protocol A. $^1$H NMR (400 MHz, DMSO-d$_6$) δ ppm 8.95 (t, J=5.8 Hz, 1 H), 8.01 (d, J=1.4 Hz, 1 H), 7.93 (dd, J=8.1, 1.1 Hz, 1 H), 7.65-7.73 (m, 3 H), 7.59-7.65 (m, 1 H), 7.54 (td, J=7.5, 0.9 Hz, 1 H), 6.88 (d, J=8.8 Hz, 1 H), 6.69-6.79 (m, 2 H), 4.55 (dq, J=13.8, 7.0 Hz, 1 H), 4.27-4.44 (m, 2H), 3.72 (s, 3 H), 3.68-3.84 (m, 1 H), 3.62 (s, 3 H), 1.18 (t, J=7.0 Hz, 3 H); LCMS RT=5.32 min, m/z 465.1 [M+H$^+$]; HRMS (ESI) m/z calcd for C$_{25}$H$_{25}$N$_2$O$_5$S [M+H$^+$] 465.1479, found 465.1472.

Example 80

N-((1H-Indol-6-yl)methyl)-10-ethyl-11-oxo-10,11-dihydrodibenzo[b,f][1,4]thiazepine-8-carboxamide 5-oxide

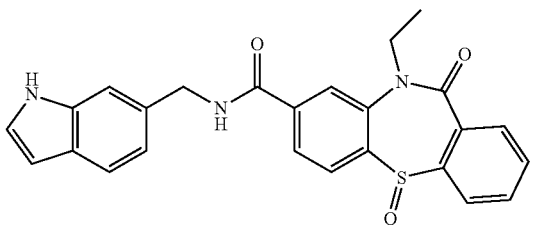 [SMILES: CCN1C(=O)c2ccccc2S(=O)c2ccc(C(=O)NCc3ccc4cc[nH]c4c3)cc21]

The title compound was prepared according to the general protocol A. $^1$H NMR (400 MHz, DMSO-d$_6$) δ ppm 10.98 (br. s., 1 H), 9.08 (t, J=6.0 Hz, 1 H), 8.01 (d, J=1.4 Hz, 1 H), 7.93 (dd, J=8.2, 1.2 Hz, 1 H), 7.64-7.73 (m, 3 H), 7.59-7.64 (m, 1 H), 7.53 (td, J=7.4, 1.1 Hz, 1 H), 7.43 (s, 1 H), 7.23-7.31 (m, 2 H), 7.01 (dd, J=8.3, 1.5 Hz, 1 H), 6.33 (t, J=2.5 Hz, 1 H), 4.40-4.63 (m, 3 H), 3.73 (dq, J=13.8, 7.0 Hz, 1 H), 1.16 (t, J=7.0 Hz, 3 H); LCMS RT=5.07 min, m/z 444.1 [M+H$^+$]; HRMS (ESI) m/z calcd for C$_{25}$H$_{22}$N$_3$O$_3$S [M+H$^+$] 444.1376, found 444.1368.

Example 81

N-(2,4-Dimethoxybenzyl)-10-ethyl-11-oxo-10,11-dihydrodibenzo[b,f][1,4]thiazepine-8-carboxamide 5-oxide

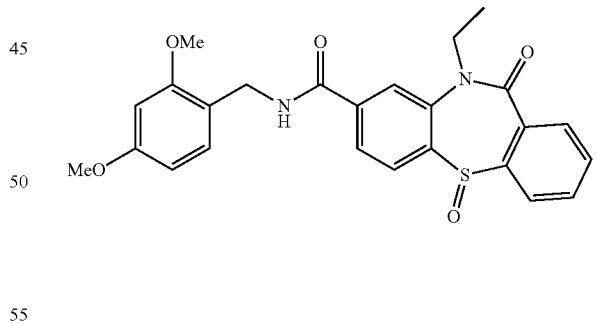

The title compound was prepared according to the general protocol A. $^1$H NMR (400 MHz, DMSO-d$_6$) δ ppm 8.87 (t, J=5.6 Hz, 1 H), 8.00 (d, J=1.4 Hz, 1 H), 7.91 (dd, J=8.2, 1.0 Hz, 1 H), 7.59-7.72 (m, 4 H), 7.54 (td, J=7.3, 1.1 Hz, 1 H), 7.06 (d, J=8.4 Hz, 1H), 6.52 (d, J=2.3 Hz, 1 H), 6.42 (dd, J=8.3, 2.4 Hz, 1 H), 4.48-4.63 (m, 1 H), 4.24-4.38 (m, 2 H), 3.75 (s, 3 H), 3.70 (s, 3 H), 3.68-3.81 (m, 1 H), 1.17 (t, J=7.1 Hz, 3 H); LCMS RT=5.35 min, m/z 465.1 [M+H$^+$]; HRMS (ESI) m/z calcd for C$_{25}$H$_{25}$N$_2$O$_5$S [M+H$^+$] 465.1479, found 465.1456.

Example 82

N-(4-Cyanobenzyl)-10-ethyl-11-oxo-10,11-dihydrodibenzo[b,f][1,4]thiazepine-8-carboxamide 5-(R)-oxide

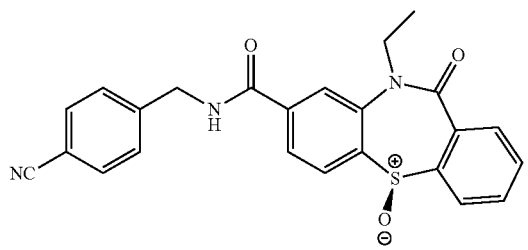 [SMILES: CCN1C(=O)c2ccccc2[S@@+]([O-])c2ccc(C(=O)NCc3ccc(C#N)cc3)cc21]

Separation of enantiomers via chiral HPLC: Analytical analysis was performed on a CHIRALAPK® AS® column (4.6×250 mm, 5 micron). The mobile phase was 100% of methanol at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=5.95 minutes; positive optical rotation. The second eluting peak: RT=9.08 minutes; negative optical rotation. Preparative separation was performed on a CHIRALAPK®AS® column (5×50 cm, 20 micron). The mobile phase was 100% of methanol at a flow rate of 35 mL/min. Fraction collection was triggered by UV absorbance (254 nm). LCMS RT=5.13 min, m/z 430.0 [M+H$^+$]; HRMS (ESI) m/z calcd for $C_{24}H_{20}N_3O_3S$ [M+H$^+$] 430.1220, found 430.1223.

Example 83

N-(2,6-dimethoxybenzyl)-10-ethyl-11-oxo-10,11-dihydrodibenzo[b,f] [1,4] thiazepine-8-carboxamide 5-oxide

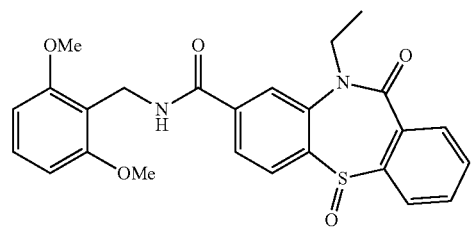 [SMILES: CCN1C(=O)c2ccccc2S(=O)c2ccc(C(=O)NCc3c(OC)cccc3OC)cc21]

The title compound was prepared according to the general protocol A. $^1$H NMR (400 MHz, DMSO-d$_6$) δ ppm 8.32 (t, J=4.2 Hz, 1 H), 7.92 (d, J=1.4 Hz, 1 H), 7.87 (dd, J=8.0, 1.2 Hz, 1 H), 7.64-7.73 (m, 2 H), 7.58-7.64 (m, 2 H), 7.53 (td, J=7.4, 1.3 Hz, 1 H), 7.23 (t, J=8.4 Hz, 1 H), 6.63 (d, J=8.4 Hz, 2 H), 4.52 (td, J=13.8, 6.7 Hz, 1 H), 4.39 (dd, J=4.3, 2.2 Hz, 2 H), 3.72 (s, 6 H), 3.63-3.80 (m, 1 H), 1.15 (t, J=7.1 Hz, 3 H); LCMS RT=5.42 min, m/z 465.1 [M+H$^+$]; HRMS (ESI) m/z calcd for $C_{25}H_{25}N_2O_5S$ [M+H$^+$] 465.1479, found 465.1480.

Example 84

10-Ethyl-N-(4-fluorobenzyl)-11-oxo-10,11-dihydrodibenzo[b,f][1,4]thiazepine-8-carboxamide 5-(R)-oxide

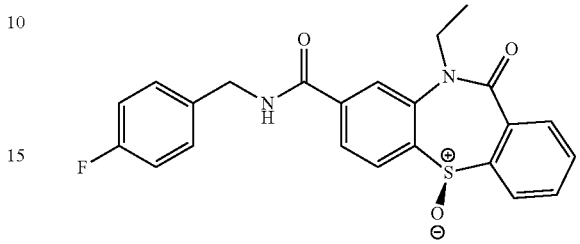

Separation of enantiomers via chiral HPLC: Analytical analysis was performed on a CHIRALCEL®OJ® column (4.6×250 mm, 5 micron). The mobile phase was 100% of methanol at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=6.26 minutes; negative optical rotation. The second eluting peak: RT=6.86 minutes; positive optical rotation. Preparative separation was performed on a CHIRALCEL®OJ® column (5×50 cm, 20 micron). The mobile phase was 100% of methanol at a flow rate of 35 mL/min. Fraction collection was triggered by UV absorbance (254 nm). LCMS RT=5.43 min, m/z 423.1 [M+H$^+$]; HRMS (ESI) m/z calcd for $C_{23}H_{20}FN_2O_3S$ [M+H$^+$] 423.1173, found 423.1179.

Example 85

10-Ethyl-N-isobutyl-11-oxo-10,11-dihydrodibenzo[b,f][1,4]thiazepine-8-carboxamide 5-oxide

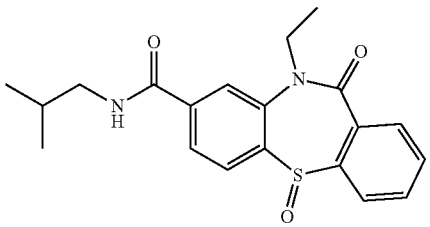 [SMILES: CCN1C(=O)c2ccccc2S(=O)c2ccc(C(=O)NCC(C)C)cc21]

The title compound was prepared according to the general protocol A. $^1$H NMR (400 MHz, DMSO-d$_6$) δ ppm 8.56 (t, J=5.9 Hz, 1 H), 7.95 (d, J=1.4 Hz, 1 H), 7.87 (dd, J=8.1, 1.3 Hz, 1 H), 7.59-7.72 (m, 4 H), 7.54 (td, J=7.5, 1.3 Hz, 1 H), 4.55 (dq, J=14.1, 7.1 Hz, 1 H), 3.74 (dq, J=13.8, 7.1 Hz, 1 H), 2.92-3.13 (m, 2 H), 1.77 (tt, J=13.5, 6.8 Hz, 1 H), 1.17 (t, J=7.1 Hz, 3 H), 0.84 (d, J=6.7 Hz, 6 H); LCMS RT=5.06 min, m/z 371.1 [M+H$^+$]; HRMS (ESI) m/z calcd for $C_{20}H_{23}N_2O_3S$ [M+H$^+$] 371.1424, found 371.1429.

Example 86

10-Ethyl-N-(4-methylphenethyl)-11-oxo-10,11-dihydrodibenzo[b,f][1,4]thiazepine-8-carboxamide 5-oxide

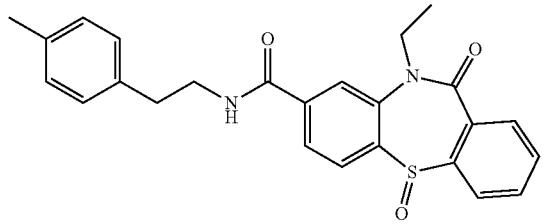 [SMILES: CCN1C(=O)c2ccccc2S(=O)c2ccc(C(=O)NCCc3ccc(C)cc3)cc21]

The title compound was prepared according to the general protocol A. $^1$H NMR (400 MHz, DMSO-d$_6$) δ ppm 8.66 (t, J=5.5 Hz, 1 H), 7.90 (d, J=1.4 Hz, 1 H), 7.84 (dd, J=8.1, 1.1 Hz, 1 H), 7.60-7.72 (m, 4 H), 7.54 (td, J=7.4, 1.4 Hz, 1 H), 7.03-7.10 (m, 4 H), 4.54 (dq, J=14.0, 7.1 Hz, 1 H), 3.72 (dddd, J=13.7, 7.2, 7.1, 6.9 Hz, 1 H), 3.35-3.48 (m, 2 H), 2.73 (t, J=7.3 Hz, 2 H), 2.23 (s, 3 H), 1.18 (t, J=7.0 Hz, 3 H); LCMS RT=5.67 min, m/z 433.2 [M+H$^+$]; HRMS (ESI) m/z calcd for C$_{25}$H$_{25}$N$_2$O$_3$S [M+H$^+$] 433.1580, found 433.1581.

Example 87

10-Ethyl-11-oxo-N-(4-phenylbutyl)-10,11-dihydrodibenzo[b,f][1,4]thiazepine-8-carboxamide 5-oxide

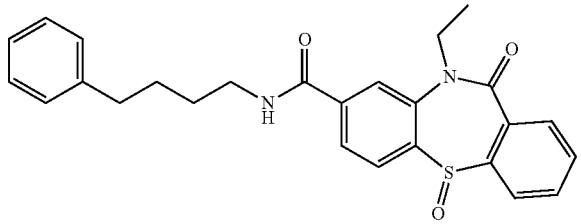 [SMILES: CCN1C(=O)c2ccccc2S(=O)c2ccc(C(=O)NCCCCc3ccccc3)cc21]

The title compound was prepared according to the general protocol A. $^1$H NMR (400 MHz, DMSO-d$_6$) δ ppm 8.56 (t, J=5.7 Hz, 1 H), 7.93 (d, J=1.6 Hz, 1 H), 7.85 (dd, J=8.2, 1.4 Hz, 1 H), 7.59-7.75 (m, 4 H), 7.54 (td, J=7.4, 1.3 Hz, 1 H), 7.19-7.26 (m, 2 H), 7.08-7.18 (m, 3 H), 4.55 (dq, J=14.0, 7.1 Hz, 1 H), 3.72 (dq, J=13.9, 7.0 Hz, 1 H), 3.15-3.27 (m, 2 H), 2.55 (t, J=7.3 Hz, 2 H), 1.51-1.62 (m, 2 H), 1.42-1.51 (m, 2 H), 1.17 (t, J=7.0 Hz, 3 H); LCMS RT=5.91 min, m/z 447.2 [M+H$^+$]; HRMS (ESI) m/z calcd for C$_{26}$H$_{27}$N$_2$O$_3$S [M+H$^+$] 447.1737, found 447.1737.

Example 88

10-Ethyl-N-(2-(furan-2-yl)propyl)-11-oxo-10,11-dihydrodibenzo[b,f][1,4]thiazepine-8-carboxamide 5-oxide

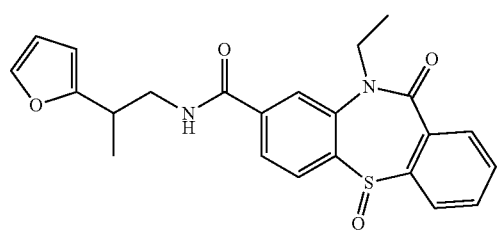 [SMILES: CCN1C(=O)c2ccccc2S(=O)c2ccc(C(=O)NCC(C)c3ccco3)cc21]

The title compound was prepared according to the general protocol A. LCMS RT=5.21 min, m/z 423.1 [M+H$^+$]; HRMS (ESI) m/z calcd for C$_{23}$H$_{23}$N$_2$O$_4$S [M+H$^+$] 423.1373, found 423.1381.

Example 89

N-((1H-Imidazol-2-yl)methyl)-10-ethyl-11-oxo-10,11-dihydrodibenzo[b,f][1,4]thiazepine-8-carboxamide 5-oxide

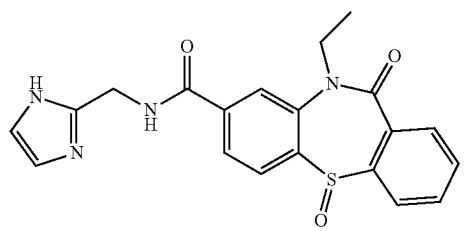 [SMILES: CCN1C(=O)c2ccccc2S(=O)c2ccc(C(=O)NCc3ncc[nH]3)cc21]

The title compound was prepared according to the general protocol B. $^1$H NMR (400 MHz, DMSO-d$_6$) δ ppm 11.75 (br. s., 1 H), 9.11 (t, J=5.7 Hz, 1 H), 8.02 (d, J=1.4 Hz, 1 H), 7.93 (dd, J=8.3, 1.3 Hz, 1 H), 7.69 (t, J=7.7 Hz, 3 H), 7.59-7.65 (m, 1 H), 7.54 (td, J=7.5, 1.3 Hz, 1 H), 6.97 (s, 1 H), 6.77 (s, 1 H), 4.56 (td, J=13.9, 7.0 Hz, 1 H), 4.36-4.51 (m, 2 H), 3.74 (td, J=13.9, 6.7 Hz, 1 H), 1.18 (t, J=7.1 Hz, 3 H); LCMS RT=3.43 min, m/z 395.1 [M+H$^+$]; HRMS (ESI) m/z calcd for C$_{20}$H$_{19}$N$_4$O$_3$S [M+H$^+$] 395.1172, found 395.1180.

Example 90

10-Ethyl-N-(2-(2-methylthiazol-4-yl)ethyl)-11-oxo-10,11-dihydrodibenzo[b,f][1,4]thiazepine-8-carboxamide 5-oxide

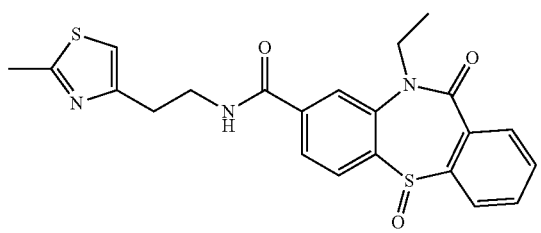 [SMILES: CCN1C(=O)c2ccccc2S(=O)c2ccc(C(=O)NCCc3csc(C)n3)cc21]

The title compound was prepared according to the general protocol B. $^1$H NMR (400 MHz, DMSO-d$_6$) δ ppm 8.69 (t, J=5.6 Hz, 1 H), 7.92 (d, J=1.6 Hz, 1 H), 7.85 (dd, J=8.2, 1.4 Hz, 1 H), 7.59-7.75 (m, 4 H), 7.49-7.58 (m, 1 H), 7.12 (s, 1 H), 4.55 (dq, J=13.9, 7.0 Hz, 1 H), 3.73 (dq, J=13.8, 6.9 Hz, 1 H), 3.40-3.58 (m, 2 H), 2.85 (t, J=7.3 Hz, 2 H), 2.58 (s, 3 H), 1.17 (t, J=7.0 Hz, 3 H); LCMS RT=4.15 min, m/z 440.1 [M+H$^+$]; HRMS (ESI) m/z calcd for C$_{22}$H$_{22}$N$_3$O$_3$S$_2$ [M+H$^+$] 440.1097, found 440.1105.

Example 91

10-Ethyl-N-(3-methoxyphenethyl)-11-oxo-10,11-dihydrodibenzo[b,f][1,4]thiazepine-8-carboxamide 5-oxide

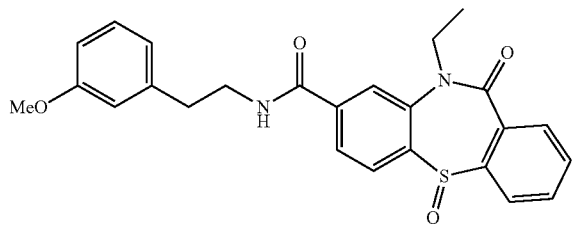 [SMILES: CCN1C(=O)c2ccccc2S(=O)c2ccc(C(=O)NCCc3cccc(OC)c3)cc21]

The title compound was prepared according to the general protocol A. $^1$H NMR (400 MHz, DMSO-d$_6$) δ ppm 8.67 (t, J=5.6 Hz, 1 H), 7.90 (d, J=1.4 Hz, 1 H), 7.84 (dd, J=8.3, 1.3 Hz, 1 H), 7.59-7.74 (m, 4 H), 7.50-7.58 (m, 1 H), 7.16 (t, J=7.9 Hz, 1 H), 6.65-6.82 (m, 3 H), 4.46-4.62 (m, 1 H), 3.69-3.78 (m, 1 H), 3.66 (s, 3 H), 3.37-3.49 (m, 2 H), 2.76 (t, J=7.2 Hz, 2 H), 1.17 (t, J=7.0 Hz, 3 H); LCMS RT=5.36 min, m/z 449.1 [M+H$^+$]; HRMS (ESI) m/z calcd for C$_{25}$H$_{25}$N$_2$O$_4$S [M+H$^+$] 449.1530, found 449.1528.

Example 92

N-(1-Adamantyl)-10-ethyl-11-oxo-10,11-dihydrodibenzo[b,f][1,4]thiazepine-8-carboxamide 5-oxide

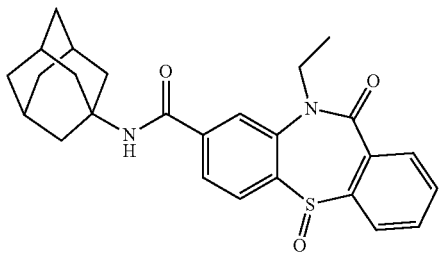 [SMILES: CCN1C(=O)c2ccccc2S(=O)c2ccc(C(=O)NC34CC5CC(CC(C5)C3)C4)cc21]

The title compound was prepared according to the general protocol A. $^1$H NMR (400 MHz, DMSO-d$_6$) δ ppm 8.07 (d, J=6.8 Hz, 1 H), 7.92 (d, J=1.4 Hz, 1 H), 7.83 (dd, J=8.1, 1.1 Hz, 1 H), 7.58-7.73 (m, 4 H), 7.48-7.57 (m, 1 H), 4.57 (dq, J=13.9, 7.0 Hz, 1 H), 3.91-4.02 (m, 1 H), 3.75 (dq, J=14.0, 7.0 Hz, 1 H), 2.04 (t, J=14.2 Hz, 2 H), 1.92 (br. s., 2 H), 1.70-1.85 (m, 6 H), 1.67 (br. s., 2 H), 1.40-1.53 (m, 2 H), 1.17 (t, J=7.1 Hz, 3 H); LCMS RT=6.23 min, m/z 449.2 [M+H$^+$]; HRMS (ESI) m/z calcd for C$_{26}$H$_{29}$N$_2$O$_3$S [M+H$^+$] 449.1893, found 449.1892.

Example 93

10-Ethyl-N-((1-methyl-1H-imidazol-5-yl)methyl)-11-oxo-10,11-dihydrodibenzo[b,f][1,4]thiazepine-8-carboxamide 5-oxide

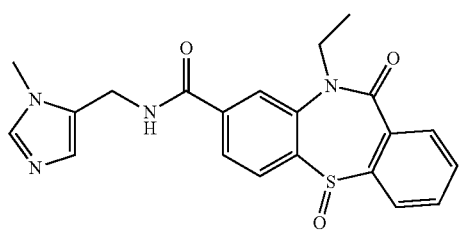 [SMILES: CCN1C(=O)c2ccccc2S(=O)c2ccc(C(=O)NCc3cncn3C)cc21]

The title compound was prepared according to the general protocol B. $^1$H NMR (400 MHz, DMSO-d$_6$) δ ppm 9.12 (t, J=5.7 Hz, 1 H), 8.89 (s, 1 H), 7.98 (d, J=1.4 Hz, 1 H), 7.89 (dd, J=8.2, 1.0 Hz, 1 H), 7.65-7.75 (m, 3 H), 7.59-7.65 (m, 1 H), 7.48-7.58 (m, 2 H), 4.40-4.66 (m, 3 H), 3.79 (s, 3 H), 3.65-3.77 (m, 1 H), 1.17 (t, J=7.1 Hz, 3 H); LCMS RT=3.49 min, m/z 409.1 [M+H$^+$]; HRMS (ESI) m/z calcd for C$_{21}$H$_{21}$N$_4$O$_3$S [M+H$^+$] 409.1329, found 409.1331.

Example 94

10-Ethyl-N-((2-methylthiazol-4-yl)methyl)-11-oxo-10,11-dihydrodibenzo[b,f][1,4]thiazepine-8-carboxamide 5-oxide

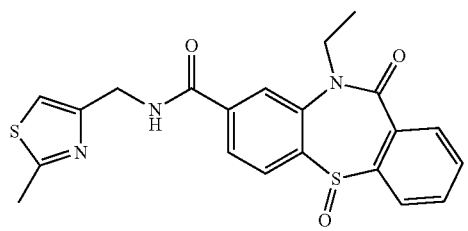 [SMILES: CCN1C(=O)c2ccccc2S(=O)c2ccc(C(=O)NCc3csc(C)n3)cc21]

The title compound was prepared according to the general protocol B. $^1$H NMR (400 MHz, DMSO-d$_6$) δ ppm 9.15 (t, J=5.8 Hz, 1 H), 8.02 (d, J=1.6 Hz, 1 H), 7.86-7.96 (m, 1 H), 7.60-7.73 (m, 4 H), 7.51-7.57 (m, 1 H), 7.21 (s, 1 H), 4.52-4.62 (m, 1 H), 4.38-4.52 (m, 2 H), 3.68-3.83 (m, 1 H), 2.58 (s, 3 H), 1.18 (t, J=7.0 Hz, 3 H); LCMS RT=4.42 min, m/z 426.1 [M+H$^+$]; HRMS (ESI) m/z calcd for C$_{21}$H$_{20}$N$_3$O$_3$S$_2$ [M+H$^+$] 426.0941, found 426.0945.

Example 95

10-Ethyl-N-((1-methyl-1H-imidazol-4-yl)methyl)-11-oxo-10,11-dihydrodibenzo[b,f][1,4]thiazepine-8-carboxamide 5-oxide

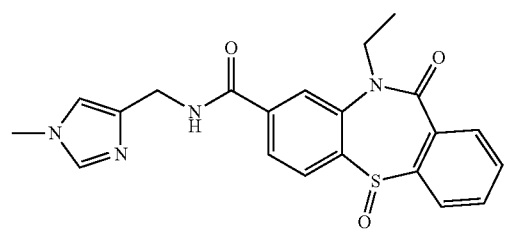 [SMILES: CCN1C(=O)c2ccccc2S(=O)c2ccc(C(=O)NCc3cn(C)cn3)cc21]

The title compound was prepared according to the general protocol B. $^1$H NMR (400 MHz, DMSO-d$_6$) δ ppm 9.18 (t, J=5.6 Hz, 1 H), 8.72 (br. s., 1 H), 7.99 (d, J=1.6 Hz, 1 H), 7.90 (dd, J=8.2, 1.2 Hz, 1 H), 7.66-7.77 (m, 3 H), 7.59-7.65 (m, 1 H), 7.50-7.59 (m, 1 H), 7.45 (s, 1 H), 4.51-4.64 (m, 1 H), 4.33-4.50 (m, 2 H), 3.74 (s, 3 H), 3.61-3.82 (m, 1 H), 1.18 (t, J=7.1 Hz, 3 H); LCMS RT=3.48 min, m/z 409.1 [M+H$^+$]; HRMS (ESI) m/z calcd for C$_{21}$H$_{21}$N$_4$O$_3$S [M+H$^+$] 409.1329, found 409.1339.

Example 96

10-Ethyl-N-(5-methylthiazol-2-yl)-11-oxo-10,11-dihydrodibenzo[b,f][1,4]thiazepine-8-carboxamide 5-oxide

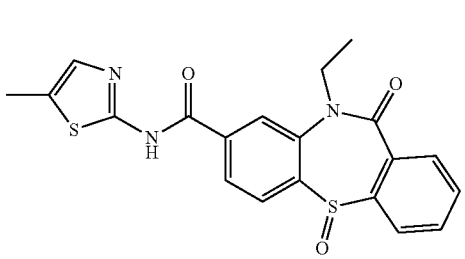 [SMILES: CCN1C(=O)c2ccccc2S(=O)c2ccc(C(=O)Nc3ncc(C)s3)cc21]

The title compound was prepared according to the general protocol B. LCMS RT=5.17 min, m/z 412.1 [M+H$^+$]; HRMS (ESI) m/z calcd for C$_{20}$H$_{18}$N$_3$O$_3$S$_2$ [M+H$^+$] 412.0784, found 412.0793.

Example 97

(E)-2-(8-Chlorodibenzo[b,f]thiepin-10-yloxy)-N,N-dimethylethanamine 5-oxide

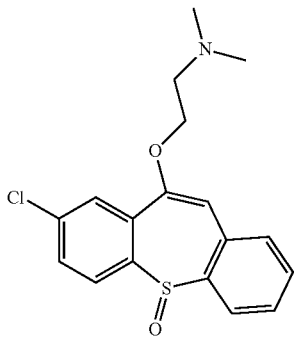 [SMILES: CN(C)CCOC1=Cc2ccccc2S(=O)c2ccc(Cl)cc21]

A suspension of 2-(8-chlorodibenzo[b,f]thiepin-10-yloxy)-N,N-dimethylethanamine (5.00 mg, 0.015 mmol) in acetic acid (1.00 mL) was treated at room temperature with H$_2$O$_2$ (69.0 µL, 0.68 mmol). The reaction mixture was stirred at room temperature for overnight. The crude mixture was concentrated and purified by preparative HPLC to give 1.7 mg (32%) of the title compound and 1.7 mg (31%) of (E)-2-(8-chlorodibenzo[b,f]thiepin-10-yloxy)-N,N-dimethylethanamine 5,5-dioxide (XJB08-083_pk2, NCGC00241701-01). LCMS RT=4.04 min, m/z 348.1 [M+H$^+$]; HRMS (ESI) m/z calcd for C$_{18}$H$_{19}$ClNO$_2$S [M+H$^+$] 348.0820, found 348.0820.

Example 98

(E)-2-(8-chlorodibenzo[b,f]thiepin-10-yloxy)-N,N-dimethylethanamine 5,5-dioxide

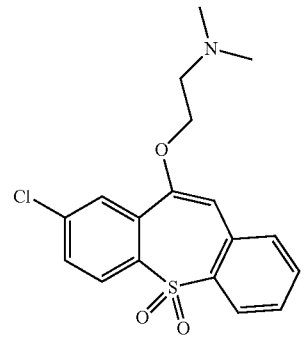 [SMILES: CN(C)CCOC1=Cc2ccccc2S(=O)(=O)c2ccc(Cl)cc21]

LCMS RT=4.23 min, m/z 364.1 [M+H$^+$]; HRMS (ESI) m/z calcd for C$_{18}$H$_{19}$ClNO$_3$S [M+H$^+$] 364.0769, found 364.0770.

Example 99

10-Ethyl-N-(3-fluorobenzyl)-11-oxo-10,11-dihydrodibenzo[b,f][1,4]thiazepine-8-carboxamide 5-oxide

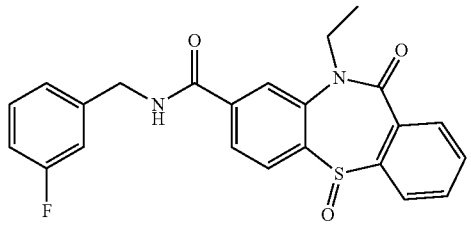 [SMILES: CCN1C(=O)c2ccccc2S(=O)c2ccc(C(=O)NCc3cccc(F)c3)cc21]

The title compound was prepared according to the general protocol A. $^1$H NMR (400 MHz, DMSO-d$_6$) δ ppm 9.18 (t, J=6.3 Hz, 1 H), 8.02 (d, J=1.6 Hz, 1 H), 7.93 (dd, J=8.2, 1.6 Hz, 1 H), 7.66-7.75 (m, 3 H), 7.61-7.67 (m, 1 H), 7.55 (ddd, J=7.9, 7.0, 1.4 Hz, 1 H), 7.27-7.38 (m, 1 H), 6.98-7.16 (m, 3 H), 4.51-4.65 (m, 1 H), 4.36-4.51 (m, 2 H), 3.66-3.83 (m, 1 H), 1.18 (t, J=7.1 Hz, 3 H); LCMS RT=5.33 min, m/z 423.1 [M+H$^+$]; HRMS (ESI) m/z calcd for C$_{23}$H$_{20}$FN$_2$O$_3$S [M+H$^+$] 423.1173, found 423.1177.

Example 100

N-(3-(Dimethylamino)propyl)-10-ethyl-11-oxo-10,11-dihydrodibenzo[b,f][1,4]thiazepine-8-carboxamide 5-oxide

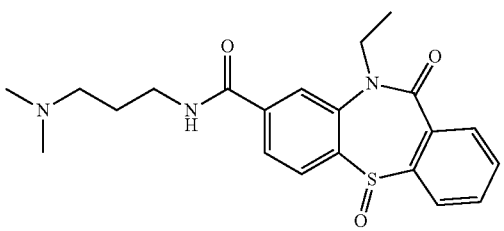 [SMILES: CCN1C(=O)c2ccccc2S(=O)c2ccc(C(=O)NCCCN(C)C)cc21]

The title compound was prepared according to the general protocol B. LCMS RT=3.48 min, m/z 400.2 [M+H$^+$]; HRMS (ESI) m/z calcd for $C_{21}H_{26}N_3O_3S$ [M+H$^+$] 400.1689, found 400.1692.

Example 101

N-(4-Aminophenethyl)-10-ethyl-11-oxo-10,11-dihydrodibenzo[b,f][1,4]thiazepine-8-carboxamide 5-oxide

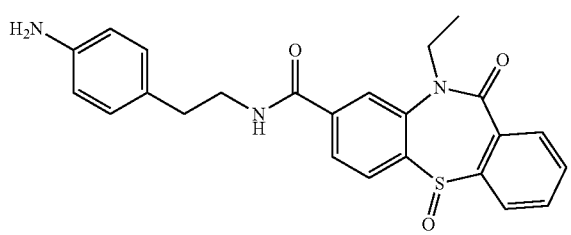 [SMILES: CCN1C(=O)c2ccccc2S(=O)c2ccc(C(=O)NCCc3ccc(N)cc3)cc21]

The title compound was prepared according to the general protocol B. LCMS RT=3.69 min, m/z 434.1 [M+H$^+$]; HRMS (ESI) m/z calcd for $C_{24}H_{24}N_3O_3S$ [M+H$^+$] 434.1533, found 434.1533.

Example 102

N-(4-Methoxybenzyl)-11-oxo-10,11-dihydrodibenzo[b,f][1,4]thiazepine-8-carboxamide 5,5-dioxide

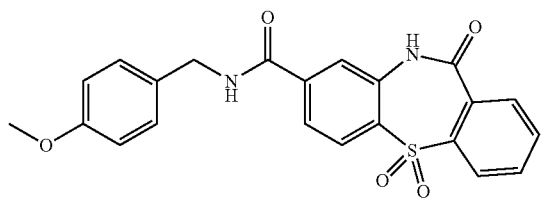 [SMILES: COc1ccc(CNC(=O)c2ccc3c(c2)NC(=O)c2ccccc2S3(=O)=O)cc1]

A suspension of N-(4-methoxybenzyl)-11-oxo-10,11-dihydrodibenzo[b,f][1,4]thiazepine-8-carboxamide (25.0 mg, 0.064 mmol) in acetic acid (2.00 mL) was treated at room temperature with $H_2O_2$ (0.60 mL, 5.87 mmol). The reaction mixture was stirred at room temperature for 5 days. $Na_2S_2O_3$ was added to the solution to quench the excess $H_2O_2$. Acetic acid was removed and the crude mixture was purified by preparative HPLC to give 6.7 mg (24%) the title compound. $^1$H NMR (400 MHz, DMSO-d$_6$) δ ppm 11.48 (s, 1 H), 9.17 (t, J=6.0 Hz, 1 H), 8.02 (d, J=8.2 Hz, 1 H), 7.91-7.99 (m, 2 H), 7.75-7.92 (m, 4 H), 7.15-7.26 (m, 2 H), 6.79-6.92 (m, 2 H), 4.36 (d, J=5.9 Hz, 2 H), 3.69 (s, 3 H); LCMS RT=4.98 min, m/z 423.1 [M+H$^+$]; HRMS (ESI) m/z calcd for $C_{22}H_{19}N_2O_5S$ [M+H$^+$] 423.1009, found 423.1005.

Example 103

N-(4-Chlorobenzyl)-10-methyl-11-oxo-10,11-dihydrodibenzo[b,f][1,4]thiazepine-8-carboxamide 5-(R)-oxide

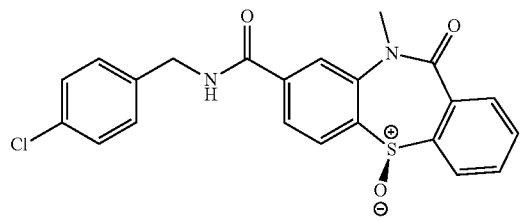 [SMILES: CN1C(=O)c2ccccc2[S@@+]([O-])c2ccc(C(=O)NCc3ccc(Cl)cc3)cc21]

Separation of enantiomers via chiral HPLC: Analytical analysis was performed on a CHIRALPAK®IA® column (4.6×150 mm, 5 micron). The mobile phase was 60% of isopropanol in hexanes at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=5.96 minutes; positive optical rotation. The second eluting peak: RT=6.72 minutes; negative optical rotation. Preparative separation was performed on a CHIRALPAK®IA® column (5×50 cm, 20 micron). The mobile phase was 60% of isopropanol in hexanes at a flow rate of 30 mL/min. Fraction collection was triggered by UV absorbance (254 nm). LCMS RT=5.47 min, m/z 425.1 [M+H$^+$]; HRMS (ESI) m/z calcd for $C_{22}H_{18}ClN_2O_3S$ [M+H$^+$] 425.0721, found 425.0714.

Example 104

N-(4-Bromobenzyl)-10-methyl-11-oxo-10,11-dihydrodibenzo[b,f][1,4]thiazepine-8-carboxamide 5-(R)-oxide

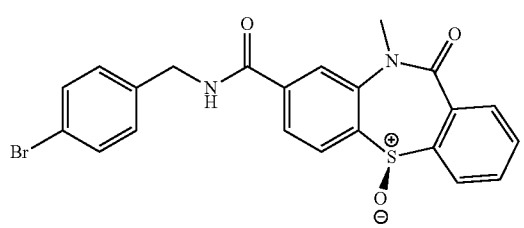

Separation of enantiomers via chiral HPLC: Analytical analysis was performed on a CHIRALPAK®IA® column (4.6×250 mm, 5 micron). The mobile phase was 60% of ethanol in hexanes at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=7.49 minutes; positive optical rotation. The second eluting peak: RT=8.68 minutes; negative optical rotation. Preparative separation was performed on a CHIRALPAK®IA® column (5×50 cm, 20 micron). The mobile phase was 60% of ethanol in hexanes at a flow rate of 35 mL/min. Fraction collection was triggered by UV absorbance (254 nm). LCMS RT=5.57 min, m/z 469.0 [M+H⁺]; HRMS (ESI) m/z calcd for $C_{22}H_{18}BrN_2O_3S$ [M+H⁺] 469.0216, found 469.0220.

Example 105

N-(4-Iodobenzyl)-10-methyl-11-oxo-10,11-dihydrodibenzo[b,f][1,4]thiazepine-8-carboxamide 5-oxide

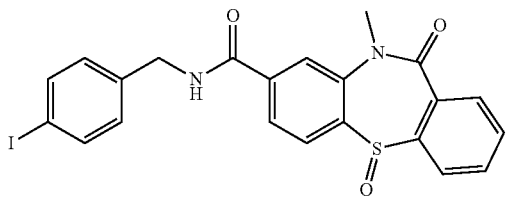 [SMILES: CN1C(=O)c2ccccc2S(=O)c2ccc(C(=O)NCc3ccc(I)cc3)cc21]

The title compound was prepared according to the general protocol A. ¹H NMR (400 MHz, DMSO-d₆) δ ppm 9.16 (t, J=6.1 Hz, 1 H), 8.00 (d, J=1.6 Hz, 1 H), 7.86-7.95 (m, 1 H), 7.70-7.77 (m, 2 H), 7.61-7.69 (m, 4 H), 7.57 (ddd, J=7.9, 7.0, 1.4 Hz, 1 H), 7.05-7.14 (m, 2 H), 4.29-4.50 (m, 2 H), 3.55 (s, 3 H); LCMS RT=5.71 min, m/z 517.0 [M+H⁺]; HRMS (ESI) m/z calcd for $C_{22}H_{18}IN_2O_3S$ [M+H⁺] 517.0077, found 517.0078.

Example 106

N-(3-Fluorobenzyl)-10-methyl-11-oxo-10,11-dihydrodibenzo[b,f][1,4]thiazepine-8-carboxamide 5-oxide

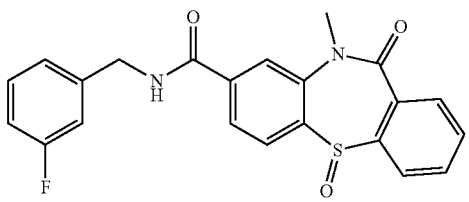 [SMILES: CN1C(=O)c2ccccc2S(=O)c2ccc(C(=O)NCc3cccc(F)c3)cc21]

The title compound was prepared according to the general protocol A. LCMS RT=5.18 min, m/z 431.0 [M+Na⁺]; HRMS (ESI) m/z calcd for $C_{22}H_{18}FN_2O_3S$ [M+H⁺] 409.1017, found 409.1019.

Example 107

10-Methyl-11-oxo-N-(2-(thiophen-2-yl)ethyl)-10,11-dihydrodibenzo[b,f][1,4]thiazepine-8-carboxamide 5-(R)-oxide

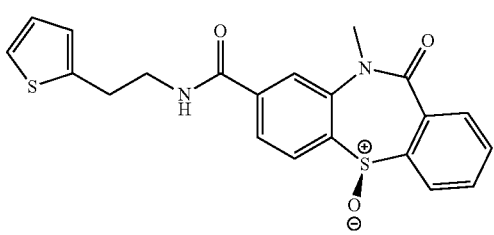

Separation of enantiomers via chiral HPLC: Analytical analysis was performed on a CHIRALPAK®IA® column (4.6×250 mm, 5 micron). The mobile phase was 60% of ethanol in hexanes at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=6.51 minutes; negative optical rotation. The second eluting peak: RT=6.76 minutes; positive optical rotation. Preparative separation was performed on a CHIRALPAK®IA® column (5×50 cm, 20 micron). The mobile phase was 60% of ethanol in hexanes at a flow rate of 35 mL/min. Fraction collection was triggered by UV absorbance (254 nm). LCMS RT=5.10 min, m/z 411.0 [M+H⁺]; HRMS (ESI) m/z calcd for $C_{21}H_{19}N_2O_3S_2$ [M+H⁺] 411.0832, found 411.0833.

Example 108

(S)-10-Methyl-11-oxo-N-(1-phenylethyl)-10,11-dihydrodibenzo[b,f][1,4]thiazepine-8-carboxamide 5-oxide

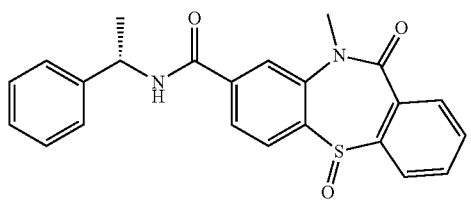 [SMILES: C[C@H](NC(=O)c1ccc2c(c1)N(C)C(=O)c1ccccc1S2=O)c1ccccc1]

The title compound was prepared according to the general protocol A. ¹H NMR (400 MHz, DMSO-d₆) δ ppm 8.90 (d, J=8.0 Hz, 0.5 H), 8.89 (d, J=8.0 Hz, 0.5 H), 7.99 (dd, J=6.8, 1.6 Hz, 1 H), 7.91 (td, J=8.1, 1.6 Hz, 1 H), 7.70-7.77 (m, 2 H), 7.63-7.68 (m, 2 H), 7.56 (tt, J=7.4, 1.3 Hz, 1 H), 7.31-7.37 (m, 2 H), 7.25-7.31 (m, 2 H), 7.16-7.22 (m, 1 H), 5.11 (quin, J=7.1 Hz, 1 H), 3.56 (s, 1.5 H), 3.55 (s, 1.5 H), 1.44 (d, J=7.0 Hz, 1.5 H), 1.43 (d, J=7.0 Hz, 1.5 H); LCMS RT=5.29 min, m/z 405.1 [M+H⁺]; HRMS (ESI) m/z calcd for $C_{23}H_{21}N_2O_3S$ [M+H⁺] 405.1267, found 405.1265.

Example 109

N-(3,5-Difluorobenzyl)-10-methyl-11-oxo-10,11-dihydrodibenzo[b,f][1,4]thiazepine-8-carboxamide 5-oxide

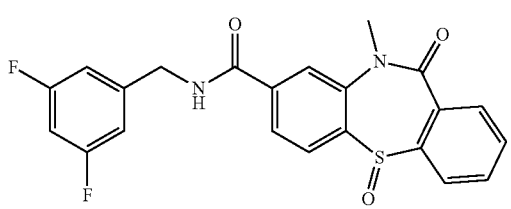 [SMILES: CN1C(=O)c2ccccc2S(=O)c2ccc(C(=O)NCc3cc(F)cc(F)c3)cc21]

The title compound was prepared according to the general protocol A. LCMS RT=5.34 min, m/z 449.0 [M+Na⁺]; HRMS (ESI) m/z calcd for $C_{22}H_{17}F_2N_2O_3S$ [M+H⁺] 427.0922, found 427.0919.

Example 110

N-(2-(Dimethylamino)ethyl)-10-methyl-11-oxo-10,11-dihydrodibenzo[b,f][1,4]thiazepine-8-carboxamide 5-oxide

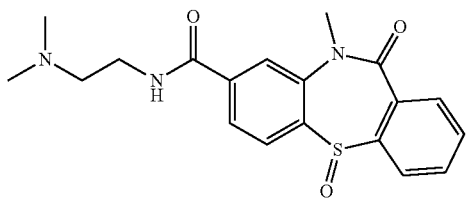 [SMILES: CN(C)CCNC(=O)c1ccc2c(c1)N(C)C(=O)c1ccccc1S2=O]

The title compound was prepared according to the general protocol B. $^1$H NMR (400 MHz, DMSO-d$_6$) δ ppm 8.78 (t, J=5.7 Hz, 1 H), 7.96 (d, J=1.6 Hz, 1 H), 7.89 (dd, J=8.1, 1.5 Hz, 1 H), 7.69-7.79 (m, 3 H), 7.62-7.69 (m, 1 H), 7.51-7.61 (m, 1 H), 3.56 (s, 3 H), 3.44-3.69 (m, 2 H), 3.20 (br. s., 2 H), 2.79 (s, 6 H); LCMS RT=3.18 min, m/z 372.1 [M+H$^+$]; HRMS (ESI) m/z calcd for C$_{19}$H$_{22}$N$_3$O$_3$S [M+H$^+$] 372.1376, found 372.1382.

Example 111

10-Methyl-11-oxo-N-(pyridin-3-ylmethyl)-10,11-dihydrodibenzo[b,f][1,4]thiazepine-8-carboxamide 5-(R)-oxide

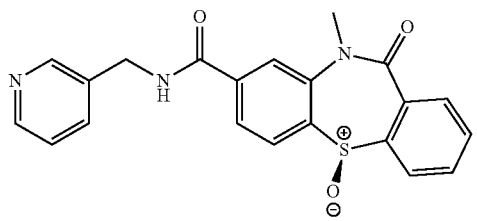 [SMILES: CN1C(=O)c2ccccc2[S@@+]([O-])c2ccc(C(=O)NCc3cccnc3)cc21]

Separation of enantiomers via chiral HPLC: Analytical analysis was performed on a CHIRALPAK®IA® column (4.6×250 mm, 5 micron). The mobile phase was 60% of ethanol in hexanes at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=9.00 minutes; positive optical rotation. The second eluting peak: RT=13.28 minutes; negative optical rotation. Preparative separation was performed on a CHIRALPAK®IA® IA column (5×50 cm, 20 micron). The mobile phase was 60% of ethanol in hexanes at a flow rate of 35 mL/min. Fraction collection was triggered by UV absorbance (254 nm). LCMS RT=3.37 min, m/z 392.1 [M+H$^+$]; HRMS (ESI) m/z calcd for C$_{21}$H$_{18}$N$_3$O$_3$S [M+H$^+$] 392.1063, found 392.1068.

Example 112

N-(4-(Dimethylamino)butyl)-10-methyl-11-oxo-10,11-dihydrodibenzo[b,f][1,4]thiazepine-8-carboxamide 5-oxide

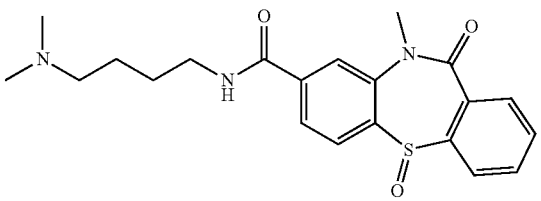 [SMILES: CN(C)CCCCNC(=O)c1ccc2c(c1)N(C)C(=O)c1ccccc1S2=O]

The title compound was prepared according to the general protocol B. $^1$H NMR (400 MHz, DMSO-d$_6$) δ ppm 8.63 (t, J=5.8 Hz, 1 H), 7.94 (d, J=1.6 Hz, 1 H), 7.86 (dd, J=8.2, 1.6 Hz, 1 H), 7.70-7.78 (m, 2 H), 7.63-7.70 (m, 2 H), 7.57 (ddd, J=7.9, 7.0, 1.4 Hz, 1 H), 3.56 (s, 3 H), 3.18-3.36 (m, 2 H), 2.93-3.10 (m, 2 H), 2.72 (s, 6 H), 1.55-1.68 (m, 2 H), 1.41-1.54 (m, 2 H); LCMS RT=3.27 min, m/z 400.1 [M+H$^+$]; HRMS (ESI) m/z calcd for C$_{21}$H$_{26}$N$_3$O$_3$S [M+H$^+$] 400.1689, found 400.1694.

Example 113

(R)-10-Methyl-11-oxo-N-(1-phenylethyl)-10,11-dihydrodibenzo[b,f][1,4]thiazepine-8-carboxamide 5-oxide

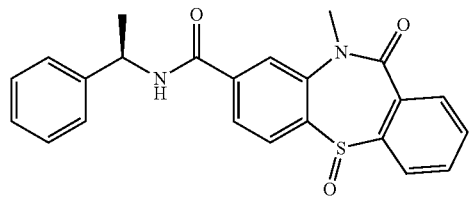 [SMILES: C[C@@H](NC(=O)c1ccc2c(c1)N(C)C(=O)c1ccccc1S2=O)c1ccccc1]

The title compound was prepared according to the general protocol A. $^1$H NMR (400 MHz, DMSO-d$_6$) δ ppm 8.90 (d, J=8.1 Hz, 0.5 H), 8.89 (d, J=8.1 Hz, 0.5 H), 7.99 (dd, J=6.9, 1.3 Hz, 1 H), 7.91 (td, J=8.1, 1.6 Hz, 1 H), 7.69-7.77 (m, 2 H), 7.63-7.69 (m, 2 H), 7.56 (tt, J=7.5, 1.3 Hz, 1 H), 7.24-7.38 (m, 4 H), 7.16-7.23 (m, 1 H), 5.11 (qd, J=7.4, 7.1 Hz, 1 H), 3.56 (s, 1.5 H), 3.55 (s, 1.5 H), 1.45 (d, J=7.0 Hz, 1.5 H), 1.44 (d, J=7.0 Hz, 1.5 H); LCMS RT=5.28 min, m/z 405.1 [M+H$^+$]; HRMS (ESI) m/z calcd for C$_{23}$H$_{21}$N$_2$O$_3$S [M+H$^+$] 405.1267, found 405.1270.

Example 114

(S)-N-(1-(4-Chlorophenyl)ethyl)-10-methyl-11-oxo-10,11-dihydrodibenzo[b,f][1,4]thiazepine-8-carboxamide 5-oxide

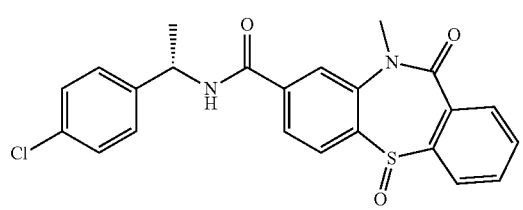 [SMILES: C[C@H](NC(=O)c1ccc2c(c1)N(C)C(=O)c1ccccc1S2=O)c1ccc(Cl)cc1]

The title compound was prepared according to the general protocol A. $^1$H NMR (400 MHz, DMSO-d$_6$) δ ppm 8.92 (d, J=7.7 Hz, 0.5 H), 8.91 (d, J=7.7 Hz, 0.5 H), 7.98 (dd, J=7.8, 1.4 Hz, 1 H), 7.90 (td, J=8.1, 1.6 Hz, 1 H), 7.70-7.77 (m, 2 H), 7.62-7.69 (m, 2 H), 7.53-7.61 (m, 1 H), 7.30-7.41 (m, 4 H), 5.09 (quin, J=7.1 Hz, 1 H), 3.56 (s, 1.5 H), 3.55 (s, 1.5 H), 1.43 (d, J=7.1 Hz, 1.5 H), 1.42 (d, J=7.1 Hz, 1.5 H); LCMS RT=5.69 min, m/z 439.0 [M+H$^+$]; HRMS (ESI) m/z calcd for C$_{23}$H$_{20}$ClN$_2$O$_3$S [M+H$^+$] 439.0878, found 439.0885.

Example 115

(R)-N-(1-(4-Chlorophenyl)ethyl)-10-methyl-11-oxo-10,11-dihydrodibenzo[b,f][1,4]thiazepine-8-carboxamide 5-oxide

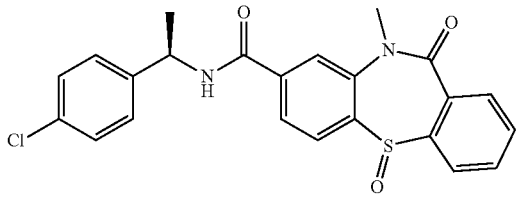 [SMILES: C[C@@H](NC(=O)c1ccc2c(c1)N(C)C(=O)c1ccccc1S2=O)c1ccc(Cl)cc1]

The title compound was prepared according to the general protocol A. $^1$H NMR (400 MHz, DMSO-d$_6$) δ ppm 8.92 (d, J=7.7 Hz, 0.5 H), 8.91 (d, J=7.7 Hz, 0.5 H), 7.98 (dd, J=7.9, 1.5 Hz, 1 H), 7.90 (td, J=8.1, 1.6 Hz, 1 H), 7.70-7.77 (m, 2 H), 7.63-7.69 (m, 2 H), 7.53-7.61 (m, 1 H), 7.29-7.39 (m, 4 H), 5.09 (quin, J=7.3 Hz, 1 H), 3.56 (s, 1.5 H), 3.55 (s, 1.5 H), 1.43 (d, J=7.0 Hz, 1.5 H), 1.42 (d, J=7.0 Hz, 1.5 H); LCMS RT=5.69 min, m/z 439.0 [M+H$^+$]; HRMS (ESI) m/z calcd for C$_{23}$H$_{20}$ClN$_2$O$_3$S [M+H$^+$] 439.0878, found 439.0878.

Example 116

10-Methyl-11-oxo-N-(pyridin-2-yl)-10,11-dihydrodibenzo[b,f][1,4]thiazepine-8-carboxamide 5-oxide

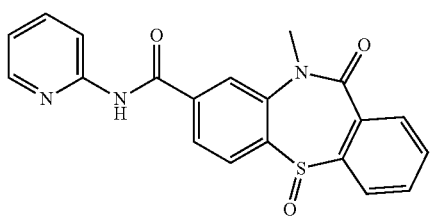 [SMILES: CN1C(=O)c2ccccc2S(=O)c2ccc(C(=O)Nc3ccccn3)cc21]

The title compound was prepared according to the general protocol B. $^1$H NMR (400 MHz, DMSO-d$_6$) δ ppm 11.01 (s, 1 H), 8.37 (ddd, J=4.9, 2.0, 1.0 Hz, 1 H), 8.17 (d, J=1.6 Hz, 1 H), 8.14 (d, J=8.4 Hz, 1 H), 8.01 (dd, J=8.1, 1.7 Hz, 1 H), 7.83 (ddd, J=8.3, 7.3, 2.0 Hz, 1 H), 7.66-7.78 (m, 4 H), 7.58 (td, J=7.4, 1.4 Hz, 1 H), 7.16 (ddd, J=7.4, 4.8, 1.1 Hz, 1 H), 3.60 (s, 3 H); LCMS RT=3.99 min, m/z 378.0 [M+H$^+$]; HRMS (ESI) m/z calcd for C$_{20}$H$_{16}$N$_3$O$_3$S [M+H$^+$] 378.0907, found 378.0908.

Example 117

10-Methyl-11-oxo-N-(pyridin-3-yl)-10,11-dihydrodibenzo[b,f][1,4]thiazepine-8-carboxamide 5-oxide

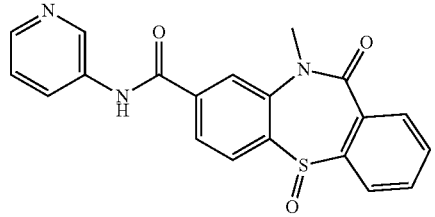 [SMILES: CN1C(=O)c2ccccc2S(=O)c2ccc(C(=O)Nc3cccnc3)cc21]

The title compound was prepared according to the general protocol B. LCMS RT=3.43 min, m/z 378.0 [M+H$^+$]; HRMS (ESI) m/z calcd for C$_{20}$H$_{16}$N$_3$O$_3$S [M+H$^+$] 378.0907, found 378.0909.

Example 118

10-Methyl-11-oxo-N-(pyridin-4-yl)-10,11-dihydrodibenzo[b,f][1,4]thiazepine-8-carboxamide 5-oxide

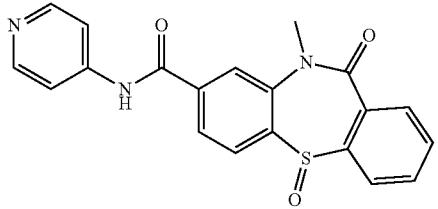 [SMILES: CN1C(=O)c2ccccc2S(=O)c2ccc(C(=O)Nc3ccncc3)cc21]

The title compound was prepared according to the general protocol B. $^1$H NMR (400 MHz, DMSO-d$_6$) δ ppm 11.21 (br. s., 1 H), 8.65 (d, J=6.7 Hz, 2 H), 8.11 (d, J=1.4 Hz, 1 H), 7.94-8.06 (m, 3 H), 7.65-7.82 (m, 4 H), 7.58 (td, J=7.5, 1.5 Hz, 1 H), 3.59 (s, 3 H); LCMS RT=3.44 min, m/z 378.0 [M+H$^+$]; HRMS (ESI) m/z calcd for C$_{20}$H$_{16}$N$_3$O$_3$S [M+H$^+$] 378.0907, found 378.0906.

Example 119

10-Methyl-11-oxo-N-(3-(piperidin-1-yl)propyl)-10,11-dihydrodibenzo[b,f][1,4]thiazepine-8-carboxamide 5-oxide

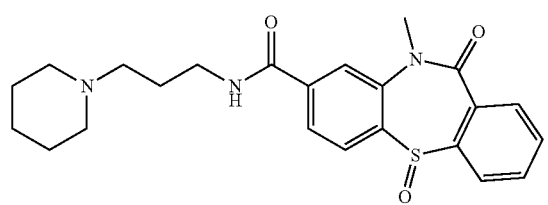 [SMILES: CN1C(=O)c2ccccc2S(=O)c2ccc(C(=O)NCCCN3CCCCC3)cc21]

The title compound was prepared according to the general protocol B. $^1$H NMR (400 MHz, DMSO-d$_6$) δ ppm 8.72 (t, J=5.6 Hz, 1 H), 7.95 (d, J=1.4 Hz, 1 H), 7.87 (dd, J=8.2, 1.6 Hz, 1 H), 7.63-7.79 (m, 4 H), 7.57 (td, J=7.4, 1.3 Hz, 1 H), 3.55 (s, 3 H), 3.21-3.45 (m, 4 H), 2.97-3.10 (m, 2 H), 2.71-2.91 (m, 2 H), 1.72-1.92 (m, 4 H), 1.45-1.72 (m, 3 H), 1.25-1.43 (m, 1 H); LCMS RT=3.41 min, m/z 426.1 [M+H$^+$]; HRMS (ESI) m/z calcd for $C_{23}H_{28}N_3O_3S$ [M+H$^+$] 426.1846, found 426.1854.

Example 120

10-Methyl-11-oxo-N-(2,2,2-trifluoro-1-phenylethyl)-10,11-dihydrodibenzo[b,f][1,4]thiazepine-8-carboxamide 5-oxide

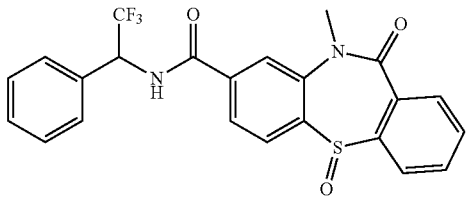 [SMILES: CN1C(=O)c2ccccc2S(=O)c2ccc(C(=O)NC(c3ccccc3)C(F)(F)F)cc21]

The title compound was prepared according to the general protocol A. $^1$H NMR (400 MHz, DMSO-d$_6$) δ ppm 9.61 (d, J=9.2 Hz, 0.5 H), 9.59 (d, J=9.2 Hz, 0.5 H), 7.99 (t, J=1.9 Hz, 1 H), 7.91 (ddd, J=8.1, 5.1, 1.7 Hz, 1 H), 7.65-7.78 (m, 4 H), 7.60-7.65 (m, 2 H), 7.53-7.60 (m, 1 H), 7.37-7.46 (m, 3 H), 5.94-6.08 (m, 1 H), 3.57 (s, 1.5 H), 3.56 (s, 1.5 H); $^{19}$F NMR (376 MHz, DMSO-d$_6$) δ ppm −71.85 (d, J=8.9 Hz, 1.5F), −71.91 (d, J=8.9 Hz, 1.5 F); LCMS RT=5.76 min, m/z 459.0 [M+H$^+$]; HRMS (ESI) m/z calcd for $C_{23}H_{18}F_3N_2O_3S$ [M+H$^+$] 459.0985, found 459.0991.

Example 121

10-Ethyl-11-oxo-N-(2,2,2-trifluoro-1-phenylethyl)-10,11-dihydrodibenzo[b,f][1,4]thiazepine-8-carboxamide 5-oxide

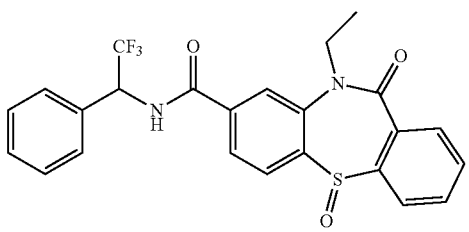 [SMILES: CCN1C(=O)c2ccccc2S(=O)c2ccc(C(=O)NC(c3ccccc3)C(F)(F)F)cc21]

The title compound was prepared according to the general protocol A. $^1$H NMR (400 MHz, DMSO-d$_6$) δ ppm 9.61 (d, J=6.9 Hz, 0.5 H), 9.59 (d, J=6.9 Hz, 0.5 H), 8.01 (dd, J=4.4, 1.5 Hz, 1 H), 7.92 (ddd, J=8.1, 4.1, 1.6 Hz, 1 H), 7.67-7.75 (m, 3 H), 7.59-7.67 (m, 3 H), 7.52-7.59 (m, 1 H), 7.37-7.46 (m, 3 H), 6.01 (quin, J=9.0 Hz, 1 H), 4.49-4.64 (m, J=13.9, 7.2, 7.2, 7.0, 3.4 Hz, 1 H), 3.57-3.99 (m, 1 H), 1.19 (t, J=7.1 Hz, 1.5 H), 1.18 (t, J=7.1 Hz, 1.5 H); $^{19}$F NMR (376 MHz, DMSO-d$_6$) δ ppm −71.85 (d, J=8.9 Hz, 1.5 F), −71.90 (d, J=8.3 Hz, 1.5F); LCMS RT=6.00 min, m/z 473 [M+H$^+$]; HRMS (ESI) m/z calcd for $C_{24}H_{20}F_3N_2O_3S$ [M+H$^+$] 473.1141, found 473.1147.

Example 122

10-Methyl-11-oxo-N-(2-(pyrrolidin-1-yl)ethyl)-10,11-dihydrodibenzo[b,f][1,4]thiazepine-8-carboxamide 5-(R)-oxide

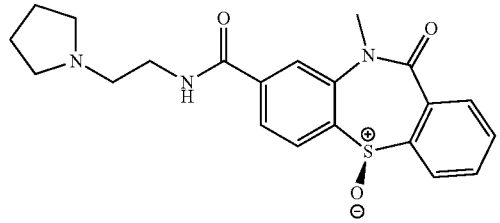 [SMILES: CN1C(=O)c2ccccc2[S@@+]([O-])c2ccc(C(=O)NCCN3CCCC3)cc21]

Separation of enantiomers via chiral HPLC: Analytical analysis was performed on a CHIRALPAK®IA® column (4.6×250 mm, 5 micron). The mobile phase was 60% of ethanol in hexanes at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=7.39 minutes; positive optical rotation. The second eluting peak: RT=11.48 minutes; negative optical rotation. Preparative separation was performed on a CHIRALPAK®IA® column (5×50 cm, 20 micron). The mobile phase was 60% of ethanol in hexanes at a flow rate of 35 mL/min with. Fraction collection was triggered by UV absorbance (254 nm). LCMS RT=3.35 min, m/z 398.1 [M+H$^+$]; HRMS (ESI) m/z calcd for $C_{21}H_{24}N_3O_3S$ [M+H$^+$] 398.1533, found 398.1538.

Example 123

N-(3,4-Dichlorobenzyl)-10-methyl-11-oxo-10,11-dihydrodibenzo[b,f][1,4]thiazepine-8-carboxamide 5-oxide

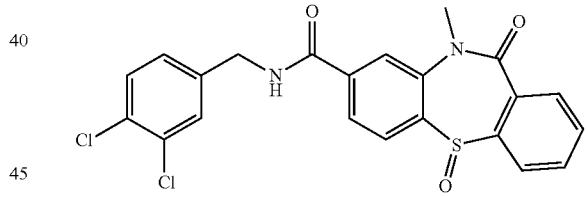

The title compound was prepared according to the general protocol B. LCMS RT=5.80 min, m/z 459.0 [M+H$^+$].

Example 124

8-Amino-10-ethyldibenzo[b,f][1,4]thiazepin-11 (10 H)-one 5-oxide

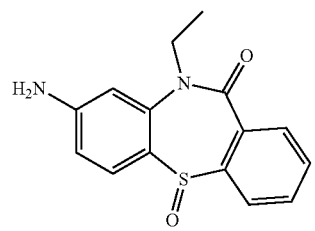 [SMILES: CCN1C(=O)c2ccccc2S(=O)c2ccc(N)cc21]

A mixture of 10-ethyl-11-oxo-10,11-dihydrodibenzo[b,f][1,4]thiazepine-8-carboxylic acid 5-oxide (73.0 mg, 0.23 mmol), diphenylphosphinyl azide (67.6 mg, 0.28 mmol), TEA (0.048 mL, 0.35 mmol) in dioxane (1.25 mL) was stirred at room temperature for 1 h. Water (1.04 mL, 57.9 mmol) was then added to the solution and the reaction mixture was heated at 80° C. for 4 h. The crude material was partitioned between EtOAc and saturated aqueous NaHCO$_3$ solution. The organic layer was washed with saturated brine, dried over MgSO$_4$, and concentrated under reduced pressure to give the crude title compound as a off-white foam which was used directly in the next reaction without further purification.

Example 125

(R)-N-(1-(4-Bromophenyl)ethyl)-10-ethyl-11-oxo-10,11-dihydrodibenzo[b,f][1,4]thiazepine-8-carboxamide 5-oxide

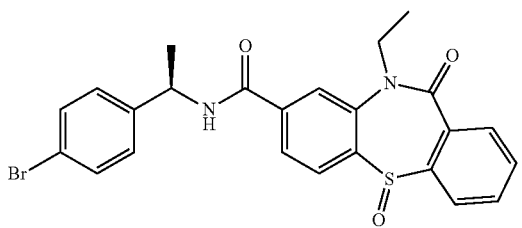 [SMILES: CCN1C(=O)c2ccccc2S(=O)c2ccc(C(=O)N[C@H](C)c3ccc(Br)cc3)cc21]

A solution of 10-ethyl-11-oxo-10,11-dihydrodibenzo[b,f][1,4]thiazepine-8-carboxylic acid 5-oxide (400 mg, 1.27 mmol) in DMF (12.0 mL) was treated at room temperature with HATU (965 mg, 2.54 mmol) and DIPEA (0.67 mL, 3.81 mmol). After stirring at room temperature for 5 min, (R)-1-(4-bromophenyl)ethanamine (508 mg, 2.54 mmol) was added to the solution. The reaction mixture was stirred at room temperature for an additional 4 h. The mixture was poured into cold HCl solution to induce the precipitation. The precipitation was filtered, washed with water and dried to give 560 mg (89%) of the title compound as a white solid. $^1$H NMR (400 MHz, DMSO-d$_6$) δ ppm 8.93 (d, J=7.8 Hz, 0.5 H), 8.92 (d, J=7.8 Hz, 0.5 H), 7.97-8.04 (m, 1 H), 7.91 (td, J=7.8, 1.6 Hz, 1 H), 7.66-7.74 (m, 3 H), 7.60-7.66 (m, 1 H), 7.55 (tt, J=7.4, 1.2 Hz, 1 H), 7.43-7.51 (m, 2 H), 7.25-7.34 (m, 2 H), 5.07 (qd, J=7.3, 7.0 Hz, 1 H), 4.49-4.67 (m, 1 H), 3.65-3.87 (m, 1 H), 1.43 (d, J=7.0 Hz, 1.5 H), 1.41 (d, J=7.0 Hz, 1.5 H), 1.18 (t, J=7.2 Hz, 1.5 H), 1.18 (t, J=7.2 Hz, 1.5 H); LCMS RT=6.02 min, m/z 497.1 [M+H$^+$]; HRMS (ESI) m/z calcd for C$_{24}$H$_{22}$BrN$_2$O$_3$S [M+H$^+$] 497.0529, found 497.0526.

Example 126

(R)-N-(1-(4-Bromophenyl)ethyl)-10-ethyl-11-oxo-10,11-dihydrodibenzo[b,f][1,4]thiazepine-8-carboxamide 5-(R)-oxide

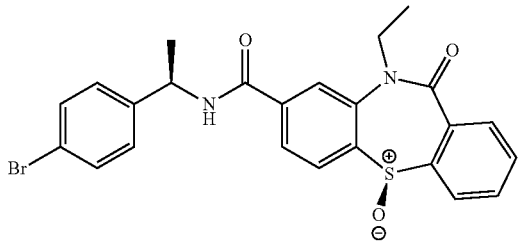

Separation of enantiomers via chiral HPLC: Analytical analysis was performed on a CHIRALPAK®IA® column (4.6×250 mm, 5 micron). The mobile phase was 60% of ethanol in hexanes at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=5.36 minutes; positive optical rotation. The second eluting peak: RT=6.44 minutes; negative optical rotation. Preparative separation was performed on a CHIRALPAK®IA® column (5×50 cm, 20 micron). The mobile phase was 60% of ethanol in hexanes at a flow rate of 35 mL/min. Fraction collection was triggered by UV absorbance (254 nm). The absolute configuration was assigned by X-ray diffraction. LCMS RT=6.02 min, m/z 497.0 [M+H$^+$]; HRMS (ESI) m/z calcd for C$_{24}$H$_{22}$BrN$_2$O$_3$S [M+H$^+$] 497.0529, found 497.0536.

Example 127

(R)-10-Ethyl-N-(1-(naphthalen-2-yl)ethyl)-11-oxo-10,11-dihydrodibenzo[b,f][1,4]thiazepine-8-carboxamide 5-oxide

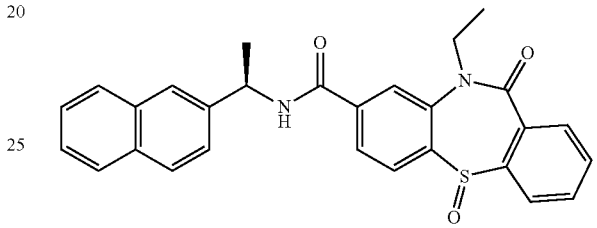

A solution of 10-ethyl-11-oxo-10,11-dihydrodibenzo[b,f][1,4]thiazepine-8-carboxylic acid 5-oxide (400 mg, 1.27 mmol) in DMF (12.0 mL) was treated at room temperature with HATU (965 mg, 2.54 mmol) and DIPEA (0.67 mL, 3.81 mmol). After stirring at room temperature for 5 min, (R)-1-(naphthalen-2-yl)ethanamine (434 mg, 2.54 mmol) was added to the solution. The reaction mixture was stirred at room temperature for an additional 4 h. The mixture was poured into cold HCl solution to induce the precipitation. The precipitation was filtered, washed with water and dried to give 464 mg (78%) of the title compound as a white solid. $^1$H NMR (400 MHz, DMSO-d$_6$) δ ppm 9.05 (d, J=7.4 Hz, 1 H), 8.06 (dd, J=9.0, 1.6 Hz, 1 H), 7.92-8.01 (m, 1 H), 7.80-7.91 (m, 4 H), 7.63-7.77 (m, 4 H), 7.52-7.62 (m, 2 H), 7.43-7.52 (m, 2 H), 5.20-5.40 (m, 1 H), 4.52-4.70 (m, 1 H), 3.78 (dq, J=13.9, 6.8 Hz, 1 H), 1.57 (d, J=6.8 Hz, 1.5 H), 1.56 (d, J=6.8 Hz, 3 H), 1.21 (t, J=7.0 Hz, 1.5 H), 1.20 (t, J=7.0 Hz, 1.5 H); LCMS RT=6.08 min, m/z 469.1 [M+H$^+$]; HRMS (ESI) m/z calcd for C$_{28}$H$_{25}$N$_2$O$_3$S [M+H$^+$] 469.1580, found 469.1580.

Example 128

(R)-10-Ethyl-N-(1-(naphthalen-2-yl)ethyl)-11-oxo-10,11-dihydrodibenzo[b,f][1,4]thiazepine-8-carboxamide 5-(R)-oxide

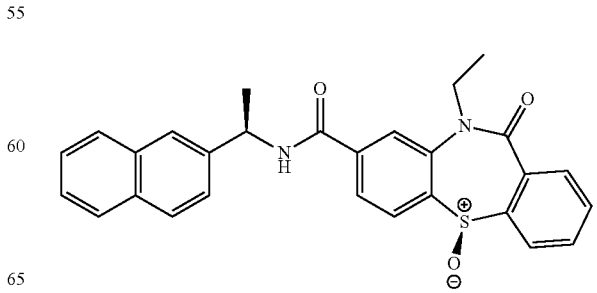

Separation of enantiomers via chiral HPLC: Analytical analysis was performed on a CHIRALPAK®IA® column (4.6×250 mm, 5 micron). The mobile phase was 60% of ethanol in hexanes at a flow rate of 1.0 mL/min with a run time of 15 minutes. The sample was detected with a diode array detector (DAD) at 220 nm and 254 nm. Optical rotation was determined with an in-line polarimeter (PDR-Chiral). The first eluting peak: RT=5.84 minutes; positive optical rotation. The second eluting peak: RT=7.19 minutes; negative optical rotation. Preparative separation was performed on a CHIRALPAK®IA® column (5×50 cm, 20 micron). The mobile phase was 60% of ethanol in hexanes at a flow rate of 35 mL/min. Fraction collection was triggered by UV absorbance (254 nm). LCMS RT=6.08 min, m/z 469.1 [M+H$^+$]; HRMS (ESI) m/z calcd for $C_{28}H_{25}N_2O_3S$ [M+H$^+$] 469.1580, found 469.1579.

Example 129

Additional Dopamine $D_2$ Selective Compounds

The compounds shown in Tables 6 to 11 were prepared by the synthetic method of Example 6. Those of skill in the art will recognize routine changes in reactants and reaction conditions needed to produce each particular compound. Compounds were tested in the dopamine $D_2$ calcium release assay provided in Example 1. All compounds shown in Table 6 exhibited an $AC_{50}$ of less than 10 micromolar in assay. Those indicated with an asterisk, *, exhibited an $AC_{50}$ of less than 1 micromolar in the dopamine $D_2$ calcium release assay.

TABLE 6

Additional Dopamine $D_2$ Selective Compounds

| Cmp. No. | $R_2$ | $Ca^{2+}$ $AC_{50}$ |
|---|---|---|
| 1 | 4-methoxybenzyl | * |
| 2 | 3-methoxybenzyl | * |
| 3 | (2-methoxyphenyl)methyl | |
| 4 | benzyl | * |
| 5 | 1-phenylethyl | * |
| 6 | 4-(methylthio)benzyl | * |
| 7 | 4-tert-butylbenzyl | * |
| 8 | 4-methylbenzyl | * |
| 9 | 4-(trifluoromethyl)benzyl | * |
| 10 | 4-fluorobenzyl | * |
| 11 | 4-chlorobenzyl | * |
| 12 | 4-cyanobenzyl | * |
| 13 | 4-(methylsulfonyl)benzyl | * |

TABLE 6-continued

Additional Dopamine D₂ Selective Compounds

| Cmp. No. | R₂ | Ca²⁺ AC₅₀ |
|---|---|---|
| 14 | 3,4,5-trimethoxybenzyl | |
| 15 | 1,3-benzodioxol-5-ylmethyl | * |
| 16 | benzyl | * |
| 17 | 4-methoxybenzyl | * |
| 18 | 4-methoxyphenethyl | * |

TABLE 7

Additional Dopamine D₂ Selective Compounds

| Cmp. No. | R₁ | Ca²⁺ AC₅₀ |
|---|---|---|
| 19 | H | |
| 20 | Methyl | * |
| 21 | n-Propyl | * |
| 22 | Benzyl | |

TABLE 8

Additional Dopamine D₂ Selective Compounds

| Cmp. No. | R₂ | Ca²⁺ AC₅₀ |
|---|---|---|
| 23 | phenyl | |
| 24 | 4-methoxyphenyl | * |
| 25 | Benzyl | * |
| 26 | 4-fluorobenzyl | * |
| 27 | 4-chlorobenzyl | * |
| 28 | 3-chlorobenzyl | * |
| 29 | 4-bromobenzyl | * |
| 30 | pyridin-2-ylmethyl | |
| 31 | pyridin-3-ylmethyl | * |
| 32 | 2-(thiophen-2-yl)ethyl | * |

TABLE 8-continued

Additional Dopamine D₂ Selective Compounds

| Cmp. No. | R₂ | Ca²⁺ AC₅₀ |
|---|---|---|
| 33 | pyrrolidinyl-ethyl | * |
| 34 | piperidinyl-ethyl | * |
| 35 | dimethylamino-propyl | * |

TABLE 9

Additional Dopamine D₂ Selective Compounds

| Cmp. No. | J | Ca²⁺ AC₅₀ |
|---|---|---|
| 36 | N-ethyl dibenzothiazepinone | * |
| 37 | N-ethyl dibenzothiazepinone S,S-dioxide | |
| 38 | N-ethyl dibenzothiazepinone S-oxide | * |
| 39 | N-ethyl dibenzothiazepinone S-oxide | |
| 40 | anthraquinonyl | |
| 41 | phthalimidophenyl | |

TABLE 10

Additional Dopamine D₂ Selective Compounds

| Cmp. No. | R₅ | L | Ca²⁺ AC₅₀ |
|---|---|---|---|
| 42 | Methoxy | N(CH₃)C(O) | |
| 43 | H | N(Et)C(O) | |

TABLE 10-continued

Additional Dopamine D₂ Selective Compounds

[Structure: R₅-phenyl-CH₂-L-(dibenzothiazepine core with N-ethyl, C=O, S=O)]

| Cmp. No. | R₅ | L | Ca²⁺ AC₅₀ |
|---|---|---|---|
| 44 | Methoxy | -O-C(=O)- | |
| 45 | Methoxy | -NH-C(=O)- | * |
| 46 | F | -NH-C(=O)- | * |

TABLE 11

Additional Dopamine D₂ Selective Compounds

[Structure: R₂-NH-C(=O)-aryl fused dibenzothiazepine with N-R₁, C=O, S(=O) with charges]

| Cmp. No. | R₁ | R₂ | Ca²⁺ AC₅₀ |
|---|---|---|---|
| 47 | Ethyl | 4-F-benzyl | * |
| 48 | Ethyl | 4-NC-benzyl | * |
| 49 | Ethyl | 1-(4-Br-phenyl)ethyl | * |
| 50 | Ethyl | 1-(naphth-2-yl)ethyl | * |
| 51 | Methyl | 4-Cl-benzyl | * |
| 52 | Methyl | 4-Br-benzyl | * |
| 53 | Methyl | pyridin-3-ylmethyl | * |
| 54 | Methyl | 2-(pyrrolidin-1-yl)ethyl | * |
| 55 | Methyl | 2-(thiophen-2-yl)ethyl | * |

Example 130

Selective Activity of Compounds

Certain compounds were tested in the D₂ beta arrestin assay of Example 2, the D₃ beta arrestin assay of Example 4, the D₂ binding assay of Example 3, the D₃ binding assay of Example 5. The ratio of D₃/D₂ activity in the beta arrestin and binding assay were calculated to determine compound activity.

TABLE 12

Selectivity Data

| Compound No. | D₃/D₂ beta-arrestin IC₅₀ ratio | D₃/D₂ binding $K_i$ ratio |
|---|---|---|
| 1 | 2.0 | 6.0 |
| 32 | 22.3 | 28.7 |
| 38 | 2.5 | N/A |

TABLE 12-continued

Selectivity Data

| Compound No. | $D_3/D_2$ beta-arrestin $IC_{50}$ ratio | $D_3/D_2$ binding $K_i$ ratio |
|---|---|---|
| 47 | 5.6 | 2.6 |
| 48 | 6.3 | 5.7 |
| 49 | 7.1 | 1.3 |
| 50 | 11.2 | 16.2 |
| 51 | 4.5 | N/A |
| 52 | 4.6 | 1.5 |
| 53 | 5.0 | 70.0 |
| 54 | 7.2 | 1.7 |
| R-55 | N/A | N/A |
| 55 | 17.8 | 29.0 |

Figure 1B:
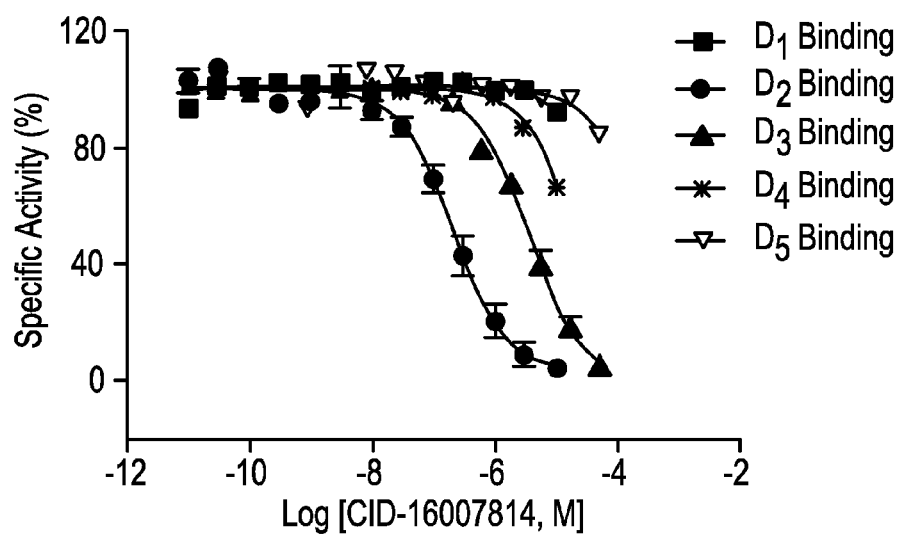
Figure 2A:
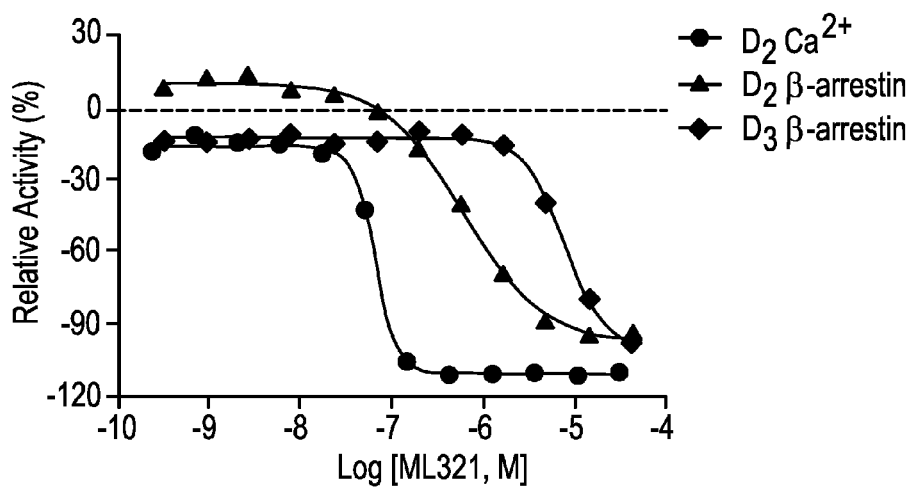
FIG. 2. (A) Graphical representation of the dose response curves of Compound 55 in $D_2$ $Ca^{2+}$ assay (circles, $AC_{50}$=0.070 µM), $D_2$ β-arrestin assay (triangles, $AC_{50}$=0.725 µM), and $D_3$ β-arrestin assay (diamonds, $AC_{50}$=12.9 µM). (B) Graphical representation of the dose response curves of Compound 55 in binding assays for $D_1$ (squares, $K_i$=67.1 µM), $D_2$ (circles, $K_i$=0.1 µM), $D_3$ (solid triangles, $K_i$=2.9 µM), $D_4$ (stars, $K_i$=8.48 µM) and $D_5$ (invented triangles).
Figure 2B:
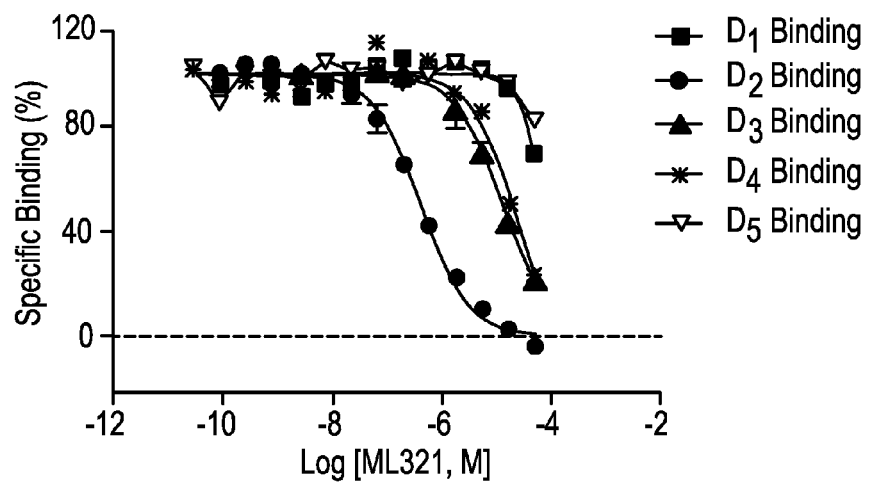

Graphical representation of the beta-arrestin and radioligand binding assay data in Table 12 for compounds 1 and 55 can be seen in FIGS. 1 and 2.

The above data show that this series of compounds can achieve significant potency/affinity separation from the $D_3$ dopamine receptor, which is a highly novel finding that may have therapeutic impact. Because all FDA approved drugs that target the $D_2$ receptor, particularly those that antagonize the receptor, such as antipsychotics, exhibit cross GPCR reactivity, a fact that may contribute to their well-known side effects, it was of interest to profile one compound against a panel of GPCRs. Table 13 shows an affinity profile of compound 55 against a panel of 46 GPCRs and related proteins. Antipsychotic drugs (depending on the specific drug) typically interact with a range of serotonergic, adrenergic, histaminergic, and muscarinic receptors. In contrast, compound 55 was found to bind with significant affinity (inhibition of binding >50%) to only two serotonin receptors and the $D_2$ and $D_3$ receptors. Notably, the affinity for the two serotonin receptors was similar to that for the $D_3$ receptor, indicating compound 55 is very highly selective for the $D_2$ receptor.

TABLE 13

| Receptor | Inhibition (%) | Receptor | Inhibition (%) | Receptor | Inhibition (%) |
|---|---|---|---|---|---|
| 5-HT1A | 8.2 | Beta1 | 12.6 | H1 | 41.6 |
| 5-HT1B | 24.0 | Beta2 | -13.2 | H2 | -9.2 |
| 5-HT1D | 13.1 | Beta3 | 6.6 | H3 | -23.6 |
| 5-HT1E | 9.9 | BZP Rat Brain Site | 0.5 | H4 | TBD |
| 5-HT2A | 46.3 | GABAA | 10.6 | KOR | 18.2 |
| 5-HT2B | 40.1 | D1 | -6.8 | M1 | -0.6 |
| 5-HT2C | 64.5 | D2 | 923 | M2 | -1.7 |
| 5-HT3 | 8.5 | D3 | 59.1 | M3 | 5.2 |
| 5-HT4 | TBD | D4 | 32.2 | M4 | 2.4 |
| 5-HT5A | 9.5 | D5 | -8.5 | M5 | -6.5 |
| 5-HT6 | -15.6 | DAT | -5.3 | MOR | 5.7 |
| 5-HT7 | 53.3 | DOR | -23.6 | NET | 8.9 |
| Alpha1A | -13.4 | | | PBR | 31 |
| Alpha1B | -0.2 | | | SERT | 4.8 |
| Alpha1D | -22.6 | | | Sigma 1 | 17.5 |
| Alpha2A | 7.3 | | | Sigma 2 | -16.5 |
| Alpha2B | 31.2 | | | | |
| Alpha2C | 20.9 | | | | |

Example 131

Pet Study, Displacement of the D2 Receptor Label [$^{11}$C]SV-130 with a Compound of Formula I Positron emission tomography (PET) was performed using live monkeys. A radioactive PET probe ([$^{11}$C]SV-130) for the D2 receptor was injected intravenously. PET images of coronal sections of the brain were obtained at the level of the caudate putamen. In the baseline imaging section, the PET probe showed high uptake in the caudate putamen, with areas of high D2 receptor expression appearing orange-red in the baseline images. Monkeys were treated (i.v.) with either 1 mg/kg or 5 mg/kg ML321, a compound of Formula I (compound 55, Example 61).

Summed MicroPET coronal images of the caudate putamen taken from 20 to 100 minutes post ML321 injection showed that ML321 blocks the binding of the D2 receptor PET probe in the caudate putamen in a dose-dependent fashion. The 5 mg/kg dose almost completely blocked the ([$^{11}$C]SV-130) labeling.

The time course of PET ([$^{11}$C]SV-130) labelling of the caudate, putamen, and cerebellumum in the absence or presence of either 1 mg/kg or 5 mg/kg ML321 was plotted. In both the caudate and putamen the graphs showed uptake of [$^{11}$C]SV-130 and a continued strong signal from the labelled probe over the 100 minute period plotted. When ML321 was injected i.v. the [$^{11}$C]SV-130 signal decreased gradually from about 20 minutes through the 100 minute observation period. The [$^{11}$C]SV-130 signal decrease was particularly dose dependent in the putamen graph. The cerebellum graph was used as a negative control as this brain region lacks D2 receptors and exhibits only non-specific uptake of the probe.

The significance of the PET [$^{11}$C]SV-130 labelling data are two-fold. First the experiments provide direct evidence that ML321 can cross the blood-brain barrier in primates and interact with regions of the brain containing high levels of D2 receptors. Second, the experiments provide direct evidence that ML321 can occupy D2 receptors in the CNS in living animals and completely block D2 receptors at a reasonable pharmacological dose.

Example 132

Behavioral Effects of a Compound of Formula I

These experiments test the ability of a compound of Formula I, ML321, to affect physiological or behavioral responses in rats that are mediated by D2 or D3 receptors. Sumanirole, an agonist of the D2 receptor, produces hypothermia in rats when administered subcutaneously. This response is known to be mediated by the D2 receptor and not the D3 receptor (Collins et al., Psychopharmacology (Berl). 2007, 193(2):159-70). ML321 was found to significantly and dose-dependently block the sumanirole-induced hypothermia response when administered subcutaneously at doses of 3.2 and 10 mg/kg. The response was completely blocked at 10 mg/kg.

Pramipexole, an agonist of the D3 receptor, produces yawning when administered subcutaneously. This response is known to be mediated by the D3 receptor and not the D2 receptor (Collins, Id.). ML321 was found to have no effect on pramipexole-induced yawning using the same doses that blocked the hypothermia response (3.2 and 10 mg/kg). Observations of the pramipexole-induced yawning over an extended time period in the presence or absence of ML321 confirmed that ML321 had no effect on pramipexole-induced yawning.

The sumanirole-induced hypothermia and pramipexole-induced yawning experiments show ML321 can act selectively to block the D2 receptor without blocking the D3 receptor when administered to living animals. Thus, the D2 selectivity identified using cellular assays can also be seen in living animals.

What is claimed is:
1. A compound of the formula:

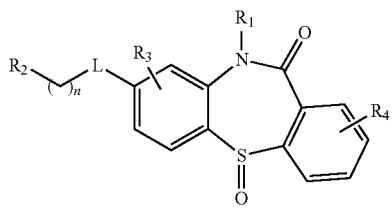

or a pharmaceutically acceptable salt thereof, wherein
L is —NHC(O)—, —C(O)NH—, —OC(O)— or —C(O)O—;
n is and integer from 1 to 4 and

is unsubstituted or substituted with one or more substituents independently chosen from halogen, hydroxyl, amino, cyano, $C_1$-$C_4$alkyl, $C_1$-$C_4$alkoxy, $C_1$-$C_2$haloalkyl, or $C_1$-$C_2$haloalkoxy;
$R_1$ is hydrogen, $C_1$-$C_6$alkyl, $C_2$-$C_6$alkenyl, ($C_3$-$C_7$cycloalkyl)$C_0$-$C_2$alkyl, (mono- or di-$C_1$-$C_4$alkylamino)$C_1$-$C_4$alkyl, or (mono- or di-$C_1$-$C_4$alkylamino)$C_1$-$C_4$ alkoxy;
$R_2$ is mono-, bi-, or tricyclic carbocyclic or aromatic heterocylic group, a (mono- or di-$C_1$-$C_4$alkylamino) $C_2$-$C_4$alkyl group, or $C_4$-$C_8$alkyl, each of which $R_2$ is unsubstituted or substituted with one more substituents independently chosen from halogen, hydroxyl, amino, nitro, cyano, $C_1$-$C_6$alkyl, $C_2$-$C_6$alkenyl, $C_2$-$C_6$alkynyl, —$OR_{11}$, —$(CH_2)_{0-4}C(O)R_{11}$, —$(CH_2)_{0-4}NR_{11}R_{12}$, —$(CH_2)_{0-4}C(O)NR_{11}R_{12}$, —$(CH_2)_{0-4}N(R_{11})C(O)(R_{12})$, —$(CH_2)_{0-4}C(O)OR_{11}$, —$(CH_2)_{0-4}OC(O)R_{11}$, —$(CH_2)_{0-4}C(S)R_{11}$, —$(CH_2)_{0-4}S(O)_aR_{11}$, —$(CH_2)_{0-4}S(O)_bNR_{11}R_{12}$, —$(CH_2)_{0-4}N(R_{11})S(O)_bR_{12}$, and (phenyl)$C_0$-$C_2$alkyl, where a is 0, 1, or 2, and b is 1 or 2,
$R_{11}$ and $R_{12}$ are independently chosen at each occurrence from hydrogen and a $C_1$-$C_6$aliphatic group;
each of $R_{11}$, and $R_{12}$ is unsubstituted or substituted with one or more substituents independently chosen from: halogen, hydroxyl, vinyl, allenyl, oxo, cyano, amino, —COOH, $C_1$-$C_6$alkyl, $C_1$-$C_6$alkoxy, (mono- and di-$C_1$-$C_6$alkylamino)$C_0$-$C_2$alkyl, $C_1$-$C_6$alkylester, $C_1$-$C_6$alkylthio, $C_1$-$C_2$haloalkyl, and $C_1$-$C_2$haloalkoxy;
$R_3$ and $R_4$ are 0 or 1 or more substituents independently chosen from halogen, hydroxyl, amino, cyano, $C_1$-$C_4$alkyl, $C_1$-$C_4$alkoxy, $C_2$-$C_4$alkanoyl, (mono- and di-$C_1$-$C_4$alkylamino)$C_0$-$C_2$alkyl, $C_1$-$C_2$haloalkyl, and $C_1$-$C_2$haloalkoxy;
with the proviso that when $R_1$ is ethyl, the group

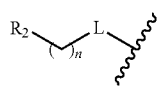

is not 4-methoxybenzyl-NHC(O)—, pyridin-2-ylmethyl-NHC(O)—, 3-(morpholin-1-yl)propyl-NHC(O)—, 3-(azepan-1-yl)propyl-NHC(O)—, 2-(azepan-1-yl)ethyl-NHC(O)—, 3-(pyrrolidin-1-yl)propyl-NHC(O)—, 3-(4-methylpiperazin-1-yl)propyl-NHC(O)—, 3-(piperidin-1-yl)propyl-NHC(O)—, di-isopropylaminopropyl-NHC(O)—, di-propylaminopropyl-NHC(O)—, di-butylaminopropyl-NHC(O)—, or 3-(butyl(ethyl)amino)propyl-NHC(O)—.

2. A compound or salt of claim 1, of the formula

3. A compound or salt of claim 1, of the formula

4. A compound or salt of claim 1, of the formula

5. A compound or salt of claim 1, wherein
$R_1$ is $C_1$-$C_6$alkyl, $C_2$-$C_6$alkenyl, or ($C_3$-$C_7$cycloalkyl)$C_0$-$C_2$alkyl.

6. A compound or salt of claim 5 wherein $R_1$ is $C_1$-$C_6$alkyl.

7. A compound or salt of claim 1, wherein
$R_1$ is methyl or ethyl, and $R_3$ and $R_4$ are both 0 substituents.

8. A compound or salt of claim 1, wherein
$R_3$ and $R_4$ are both 0, 1, or 2 substituents independently chosen from halogen, hydroxyl, amino, cyano, $C_1$-$C_2$alkyl, $C_1$-$C_2$alkoxy, trifluoromethyl, difluoromethoxy, and trifluoromethoxy.

9. A compound or salt of claim 1, wherein n is 1, 2, or 3 and is unsubstituted or substituted with one $C_1$-$C_4$alkyl substituent or one trifluoromethyl substituent.

10. A compound or salt of claim 9, wherein n is 1 or 2 and

is unsubstituted or substituted with one methyl substituent.

11. A compound or salt of claim 9, wherein
$R_2$ is $C_3$-$C_7$cycloalkyl, phenyl, naphthyl, phenyl fused to a 5- or 6-membered heterocyclic ring containing 1 or 2 oxygen atoms, pyridyl, pyrimidinyl, pyrazinyl, thienyl, furanyl, thiazolyl, indolyl, or imidazolyl, each of which $R_2$ is unsubstituted or substituted with one or more substituents independently chosen from halogen, hydroxyl, amino, cyano, $C_1$-$C_4$alkyl, $C_1$-$C_4$alkoxy, (mono- and di-$C_1$-$C_4$alkylamino)$C_0$-$C_2$alkyl, $C_1$-$C_4$alkylthio, $C_1$-$C_4$alkylsulfonyl, $C_1$-$C_2$haloalkyl, and $C_1$-$C_2$haloalkoxy.

12. A compound or salt of claim 11, wherein
$R_2$ is phenyl, naphthyl, benzo[d][1,3]dioxolyl, pyridyl, thienyl, furanyl, indolyl, imidazolyl, or thiazolyl, each which is substituted with one or more substituents independently chosen from halogen, hydroxyl, amino, cyano, $C_1$-$C_4$alkyl, $C_1$-$C_4$alkoxy, (mono- and di-$C_1$-$C_4$alkylamino)$C_0$-$C_2$alkyl, $C_1$-$C_4$alkylthio, $C_1$-$C_4$alkylsulfonyl, $C_1$-$C_2$haloalkyl, and $C_1$-$C_2$haloalkoxy.

13. A compound or salt of claim 11, wherein
$R_2$ is phenyl, naphthyl, benzo[d][1,3]dioxolyl, pyridyl, or thienyl, each which is substituted with one or more substituents independently chosen from halogen, hydroxyl, cyano, $C_1$-$C_4$alkyl, $C_1$-$C_4$alkoxy, methylthio, methylsulfonyl, trifluoromethyl, and trifluoromethoxy.

14. A compound or salt of claim 3, wherein
$R_1$ is $C_1$-$C_6$alkyl, or ($C_3$-$C_7$cycloalkyl)$C_0$-$C_2$alkyl;
n is 1, 2, or 3 and

is unsubstituted or substituted with one $C_1$-$C_4$alkyl substituent or one trifluoromethyl substituent; and
$R_2$ is phenyl, naphthyl, benzo[d][1,3]dioxolyl, pyridyl, thienyl, furanyl, indolyl, imidazolyl, or thiazolyl, each which is unsubstituted or substituted with one or more substituents independently chosen from halogen, hydroxyl, amino, cyano, $C_1$-$C_4$alkyl, $C_1$-$C_4$alkoxy, (mono- and di-$C_1$-$C_4$alkylamino)$C_0$-$C_2$alkyl, $C_1$-$C_4$alkylthio, $C_1$-$C_4$alkylsulfonyl, $C_1$-$C_2$haloalkyl, and $C_1$-$C_2$haloalkoxy; and
$R_3$ and $R_4$ are both 0 substituents.

15. A compound or salt of claim 14, wherein
$R_2$ is thienyl, which is unsubstituted or substituted with one or more substituents independently chosen from halogen, $C_1$-$C_2$alkyl, or $C_1$-$C_2$alkoxy.

16. A compound or salt of claim 14, wherein
$R_2$ is phenyl which is unsubstituted or substituted with one or more substituents independently chosen from halogen, hydroxyl, amino, cyano, $C_1$-$C_4$alkyl, $C_1$-$C_4$alkoxy, (mono- and di-$C_1$-$C_4$alkylamino)$C_0$-$C_2$alkyl, $C_1$-$C_4$alkylthio, $C_1$-$C_4$alkylsulfonyl, $C_1$-$C_2$haloalkyl, and $C_1$-$C_2$haloalkoxy.

17. A compound or pharmaceutically acceptable salt thereof, wherein the compound is
10-Ethyl-N-(4-methoxybenzyl)-11-oxo-10,11-dihydrodibenzo[b,f][1,4]thiazepine-8-carboxamide 5-oxide;
10-Ethyl-N-(3-methoxybenzyl)-11-oxo-10,11-dihydrodibenzo[b,f][1,4]thiazepine-8-carboxamide 5-oxide;
10-Ethyl-N-(2-methoxybenzyl)-11-oxo-10,11-dihydrodibenzo[b,f][1,4]thiazepine-8-carboxamide 5-oxide;
N-Benzyl-10-ethyl-11-oxo-10,11-dihydrodibenzo[b,f][1,4]thiazepine-8-carboxamide 5-oxide;
10-Ethyl-11-oxo-N-(1-phenylethyl)-10,11-dihydrodibenzo[b,f][1,4]thiazepine-8-carboxamide 5-oxide;
10-Ethyl-N-(4-(methylthio)benzyl)-11-oxo-10,11-dihydrodibenzo[b,f][1,4]thiazepine-8-carboxamide 5-oxide;
N-(4-tert-Butylbenzyl)-10-ethyl-11-oxo-10,11-dihydrodibenzo[b,f][1,4]thiazepine-8-carboxamide 5-oxide;
10-Ethyl-N-(4-methylbenzyl)-11-oxo-10,11-dihydrodibenzo[b,f][1,4]thiazepine-8-carboxamide 5-oxide;
10-Ethyl-11-oxo-N-(4-(trifluoromethyl)benzyl)-10,11-dihydrodibenzo[b,f][1,4]thiazepine-8-carboxamide 5-oxide;
10-Ethyl-N-(4-fluorobenzyl)-11-oxo-10,11-dihydrodibenzo[b,f][1,4]thiazepine-8-carboxamide 5-oxide;
N-(4-Cyanobenzyl)-10-ethyl-11-oxo-10,11-dihydrodibenzo[b,f][1,4]thiazepine-8-carboxamide 5-oxide;
10-Ethyl-N-(4-(methylsulfonyl)benzyl)-11-oxo-10,11-dihydrodibenzo[b,f][1,4]thiazepine-8-carboxamide 5-oxide;
10-Ethyl-11-oxo-N-(3,4,5-trimethoxybenzyl)-10,11-dihydrodibenzo[b,f][1,4]thiazepine-8-carboxamide 5-oxide;
N-(benzo[d][1,3]dioxol-5-ylmethyl)-10-ethyl-11-oxo-10,11 dihydrodibenzo[b,f][1,4]thiazepine-8-carboxamide 5-oxide;
10-Ethyl-11-oxo-N-phenyl-10,11-dihydrodibenzo[b,f][1,4]thiazepine-8-carboxamide 5-oxide;
10-Ethyl-N-(4-methoxyphenyl)-11-oxo-10,11-dihydrodibenzo[b,f][1,4]thiazepine-8-carboxamide 5-oxide;
10-Ethyl-N-(4-methoxyphenethyl)-11-oxo-10,11-dihydrodibenzo[b,f][1,4]thiazepine-8-carboxamide 5-oxide;
N-(4-Methoxybenzyl)-11-oxo-10,11-dihydrodibenzo[b,f][1,4]thiazepine-8-carboxamide 5-oxide;
N-(4-Methoxybenzyl)-10-methyl-11-oxo-10,11-dihydrodibenzo[b,f][1,4]thiazepine-8-carboxamide 5-oxide;
N-(4-Methoxybenzyl)-11-oxo-10-propyl-10,11-dihydrodibenzo[b,f][1,4]thiazepine-8-carboxamide 5-oxide;
10-Benzyl-N-(4-methoxybenzyl)-11-oxo-10,11-dihydrodibenzo[b,f][1,4]thiazepine-8-carboxamide 5-oxide;
10-Methyl-11-oxo-N-phenyl-10,11-dihydrodibenzo[b,f][1,4]thiazepine-8-carboxamide 5-oxide;
N-(4-Methoxyphenyl)-10-methyl-11-oxo-10,11-dihydrodibenzo[b,f][1,4]thiazepine-8-carboxamide 5-oxide;
N-Benzyl-10-methyl-11-oxo-10,11-dihydrodibenzo[b,f][1,4]thiazepine-8-carboxamide 5-oxide;
N-(4-Fluorobenzyl)-10-methyl-11-oxo-10,11-dihydrodibenzo[b,f][1,4]thiazepine-8-carboxamide 5-oxide;
N-(4-Chlorobenzyl)-10-methyl-11-oxo-10,11-dihydrodibenzo[b,f][1,4]thiazepine-8-carboxamide 5-oxide;
N-(3-Chlorobenzyl)-10-methyl-11-oxo-10,11-dihydrodibenzo[b,f][1,4]thiazepine-8-carboxamide 5-oxide;

N-(4-Bromobenzyl)-10-methyl-11-oxo-10,11-dihydrodibenzo[b,f][1,4]thiazepine-8-carboxamide 5-oxide;
10-Methyl-11-oxo-N-(pyridin-2-ylmethyl)-10,11-dihydrodibenzo[b,f][1,4]thiazepine-8-carboxamide 5-oxide;
10-Methyl-11-oxo-N-(pyridin-3-ylmethyl)-10,11-dihydrodibenzo[b,f][1,4]thiazepine-8-carboxamide 5-oxide;
10-Methyl-11-oxo-N-(2-(thiophen-2-yl)ethyl)-10,11-dihydrodibenzo[b,f][1,4]thiazepine-8-carboxamide 5-oxide;
10-Methyl-11-oxo-N-(2-(pyrrolidin-1-yl)ethyl)-10,11-dihydrodibenzo[b,f][1,4]thiazepine-8-carboxamide 5-oxide;
10-Methyl-11-oxo-N-(2-(piperidin-1-yl)ethyl)-10,11-dihydrodibenzo[b,f][1,4]thiazepine-8-carboxamide 5-oxide;
N-(3-(Dimethylamino)propyl)-10-methyl-11-oxo-10,11-dihydrodibenzo[b,f][1,4]thiazepine-8-carboxamide 5-oxide;
10-Ethyl-N-(4-methoxybenzyl)-11-oxo-10,11-dihydrodibenzo[b,f][1,4]thiazepine-8-carboxamide;
N-(4-Methoxybenzyl)-11-oxo-10,11-dihydrodibenzo[b,f][1,4]thiazepine-8-carboxamide 5,5-dioxide;
10-Ethyl-N-(4-methoxybenzyl)-11-oxo-10,11-dihydrodibenzo[b,f][1,4]thiazepine-8-carboxamide 5-(S)-oxide;
10-Ethyl-N-(4-methoxybenzyl)-11-oxo-10,11-dihydrodibenzo[b,f][1, 4]thiazepine-8-carboxamide 5-(R)-oxide;
10-Ethyl-N-(4-methoxybenzyl)-N-methyl-11-oxo-10,11-dihydrodibenzo[b,f][1,4]thiazepine-8-carboxamide 5-oxide;
N-Benzyl-N,10-diethyl-11-oxo-10,11-dihydrodibenzo[b,f][1,4]thiazepine-8-carboxamide 5-oxide;
4-Methoxybenzyl 10-ethyl-11-oxo-10,11-dihydrodibenzo[b,f][1,4]thiazepine-8-carboxylate 5-oxide;
N-(10-Ethyl-11-oxo-10,11-dihydrodibenzo[b,f][1,4]thiazepin-8-yl)-2-(4-methoxyphenyl)acetamide 5-oxide;
N-(10-Ethyl-11-oxo-10,11-dihydrodibenzo[b,f][1,4]thiazepin-8-yl)-2-(4-fluorophenyl)acetamide 5-oxide;
10-Ethyl-N-(4-fluorobenzyl)-11-oxo-10,11-dihydrodibenzo[b,f][1,4]thiazepine-8-carboxamide 5-(S)-oxide;
N-(4-Cyanobenzyl)-10-ethyl-11-oxo-10,11-dihydrodibenzo[b,f][1,4]thiazepine-8-carboxamide 5-(S)-oxide;
(R)-N-(1-(4-Bromophenyl)ethyl)-10-ethyl-11-oxo-10,11-dihydrodibenzo[b,f][1,4]thiazepine-8-carboxamide 5-(S)-oxide;
(R)-10-Ethyl-N-(1-(naphthalen-2-yl)ethyl)-11-oxo-10,11-dihydrodibenzo[b,f][1,4]thiazepine-8-carboxamide 5-(S)-oxide;
N-(4-Chlorobenzyl)-10-methyl-11-oxo-10,11-dihydrodibenzo[b,f][1,4]thiazepine-8-carboxamide 5-(S)-oxide;
N-(4-Bromobenzyl)-10-methyl-11-oxo-10,11-dihydrodibenzo[b,f][1,4]thiazepine-8-carboxamide 5-(S)-oxide;
10-Methyl-11-oxo-N-(pyridin-3-ylmethyl)-10,11-dihydrodibenzo[b,f][1,4]thiazepine-8-carboxamide 5-(S)-oxide;
10-Methyl-11-oxo-N-(2-(pyrrolidin-1-yl)ethyl)-10,11-dihydrodibenzo[b,f][1,4]thiazepine-8-carboxamide 5-(S)-oxide;
10-Ethyl-11-oxo-N-(2-(thiophen-2-yl)ethyl)-10,11-dihydrodibenzo[b,f][1,4]thiazepine-8-carboxamide 5-oxide;
10-Methyl-11-oxo-N-(2-(thiophen-2-yl)ethyl)-10,11-dihydrodibenzo[b,f][1,4]thiazepine-8-carboxamide 5-(S)-oxide;
Benzyl 10-benzyl-11-oxo-10,11-dihydrodibenzo[b,f][1,4]thiazepine-8-carboxylate 5-oxide;
N-(4-Methoxybenzyl)-11-oxo-10,11-dihydrodibenzo[b,f][1,4]thiazepine-8-carboxamide;
10-Ethyl-11-oxo-N-(3-(trifluoromethyl)benzyl)-10,11-dihydrodibenzo[b,f][1,4]thiazepine-8-carboxamide 5-oxide;
10-Ethyl-N-(3-methylbenzyl)-11-oxo-10,11-dihydrodibenzo[b,f][1,4]thiazepine-8-carboxamide 5-oxide;
N-(3-Chlorobenzyl)-10-ethyl-11-oxo-10,11-dihydrodibenzo[b,f][1,4]thiazepine-8-carboxamide 5-oxide;
N-(Biphenyl-3-ylmethyl)-10-ethyl-11-oxo-10,11-dihydrodibenzo[b,f][1,4]thiazepine-8-carboxamide 5-oxide;
10-Ethyl-11-oxo-N-(3-phenylpropyl)-10,11-dihydrodibenzo[b,f][1,4]thiazepine-8-carboxamide 5-oxide;
N-(2,3-Dimethoxybenzyl)-10-ethyl-11-oxo-10,11-dihydrodibenzo[b,f][1,4]thiazepine-8-carboxamide 5-oxide;
10-Ethyl-11-oxo-N-(thiophen-2-ylmethyl)-10,11-dihydrodibenzo[b,f][1,4]thiazepine-8-carboxamide 5-oxide;
10-Ethyl-N-(furan-2-ylmethyl)-11-oxo-10,11-dihydrodibenzo[b,f][1,4]thiazepine-8-carboxamide 5-oxide;
10-Ethyl-N-((4-methylthiophen-2-yl)methyl)-11-oxo-10,11-dihydrodibenzo[b,f][1,4]thiazepine-8-carboxamide 5-oxide;
10-Ethyl-N-(2-morpholinoethyl)-11-oxo-10,11-dihydrodibenzo[b,f][1,4]thiazepine-8-carboxamide 5-oxide;
10-Ethyl-N-((1-methylpiperidin-4-yl)methyl)-11-oxo-10,11-dihydrodibenzo[b,f][1,4]thiazepine-8-carboxamide 5-oxide;
N-(2-Chlorobenzyl)-10-ethyl-11-oxo-10,11-dihydrodibenzo[b,f][1,4]thiazepine-8-carboxamide 5-oxide;
10-Ethyl-11-oxo-N-(2-(trifluoromethyl)benzyl)-10,11-dihydrodibenzo[b,f][1,4]thiazepine-8-carboxamide 5-oxide;
N-(2,3-Dihydrobenzo[b][1,4]dioxin-6-yl)-10-ethyl-11-oxo-10,11-dihydrodibenzo[b,f][1,4]thiazepine-8-carboxamide 5-oxide;
10-Ethyl-N-(2-methylbenzyl)-11-oxo-10,11-dihydrodibenzo[b,f][1,4]thiazepine-8-carboxamide 5-oxide;
N-(2,5-Dimethoxybenzyl)-10-ethyl-11-oxo-10,11-dihydrodibenzo[b,f][1,4]thiazepine-8-carboxamide 5-oxide;
N-((1H-Indol-6-yl)methyl)-10-ethyl-11-oxo-10,11-dihydrodibenzo[b,f][1,4]thiazepine-8-carboxamide 5-oxide;
N-(2,4-Dimethoxybenzyl)-10-ethyl-11-oxo-10,11-dihydrodibenzo[b,f][1,4]thiazepine-8-carboxamide 5-oxide;
N-(4-Cyanobenzyl)-10-ethyl-11-oxo-10,11-dihydrodibenzo[b,f][1,4]thiazepine-8-carboxamide 5-(R)-oxide;
N-(2,6-Dimethoxybenzyl)-10-ethyl-11-oxo-10,11-dihydrodibenzo[b,f][1,4]thiazepine-8-carboxamide 5-oxide;
10-Ethyl-N-(4-fluorobenzyl)-11-oxo-10,11-dihydrodibenzo[b,f][1,4]thiazepine-8-carboxamide 5-(R)-oxide;
10-Ethyl-N-isobutyl-11-oxo-10,11-dihydrodibenzo[b,f][1,4]thiazepine-8-carboxamide 5-oxide;
10-Ethyl-N-(4-methylphenethyl)-11-oxo-10,11-dihydrodibenzo[b,f][1,4]thiazepine-8-carboxamide 5-oxide;
10-Ethyl-11-oxo-N-(4-phenylbutyl)-10,11-dihydrodibenzo[b,f][1,4]thiazepine-8-carboxamide 5-oxide;

10-Ethyl-N-(2-(furan-2-yl)propyl)-11-oxo-10,11-dihydrodibenzo[b,f][1,4]thiazepine-8-carboxamide 5-oxide;
N-((1H-Imidazol-2-yl)methyl)-10-ethyl-11-oxo-10,11-dihydrodibenzo[b,f][1,4]thiazepine-8-carboxamide 5-oxide;
10-Ethyl-N-(2-(2-methylthiazol-4-yl)ethyl)-11-oxo-10,11-dihydrodibenzo[b,f][1,4]thiazepine-8-carboxamide 5-oxide;
10-Ethyl-N-(3-methoxyphenethyl)-11-oxo-10,11-dihydrodibenzo[b,f][1,4]thiazepine-8-carboxamide 5-oxide;
N-(1-Adamantyl)-10-ethyl-11-oxo-10,11-dihydrodibenzo[b,f][1,4]thiazepine-8-carboxamide 5-oxide;
10-Ethyl-N-((1-methyl-1H-imidazol-5-yl)methyl)-11-oxo-10,11-dihydrodibenzo[b,f][1,4]thiazepine-8-carboxamide 5-oxide;
10-Ethyl-N-((2-methylthiazol-4-yl)methyl)-11-oxo-10,11-dihydrodibenzo[b,f][1,4]thiazepine-8-carboxamide 5-oxide;
10-Ethyl-N-((1-methyl-1H-imidazol-4-yl)methyl)-11-oxo-10,11-dihydrodibenzo[b,f][1,4]thiazepine-8-carboxamide 5-oxide;
10-Ethyl-N-(5-methylthiazol-2-yl)-11-oxo-10,11-dihydrodibenzo[b,f][1,4]thiazepine-8-carboxamide 5-oxide;
(E)-2-(8-Chlorodibenzo[b,f]thiepin-10-yloxy)-N,N-dimethylethanamine 5-oxide;
(E)-2-(8-chlorodibenzo[b,f]thiepin-10-yloxy)-N,N-dimethylethanamine 5,5-dioxide;
10-Ethyl-N-(3-fluorobenzyl)-11-oxo-10,11-dihydrodibenzo[b,f][1,4]thiazepine-8-carboxamide 5-oxide;
N-(3-(Dimethylamino)propyl)-10-ethyl-11-oxo-10,11-dihydrodibenzo[b,f][1,4]thiazepine-8-carboxamide 5-oxide;
N-(4-Aminophenethyl)-10-ethyl-11-oxo-10,11-dihydrodibenzo[b,f][1,4]thiazepine-8-carboxamide 5-oxide;
N-(4-Methoxybenzyl)-11-oxo-10,11-dihydrodibenzo[b,f][1,4]thiazepine-8-carboxamide 5,5-dioxide;
N-(4-Chlorobenzyl)-10-methyl-11-oxo-10,11-dihydrodibenzo[b,f][1,4]thiazepine-8-carboxamide 5-(R)-oxide;
N-(4-Bromobenzyl)-10-methyl-11-oxo-10,11-dihydrodibenzo[b,f][1,4]thiazepine-8-carboxamide 5-(R)-oxide;
N-(4-Iodobenzyl)-10-methyl-11-oxo-10,11-dihydrodibenzo[b,f][1,4]thiazepine-8-carboxamide 5-oxide;
N-(3-Fluorobenzyl)-10-methyl-11-oxo-10,11-dihydrodibenzo[b,f][1,4]thiazepine-8-carboxamide 5-oxide;
10-Methyl-11-oxo-N-(2-(thiophen-2-yl)ethyl)-10,11-dihydrodibenzo[b,f][1,4]thiazepine-8-carboxamide 5-(R)-oxide;
(S)-10-Methyl-11-oxo-N-(1-phenylethyl)-10,11-dihydrodibenzo[b,f][1,4]thiazepine-8-carboxamide 5-oxide;
N-(3,5-Difluorobenzyl)-10-methyl-11-oxo-10,11-dihydrodibenzo[b,f][1,4]thiazepine-8-carboxamide 5-oxide;
N-(2-(Dimethylamino)ethyl)-10-methyl-11-oxo-10,11-dihydrodibenzo[b,f][1,4]thiazepine-8-carboxamide 5-oxide;
10-Methyl-11-oxo-N-(pyridin-3-ylmethyl)-10,11-dihydrodibenzo[b,f][1,4]thiazepine-8-carboxamide 5-(R)-oxide;
N-(4-(Dimethylamino)butyl)-10-methyl-11-oxo-10,11-dihydrodibenzo[b,f][1, 4]thiazepine-8-carboxamide 5-oxide;
(R)-10-Methyl-11-oxo-N-(1-phenylethyl)-10,11-dihydrodibenzo[b,f][1,4]thiazepine-8-carboxamide 5-oxide;
(S)-N-(1-(4-Chlorophenyl)ethyl)-10-methyl-11-oxo-10,11-dihydrodibenzo[b,f][1,4]thiazepine-8-carboxamide 5-oxide;
(R)-N-(1-(4-Chlorophenyl)ethyl)-10-methyl-11-oxo-10,11-dihydrodibenzo[b,f][1,4]thiazepine-8-carboxamide 5-oxide;
10-Methyl-11-oxo-N-(pyridin-2-yl)-10,11-dihydrodibenzo[b,f][1,4]thiazepine-8-carboxamide 5-oxide;
10-Methyl-11-oxo-N-(pyridin-3-yl)-10,11-dihydrodibenzo[b,f][1,4]thiazepine-8-carboxamide 5-oxide;
10-Methyl-11-oxo-N-(pyridin-4-yl)-10,11-dihydrodibenzo[b,f][1,4]thiazepine-8-carboxamide 5-oxide;
10-Methyl-11-oxo-N-(3-(piperidin-1-yl)propyl)-10,11-dihydrodibenzo[b,f][1,4]thiazepine-8-carboxamide 5-oxide;
10-Methyl-11-oxo-N-(2,2,2-trifluoro-1-phenylethyl)-10,11-dihydrodibenzo[b,f][1,4]thiazepine-8-carboxamide 5-oxide;
10-Ethyl-11-oxo-N-(2,2,2-trifluoro-1-phenylethyl)-10,11-dihydrodibenzo[b,f][1,4]thiazepine-8-carboxamide 5-oxide;
10-Methyl-11-oxo-N-(2-(pyrrolidin-1-yl)ethyl)-10,11-dihydrodibenzo[b,f][1,4]thiazepine-8-carboxamide 5-(R)-oxide;
N-(3,4-Dichlorobenzyl)-10-methyl-11-oxo-10,11-dihydrodibenzo[b,f][1,4]thiazepine-8-carboxamide 5-oxide;
(R)-N-(1-(4-Bromophenyl)ethyl)-10-ethyl-11-oxo-10,11-dihydrodibenzo[b,f][1,4]thiazepine-8-carboxamide 5-oxide;
(R)-N-(1-(4-Bromophenyl)ethyl)-10-ethyl-11-oxo-10,11-dihydrodibenzo[b,f][1,4]thiazepine-8-carboxamide 5-(R)-oxide;
(R)-10-Ethyl-N-(1-(naphthalen-2-yl)ethyl)-11-oxo-10,11-dihydrodibenzo[b,f][1,4]thiazepine-8-carboxamide 5-oxide; or
(R)-10-Ethyl-N-(1-(naphthalen-2-yl)ethyl)-11-oxo-10,11-dihydrodibenzo[b,f][1,4]thiazepine-8-carboxamide 5-(R)-oxide.

18. A compound or pharmaceutically acceptable salt thereof, wherein the compound is
   N-(4-Methoxybenzyl)-9,10-dioxo-9,10-dihydroanthracene-2-carboxamide;
   10-ethyl-N-(4-methoxybenzyl)-11-oxo-10,11-dihydrodibenzo[b,f][1,4]thiazepine-8-carboxamide 5,5-dioxide; or
   3-(1,3-dioxoisoindolin-2-yl)-N-(4-methoxybenzyl)benzamide.

19. A pharmaceutical composition comprising a compound or salt of claim 1 and a pharmaceutically acceptable carrier.

20. A method of treating a patient suffering from Tourette's syndrome, bipolar disorder, hyperprolactinemia, psychosis, depression, Huntington's chorea, or schizophrenia, comprising administering an effective amount of a compound or salt of claim 1 to the patient.

21. A compound or pharmaceutically acceptable salt thereof of claim 17, wherein the compound is 10-Methyl-11-oxo-N-(2-(thiophen-2-yl)ethyl)-10,11-dihydrodibenzo[b,f][1,4]thiazepine-8-carboxamide 5-(S)-oxide.

22. A compound or pharmaceutically acceptable salt thereof of claim 17, wherein the compound is 10-Methyl-11-oxo-N-(2-(thiophen-2-yl)ethyl)-10,11-dihydrodibenzo[b,f][1,4]thiazepine-8-carboxamide 5-oxide.

* * * * *